United States Patent [19]

Just et al.

[11] Patent Number: 5,734,041
[45] Date of Patent: Mar. 31, 1998

[54] PREPARATION OF CHIRAL PHOSPHOROTHIOATE OLIGOMERS

[75] Inventors: George Just, Ile Cadieux; Zhili Xin, Montreal; Eric Marsault, Montreal; Yi Jin, Montreal, all of Canada

[73] Assignee: McGill University, Montreal, Canada

[21] Appl. No.: 546,198

[22] Filed: Oct. 20, 1995

[51] Int. Cl.⁶ .............................. C07H 1/02; C07H 21/04
[52] U.S. Cl. ........................................ 536/25.31; 536/25.3
[58] Field of Search ............................... 536/26.31, 26.3

[56] References Cited

U.S. PATENT DOCUMENTS

| Re. 34,069 | 9/1992 | Köster et al. | 536/27 |
|---|---|---|---|
| 3,846,374 | 11/1974 | Farley et al. | 260/551 P |
| 4,458,066 | 7/1984 | Caruthers et al. | 536/27 |
| 4,500,707 | 2/1985 | Caruthers et al. | 536/27 |
| 4,668,777 | 5/1987 | Caruthers et al. | 536/27 |
| 4,725,677 | 2/1988 | Köster et al. | 536/27 |
| 4,973,679 | 11/1990 | Caruthers et al. | 536/27 |
| 5,132,418 | 7/1992 | Caruthers et al. | 536/27 |
| 5,646,267 | 7/1997 | Stec et al. | 536/25.33 |

FOREIGN PATENT DOCUMENTS

| 2 317 453 | 4/1973 | Germany . |
| WO 88/02004 | 3/1988 | WIPO . |
| WO 92/02258 | 2/1992 | WIPO . |
| 9639413 | 12/1996 | WIPO . |

OTHER PUBLICATIONS

Huang, Y. et al., "Study of the Conformation Equilibria of 2–Z–Methyl–1,3,2–oxazaphosphorinanes. Steric and Stereoelectronic Influences on the Orientation of the Me2N Substituent on Three–Coordinate Phosphorous", *J. Org. Chem.*, 1995, vol. 60, pp. 4767–4773.

Nifantyev, E.E. et al., "1,3,22–Oxazaphosphorinanes in Rhodium (I) Complexes, *J. Organometallic Chem.*, 1987 vol. 336, pp. 237–247.

Hall, G. et al., "Platinum (II) Complexes of P(III) Cyclophosphamide Derivatives," *Phosphorus & Sulfur*, 1979, vol. 7, pp. 235–240.

Nuretdinov, I. et al. "Nuclear Quadrupole Resonance of Chlorides&Amides of Phosphorus (III) Cyclic Acids," *Chem.Abstracts*, 1979, vol. 90, p. 612.

Xin, Z. et al., "Diastereoselective Synthesis of Phosphite Triesters", *Tetrahedron Letters*, 1996, vol. 37, pp. 969–972.

Jin, Y. et al. "A Stereoselective Synthesis of Dinucleotide Phosphorothioates, Using Chiral Phopsphoramidites as Intermediates", *Tetrahedron Letters*, 1996, vol. 37, pp. 973–976.

Marsault, E. et al., "Diastereoselective Synthesis of Phosphite Triesters Through a New Bicyclic Intermediate", *Tetrahedron Letters*, 1996, vol. 37, pp. 977–980.

Bielinska, A. et al., "Regulation of gene expression with double–stranded phosphorothioate oligonucleotides", *Science* 1990, 250, 997–1000.

Brody, R. et al., "Stereochemical course of nucleotidyl catalyzed bacteriophage T7 induced DNA polymerase", *Biochemistry* 1982, 21, 2570–2572.

Brody, R. and Frey, P., "Unambiguous determination of the sterochemistry of nucleotidyl transfer catalyzed by DNA polymerase I from *Escherichia coli* ", *Biochemistry* 1981, 20, 1245–1252.

Bryant, F. and Benkovic, S., "Stereochemical course of the reaction catalyzed by 5'–nucleotide phosphodiesterase from snake venom", *Biochemistry* 1979, 2825–2628.

Burgers, P. and Eckstein, F., "A study of the mechanism of DNA polymerase I from *Escherichia coli* with diastereomeric phosphorothioate analogs of deoxyadenosine triphosphate", *J. of Biological Chemistry* 1979, 254 (15), 6889–6993.

Burgers, P. and Eckstein, F., "Absolute configuration of the diastereomers of adenosine 5'–0–(thiotriphosphate): Consequences for the stereochemistry of polymerization by DNA–dependent RNA polymerase from *Escherichia coli*", *Proc. Natl. Acad. Sci. USA* 1978, 75 (10), 4798–4800.

Cruse et al., "Chiral Phosphorothioate Analogues of B–DNA", *J. Mol. Biol.* 1986, 192, 891–905.

Eckstein, F. and Jovin, T.M., "Assignment of Resonances in the Phosphorus–31 Nuclear Magnetic Resonance Spectrum of Poly [d(A–T)] from Phosoporothioate Substitution", *Biochemistry* 1983, 22, 4546–4550.

Fujii, et al., "Acylphosphonates. 7.[1]A New Method for Stereospecific and Stereoselective Generation of Dideoxyribonucleoside Phosphorothioates via the Acylphosphonate Intermediates", *Tetrahedron* 1987, 43, 3395–3407.

Gupta, et al., "Template–Primer–Dependent Turnover of (Sp) –dATP S by T4 DNA Polymerase", *The Journal of Biological Chemistry* 1982, 257, 7689–7692.

Iyer, R. et al., "The automated synthesis of sulfur–containing oligodeoxyribonucleotides using 3H–1, 2–benzodithiol–3–one 1, 1–dioxide as a sulfur–transfer reagent", *J. Org. Chem.* 1990, 55, 4963–4699.

Iyer, R. et al., Beaucage, Serge L. et al., "3H–1, 2–benzodithiole–3–one 1,1–dioxide as an improved sulfurizing reagent in the solid–phase synthesis of oligodeoxyribonucleoside phosphorothiioates", *J. Am. Chem. Soc.* 1990, 112, 1253–1254.

Jäger, A. et al., "Oligonucleotide N–alkylphosphoramidates: Synthesis and binding to polynucleotides", *Biochemistry* 1988, 27, 7237–7246.

Kamer et al., "An Efficient Approach Toward the Synthesis of Phosphorothioate Diesters Via the Schonberg Reaction", *Tetrahedron Letters* 1989, 30, 6757–6760.

Koole, L. H. et al., "Enhanced stability of a Watson & Crick DNA duplex structure by methylation jof the phosphate groups in one strand", *Proc. K. Ned. Acad. Wet.* 1987, 90(1), 41–46.

Letsinger et al., "Effects of pendant groups at phosphorus on binding properties of d–ApA analogues", *Nucleic Acids Research* 1986, 14, 3487–349.

(List continued on next page.)

*Primary Examiner*—Gary L. Kunz
*Attorney, Agent, or Firm*—Woodcock Washburn Kurtz Mackiewicz & Norris, LLP

[57] ABSTRACT

Methods and intermediates for the preparation of oligomers containing diastereomerically enriched phosphorothioate linkages are disclosed.

36 Claims, No Drawings

OTHER PUBLICATIONS

Miller, P.S. et al., "Biochemical and Biological Effects of Nonionic Nucleic Acid Methylphosphonates", *Biochemistry* 1981, 20, 1874–1880.

Niewiarowski, W., et al., "Diastereomers of Thymidine 3'O–(Methanephosphono-thioate): Synthesis, Absolute Configuration and Reaction with 3'-methoxyacetylthymidine Under Conditions of Triester Approach to Oligonucleotide Synthesis", *Acta Biochimica Polonia* 1987, 34, 217–231.

Rao et al., "Dibenzoyl Tetrasulphide–A Rapid Sulphur Transfer in the Synthesis of Phosphorothioate Analoques of Oligonucleotides", *Tetrahedron Letters* 1992, 33 (33), 4839–4842.

Romaniuk, P. J. and Eckstein, F., *"A study of the mechanism of t4 DNA polymerase with diasteromeric phosphorothioate analogues of deoxyadenosine triphosphate"*, Biological Chemistry 1982, 257 (13), 7684–7688.

Stec, W.J., "Stereospecific synthesis of oligonucleotide p–chiral analogues", *Polish Academy of Sciences* 1989 Jun. 18–21.

Stec, W. and Wilk, "Stereocontrolled Synthesis of Oligo (nucleoside phosphorothioate)s", *Angew. Chem. Int. Ed. Engl.* 1994, 33, 709–722.

Stec et al., "Reversed–phase High–performance Liquid Chromatographic Separation of Diastereomeric Phosphorothioate Analogues of Oligodeoxyribonucleotides and Other Backbone–Modified Congeners of DNA", *J. Chromatography* 1985, 326, 263–280.

Takahata, H. et al., "Concise Syntheses of Natural γ–Butyrolactones, (+)–trans–Whisky Lactone, (+)–trans–Cognac Lactone, (–) –Methylenolactocin, (+) –Nephrosteranic Acid, and (+) –Roccellaric Acid Using Novel Chiral Butenolide Synthons", *J. Org. Chem.* 1995, 60, 5628–5633.

Ueda, T. et al., "Phosphorothioate–containing RNAs show mRNA activity in the prokaryotic translation systems in vitro", *Nucleic Acids Research* 1991, 19, 547–552.

Vu, H. and Hirschbein, B.L., "Internucleotide Phosphate Sulfurization with Tetraethylthiuram Disulfide, Phosphorothioate Oligonucleotide Synthesis via Phosphoramidite Chemistry", *Tetrahedron Letters* 1991, 32(26), 3005–3008.

Wu H. et al., "Inhibition of in vitro transcription by specific double stranded oligodeoxyribonucleotides", *Gene* 1990, 89, 203–209.

PREPARATION OF CHIRAL PHOSPHOROTHIOATE OLIGOMERS

FIELD OF THE INVENTION

This invention relates to methods for the preparation of diastereomerically enriched phosphorothioate linked oligonucleotides, and to intermediates useful in their preparation. This invention also relates to sequence-specific phosphorothioate oligonucleotides having chiral phosphorus linkages and to a novel chemical synthesis of these and other oligonucleotides.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. Classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect might be obtained with minimal side effects. It is the general object of such therapeutic approaches to interfere with or otherwise modulate gene expression which would lead to undesired protein formation.

One method for inhibiting specific gene expression is with the use of oligonucleotides. Oligonucleotides complementary to a specific target messenger RNA (mRNA) sequence are used. Several oligonucleotides are currently undergoing clinical trials for such use.

Transcription factors interact with double-stranded DNA during regulation of transcription. Oligonucleotides can serve as competitive inhibitors of transcription factors to modulate the action of transcription factors. Several recent reports describe such interactions (see, Bielinska, et. al., *Science* 1990, 250, 997–1000; and Wu, et al., *Gene* 1990, 89, 203–209.)

Oligonucleotides also have found use in diagnostic tests. Such diagnostic tests can be performed using biological fluids, tissues, intact cells or isolated cellular components. As with the above gene expression inhibition, diagnostic use can take advantage of an oligonucleotide's ability to hybridize with a complementary strand of nucleic acid. Hybridization is the sequence specific hydrogen bonding of oligonucleotides via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of such other biological molecules. One particular use, the use of oligonucleotides as primers in the reactions associated with polymerase chain reaction (PCR), has been the cornerstone for the establishment of an ever expanding commercial business. The use of such PCR reactions has seemingly "exploded" as more and more use of this very important biological tool is made. The uses of PCR have extended into many areas in addition to those contemplated by its Nobel laureate inventor. Examples of such new areas include forensics, paleontology, evolutionary studies and genetic counseling to name just a few. Primers are needed for each of these uses. Oligonucleotides, both natural and synthetic, serve as the primers.

Oligonucleotides also are used in other laboratory procedures. A number of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et. al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA from Book 2 of *Molecular Cloning, A Laboratory Manual*, ibid. and DNA-Protein Interactions and The Polymerase Chain Reaction from Vol. 2 of *Current Protocols In Molecular Biology*, ibid.

To supply the users of oligonucleotides, many scientific journals now contain advertisements for either oligonucleotide precursors or for custom-synthesized oligonucleotides. This has become an important commercial use of oligonucleotides. Oligonucleotides can be synthesized to have properties that are tailored for the desired use. Thus, a number of chemical modifications have been introduced into oligonucleotides to increase their usefulness in diagnostics, as research reagents, and as therapeutic entities. These modifications are designed, for example, to increase binding to a target nucleic acid strand, to assist in identification of the oligonucleotide or an oligonucleotide-target complex, to increase cell penetration, to provide stability against nucleases and other enzymes that degrade or interfere with the structure or activity of the oligonucleotides, to provide a mode of disruption (terminating event) once sequence-specifically bound to a target, or to improve the pharmacokinetic properties of the oligonucleotides.

Since they exist as diastereomers, phosphorothioate, methylphosphonate, phosphotriester, phosphoramidate and other phosphorus oligonucleotides synthesized using known, automated techniques result in mixtures of Rp and Sp diastereomers at the individual phosphorothioate, methylphosphonate, phosphotriester, phosphoramidate or other phosphorus linkages. Thus, a 15-mer oligonucleotide containing 14 asymmetric linkages has $2^{14}$, i.e. 16,384, possible stereoisomers. It is possible that oligomers having diastereomerically enriched linkages could possess advantages in hybridizing to a target mRNA or DNA. Accordingly, there is a need for such oligomers.

Miller, P. S., McParland, K. B., Jayaraman, K., and Ts'o, P. O. P (1989), *Biochemistry*, 20:1874, found that small di-, tri- and tetramethylphosphonate and phosphotriester oligonucleotides hybridize to unmodified strands with greater affinity than natural phosphodiester oligonucleotides. Similar increased hybridization was noted for small phosphotriester and phosphoramidate oligonucleotides; Koole, L. H., van Genderen, M. H. P., Reiners, R. G., and Buck, H. M. (1987), *Proc. K. Ned. Adad. Wet.*, 90:41; Letsinger, R. L., Bach, S. A., and Eadie, J. S. (1986), *Nucleic Acids Res.*, 14:3487; and Jager, A., Levy, M. J., and Hecht, S. M. (1988), *Biochemistry*, 27:7237. The effects of the diastereomers of undefined stereochemistry on hybridization becomes even more complex as chain length increases.

Bryant, F. R. and Benkovic, S. J. (1979), *Biochemistry*, 18:2825 studied the effects of diesterase on the diastereomers of ATP. Published patent application PCT/US88/03634 discloses dimers and trimers of 2',5'-linked diastereomeric adenosine units. Niewiarowski, W., Lesnikowski, Z. J., Wilk, A., Guga, P., Okruszek, A., Uznanski, B., and Stec, W. (1987), *Acta Biochimica Polonia*, 34:217, synthesized dimers of thymidine having high diastereomeric excess, as did Fujii, M., Ozaki, K., Sekine, M., and Hata, T. (1987), *Tetrahedron*, 43:3395.

Stec, W. J., Zon, G., and Uznanski, B. (1985), *J. Chromatography*, 326:263, have reported the synthesis of certain mixtures of phosphorothioates or methyphosphonate oligonucleotides and have separated them by chromatography. However, they were only able to separate the diastereomers of certain small oligomers having a limited number of diastereomerically pure phosphorus linkages.

In a preliminary report, J. W. Stec, *Oligonucleotides as antisense inhibitors of gene expression: Therapeutic implications*, meeting abstracts, Jun. 18–21, 1989, noted that a non-sequence-specific thymidine homopolymer octamer—i.e. a $(dT)_8$-mer, having "all-except-one" Rp configuration methylphosphonate linkages—formed a thermodynamically more stable hybrid with a 15-mer deoxyadenosine homopolymer—i.e. a $d(A)_{15}$-mer—than did a similar thymidine homopolymer having "all-except-one" Sp configuration methylphosphonate linkages. The hybrid between the "all-except-one" Rp $(dT)_8$-mer and the $d(A)_{15}$-mer had a Tm of 38° C. while the Tm of the "all-except-one" Sp $(dT)_8$-mer and the $d(A)_{15}$-mer was <0° C. The hybrid between a $(dT)_8$-mer having natural phosphodiester linkages, i.e. octathymidylic acid, and the $d(A)_{15}$-mer was reported to have a Tm of 14° C. The "all-except-one" thymidine homopolymer octamers were formed from two thymidine methylphosphonate tetrameric units with high diastereomeric excess linked by a natural phosphodiester linkage.

Six or more nucleotides units are generally necessary for an oligonucleotide to be of optimal use in applications involving hybridization. It is often preferred to have even more nucleoside units for best performance, often as many as 10 to 30. Because it has not been possible to stereochemically resolve more than two or three adjacent phosphorus linkages, the effects of induced chirality in the phosphorus linkages, chemically synthesized oligonucleotides has not been well assessed heretofore. This is because with few limited exceptions, the sequence-specific phosphorothioate, methylphosphonate, phosphotriester or phosphoramidate oligonucleotides obtained utilizing known automated synthetic techniques have been mixtures with no diastereomeric excess.

Some aspects of the use of enzymatic methods to synthesize oligonucleotides having chiral phosphorus linkages have been investigated. Burgers, P. M. J. and Eckstein, F. (1979), *J. Biological Chemistry*, 254:6889; and Gupta, A., DeBrosse, C., and Benkovic, S. J. (1982) *J. Bio. Chem.*, 256:7689 enzymatically synthesized diastereomerically pure polydeoxy-adenylic acid having phosphorothioate linkages. Brody, R. S. and Frey, P. S. (1981), *Biochemistry*, 20:1245; Eckstein, F. and Jovin, T. M. (1983), *Biochemistry*, 2:4546; Brody, R. S., Adler, S., Modrich, P., Stec, W. J., Leznikowski, Z. J., and Frey, P. A. (1982) *Biochemistry*, 21:2570–2572; and Romaniuk, P. J. and Eckstein, F. (1982) *J. Biol. Chem.*, 257:7684–7688 all enzymatically synthesized poly TpA and poly ApT phosphorothioates while Burgers, P. M. J. and Eckstein, F. (1978) *Proc. Natl. Acad. Sci. USA*, 75:4798–4800 enzymatically synthesized poly UpA phosphorothioates. Cruse, W. B. T., Salisbury, T., Brown, T., Cosstick, R. Eckstein, F., and Kennard, O. (1986), *J. Mol. Biol.*, 192:891, linked three diastereomeric Rp GpC phosphorothioate dimers via natural phosphodiester bonds into a hexamer. Most recently Ueda, T., Tohda, H., Chikazuni, N., Eckstein, R., and Watanabe, K. (1991) *Nucleic Acids Research*, 19:547, enzymatically synthesized RNA's having from several hundred to ten thousand nucleotides incorporating Rp linkages of high diastereomeric excess. Enzymatic synthesis, however, is disadvantageous in that it depends on suitable polymerases that may or may not be available, especially for modified nucleoside precursors.

As reviewed by W. J. Stec and A. Wiek (1994), *Angew. Chem. Int. Ed. English* 33:709, the oxathiaphospholane method has been successful for the preparation of phosphorothioates with defined stereochemistry. However, it suffers from disadvantages, such as the non-trivial preparation of diastereomerically pure oxathiaphospholane, and the difficulty in synthesizing and isolating satisfactorily pure oligomers longer than 12-mers.

It would therefore be of great advantage to provide oligonucleotides having phosphorus linkages with controlled stereochemistry.

OBJECTS OF THE INVENTION

It is one object of this invention to provide sequence-specific oligonucleotides having chirally pure phosphorothioate linkages with high diastereomeric excess.

Another object is to provide phosphorus-linked oligonucleotides having substantially all Rp or all Sp linkages.

A further object is to provide research and diagnostic materials for assaying bodily states in animals, especially diseased states.

It is yet another object to provide new methods for synthesizing sequence-specific oligonucleotides having chirally pure phosphorothioate linkages, and useful intermediates therefor.

SUMMARY OF THE INVENTION

The present invention provides stereoselective methods for preparing sequence-specific oligonucleotides having chiral phosphorus linkages. In certain preferred embodiments, these methods comprise the steps of:

reacting a first synthon of Formula I:

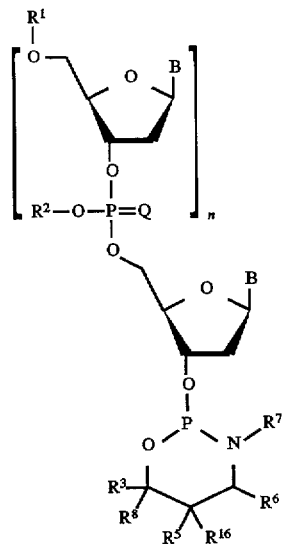

wherein:

Q is independently O or S;

$R^1$ is a hydroxyl protecting group;

$R^2$ is a chiral auxiliary of formula —$C(R^8)R^3$—$C(R^{16})R^5$—$CHR^6$—$NHR^7$;

$R^3$ is hydrogen, alkyl, cyanomethyl, monohalomethyl, dihalomethyl, trihalomethyl, —$CH_2Si(R^4)_3$, or —$CH_2$—$SO_kR^4$ where k is 0, 1 or 2;

R⁴ is independently alkyl, aryl, aralkyl or alkaryl having up to 15 carbon atoms;

R⁵ is H, —CN, —Si(R⁴)₃, SO_kR⁴ or halogen;

or R⁸ and R¹⁶ are each H, and R³ and R⁵, together, form one of the structures:

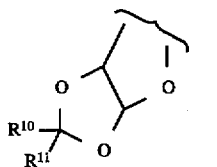

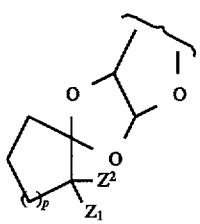 or 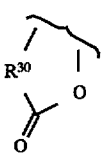

wherein:

R¹⁰ and R¹¹ are H, alkyl having from 1 to about 10 carbons, —CH₂C(=O)OR²², —CH₂CN, —CH₂Si(CH₃)₃, or o- or p-C₆H₄—R²¹;

R²¹ is hydrogen, —O—C(=O)CH₃, alkoxy having from 1 to about 10 carbons, —NO₂, or —N(R²²)₂;

R²² is independently H or alkyl having from one to about 10 carbon atoms;

p is 1 or 2;

Z¹ and Z² are independently halogen, —CN, —Si(CH₃)₃, and —C(=O)OR²²;

R³⁰ is hydrogen, —O—C(=O)CH₃, alkoxy having from 1 to about 10 carbons, or —O—Si(R₄)₃;

R⁶ is H, alkyl or aralkyl having up to 15 carbon atoms;

or R⁵ and R⁶, together with the atoms to which they are attached, form a 5 or 6 membered ring;

R⁷ is alkyl or aralkyl having up to 15 carbon atoms;

or R⁶ and R⁷, together, form one of the structures

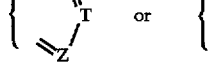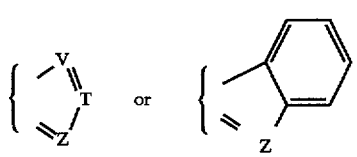

wherein V, T, and Z are independently CH or N;

R⁸ is H or methyl;

R¹⁶ is H, alkyl or aralkyl having up to 15 carbon atoms;

B is a nucleobase; and n is an integer from 0 to 50; with a second synthon of Formula II:

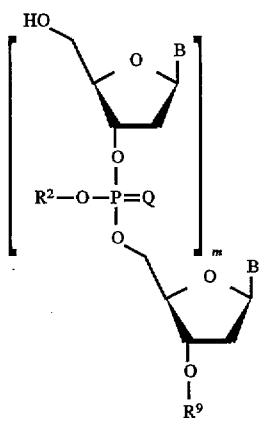

wherein:

R⁹ is a hydroxyl protecting group or a linker connected to a solid support; and m is an integer from 0 to 50; for a time and under reaction conditions effective to form a third synthon of Formula III:

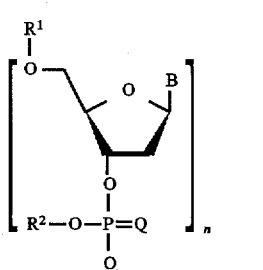

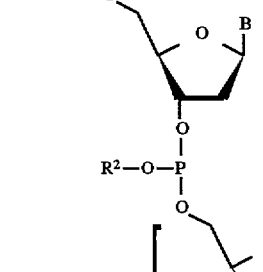

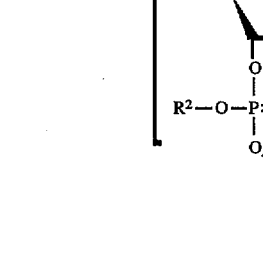

contacting said third synthon with a sulfurizing agent to form an oligomer of Formula IV:

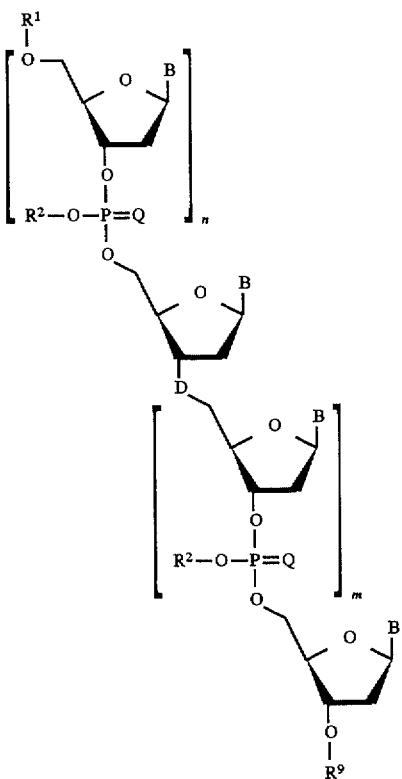

wherein D is said phosphorothioate linkage having the formula:

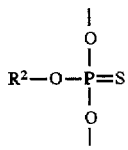

In preferred embodiments, said phosphorothioate linkage is diastereomerically enriched. In other preferred embodiments about 75% of the phosphorothioate linkage is in a single stereoisomeric form. In further preferred embodiments about 85% of the phosphorothioate linkage is in a single stereoisomeric form. In especially preferred embodiments about 95% of the phosphorothioate linkage is in a single stereoisomeric form. Most preferably, the phosphorothioate linkage is in a single stereoisomeric form, substantially free of other stereoisomeric forms. Preferably, the first synthon is in a single stereoisomeric form, substantially free of other stereoisomeric forms.

In some preferred embodiments n is 0. In further preferred embodiments, $R^1$ groups are subsequently removed to yield new second synthons for iterative synthesis, and chiral auxiliaries are removed after iterative synthesis is completed. In preferred embodiments of the present methods the oligomer of Formula IV contains a plurality of phosphorothioate linkages.

Preferably, first and second synthons are reacted at a temperature of from about −20° C. to about 40° C., with from about −15° C. to about 0° C. being more preferred.

In some preferred embodiments the first synthon is formed by reacting a compound of Formula V:

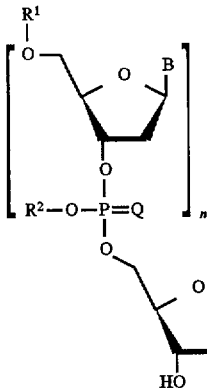

with an azaphospholane of Formula VIa:

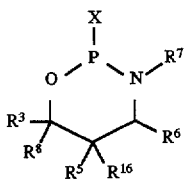

wherein $R^3$-$R^8$ are as defined above; and X is halogen, dialkylamino, imidazole, triazole or substituted phenoxy wherein said substituents are electron withdrawing, preferably halogen or nitro.

In some embodiments the azaphospholane described above is produced by reacting a reagent of formula HO—C($R^8$)$R^3$—C($R^{16}$)$R^5$—CHR$^6$—NHR$^7$ and a phosphorus trihalide, phosphorus tri(dialkylamide), phosphorus triphenoxide or phosphorus triimidazolide.

In more preferred embodiments the first synthon is formed by reacting a compound of Formula VII:

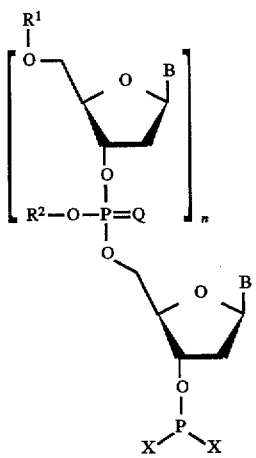

and a γ-amino alcohol of formula HO—C($R^8$)$R^3$—C($R^{16}$) $R^5$—CHR$^6$—NHR$^7$. Preferably, X is chlorine, dialkylamino or diphenoxy, and said reaction is stereoselective. It is especially preferred that the first synthon is in a single stereoisomeric form, substantially free of other stereoisomeric forms.

In some preferred embodiments the reaction of first and second synthons is performed in the presence of a catalyst, said catalyst preferably having one of the Formulas VIII or IX:

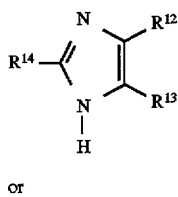 VIII or

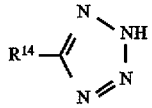 IX wherein:

R$^{12}$ and R$^{13}$ are independently hydrogen, halogen, cyano, nitro, alkyl having from one to 10 carbons, substituted alkyl having from one to 10 carbons, an ester group, or R$^{12}$ and R$^{13}$ together with the carbon atoms to which they are attached, form a substituted or unsubstituted phenyl ring where said substituents are electron withdrawing; and R$^{14}$ is hydrogen, halogen, cyano, nitro, thio, lo alkyl having from one to 10 carbons, substituted alkyl having from one to 10 carbons, norbornyl, substituted norbornyl, aryl, substituted aryl wherein said substituents are electron withdrawing, or has the formula:

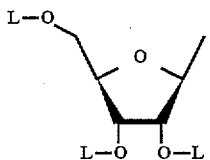

wherein L is protecting group.

In some preferred embodiments R$^{14}$ is halogen or nitro, preferably bromine, and R$^{12}$ and R$^{13}$ are each halogen or each cyano, with cyano being especially preferred.

Other preferred embodiments R$^{14}$ has one of the formulas:

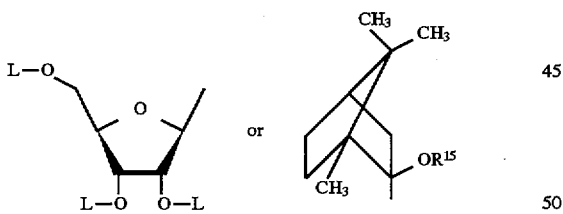

wherein R$^{15}$ is H, methyl, trialkylsilyl or acetyl.

In some preferred embodiments of the method R$^3$ is cyanomethyl or —CH$_2$—SO$_k$R$^4$ where k is 0, 1 or 2, and R$^7$ is lower alkyl or aralkyl.

In further preferred embodiments said first synthon has one of the Formulas Xa, XIa, XIIa, XIIIa or XXa:

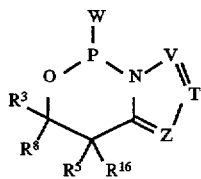 Xa

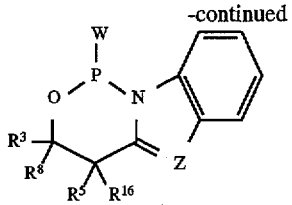 XIa

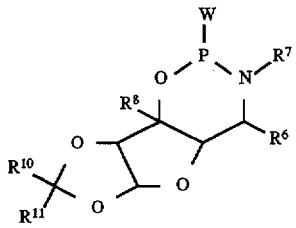 XIIa

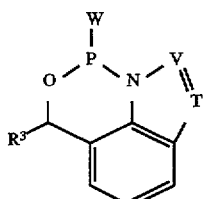 XIIIa

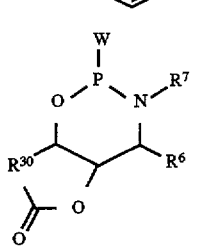 XXa wherein W has the formula:

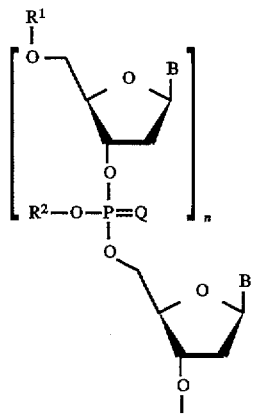

and R$^1$-R$^{16}$, V, T and Z are as defined above,

Other preferred first synthons have the Formula Xb or Xc:

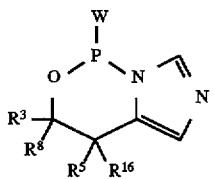 Xb

-continued

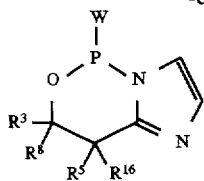
Xc

More preferred first synthons have the Formula XVIIa or XVIIIa:

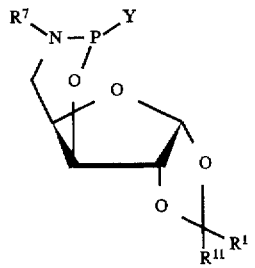
XVIIa

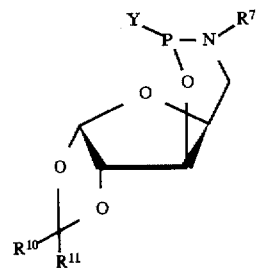
XXVIIIa

Particularly preferred first synthons have the Formula XIVa:

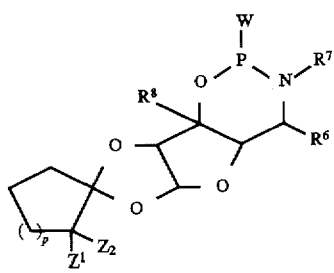
XIVa

Especially preferred first synthons have the Formula XVa or XVIa:

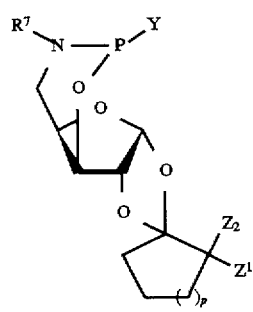
XVa

-continued

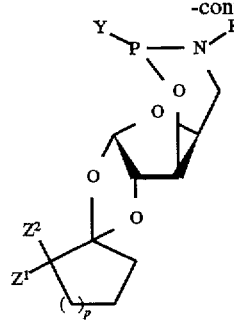
XVIa

In preferred embodiments of the methods of the invention $R^1$ groups are removed from the oligomers, thus creating new second synthons for further iterative synthesis.

Also provided according to the invention are phosphorothioate oligomers produced by the method of claim 1, and azaphospholanes having Formula VIb:

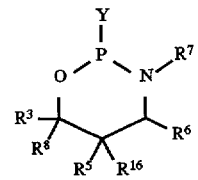
VIb

In preferred embodiments of the invention, 75% of said azaphospholanes having Formula VIb are in a single stereoisomeric form, with 85% being more preferred, and 95% being particularly preferred. In especially preferred embodiments, the azaphospholanes having Formula VIb are in a single stereoisomeric form, substantially free of other stereoisomeric forms.

In preferred embodiments the azaphospholane has one of the Formulas Xb, XIb, XIIb, XIIIb, Xd, Xe or XXb:

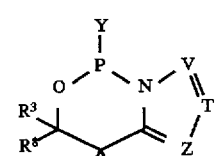
Xb

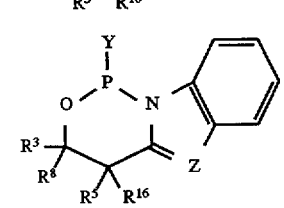
XIb

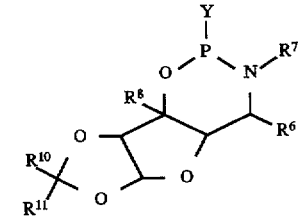
XIIb

-continued

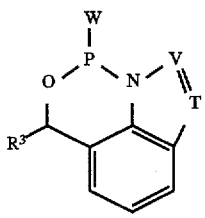
XIIIb

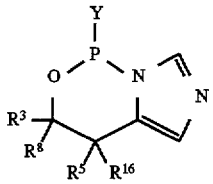

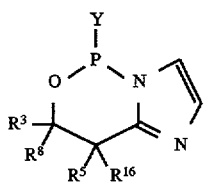

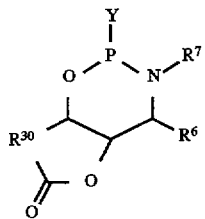
XXb

In other preferred embodiments the azaphospholane has the Formula XVIIb or XVIIIb:

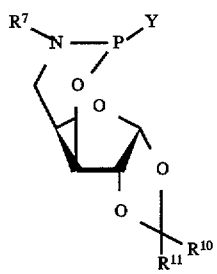
XVIIb

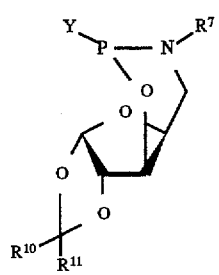
XVIIIb

In some particularly preferred embodiments the azaphosphalane has the Formula XIVb:

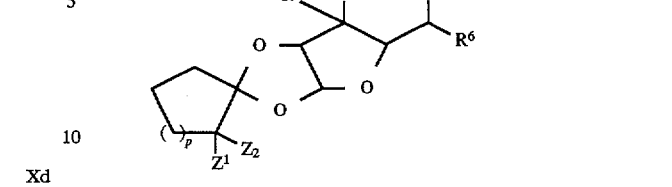
XIVb

Especially preferred embodiments the azaphospholane has the Formula XVb or XVIb:

XVb

XVIb

Also provided in accordance with the invention are oligomeric compounds comprising a phosphite linkage having the Formula XXX:

XXX

In preferred embodiments of the invention, 75% of said phosphosphite linkage is in a single stereoisomeric form, with 85% being more preferred, and 95% being particularly preferred. In especially preferred embodiments, the phosphosphite linkage is in a single stereoisomeric form, substantially free of other stereoisomeric forms.

DETAILED DESCRIPTION OF THE PREFERRED EMBODIMENTS

The present invention is directed to methods for the synthesis of phosphorothioate compounds having diastereomerically enriched phosphorothioate linkages, and to intermediates useful in their preparation.

In one aspect, the invention provides methods for the preparation of phosphorothioate linkages comprising the steps of reacting a first synthon of Formula I:

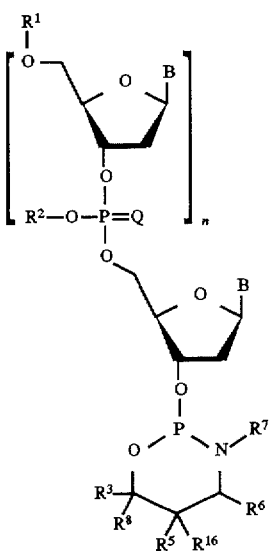

wherein:

Q is independently O or S;

$R^1$ is a hydroxyl protecting group;

$R^2$ is a chiral auxiliary of formula —$C(R^8)R^3$—$C(R^{16})$ $R^5$—$CHR^6$—$NHR^7$;

$R^3$ is hydrogen, alkyl, cyanomethyl, monohalomethyl, dihalomethyl, trihalomethyl, —$CH_2Si(R^4)_3$, or —$CH_2$—$SO_kR^4$ where k is 0, 1 or 2;

$R^4$ is independently alkyl, aryl, aralkyl or alkaryl having up to 15 carbon atoms;

$R^5$ is H, —CN, —$Si(R^4)_3$, $SO_kR^4$ or halogen;

or $R^8$ and $R^{16}$ are each H, and $R^3$ and $R^5$, together, form one of the structures

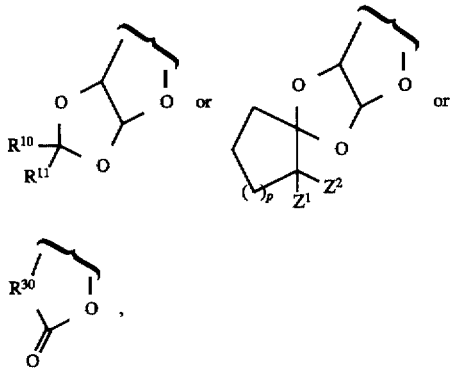

wherein:

$R^{10}$ and $R^{10}$ are H, alkyl having from 1 to about 10 carbons, —$CH_2C(=O)OR^{22}$, —$CH_2CN$, —$CH_2Si(CH_3)_3$, or o- or p-$C_6H_4$—$R^{21}$;

$R^{21}$ is hydrogen, —O—$C(=O)CH_3$, alkoxy having from 1 to about 10 carbons, —$NO_2$, or —$N(R^{22})_2$;

$R^{22}$ is independently H or alkyl having from one to about 10 carbon atoms;

p is 1 or 2;

$Z^1$ and $Z^2$ are independently halogen, CN, —$Si(CH_3)_3$, and —$C(=O)OR^{22}$;

$R^{30}$ is hydrogen, —O—$C(=O)CH_3$, alkoxy having from 1 to about 10 carbons, or —O—$Si(R_4)_3$;

$R^6$ is H, alkyl or aralkyl having up to 15 carbon atoms;

or $R^5$ and $R^6$, together with the atoms to which they are attached, form a 5 or 6 membered ring;

$R^7$ is alkyl or aralkyl having up to 15 carbon atoms;

or $R^6$ and $R^7$ together, form one of the structures

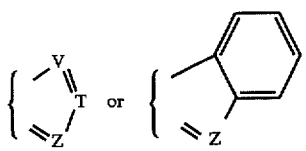

wherein V, T, and Z are independently CH or N;

$R^8$ is H or methyl;

$R^{16}$ is H, alkyl or aralkyl having up to 15 carbon atoms;

B is a nucleobase; and n is an integer from 0 to 50; with a second synthon of Formula II:

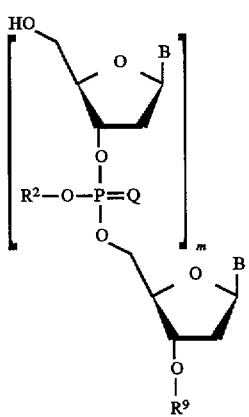

wherein:

$R^9$ is a hydroxyl protecting group or a linker connected to a solid support; and m is an integer from 0 to 50; for a time and under reaction conditions effective to form a third synthon of Formula III:

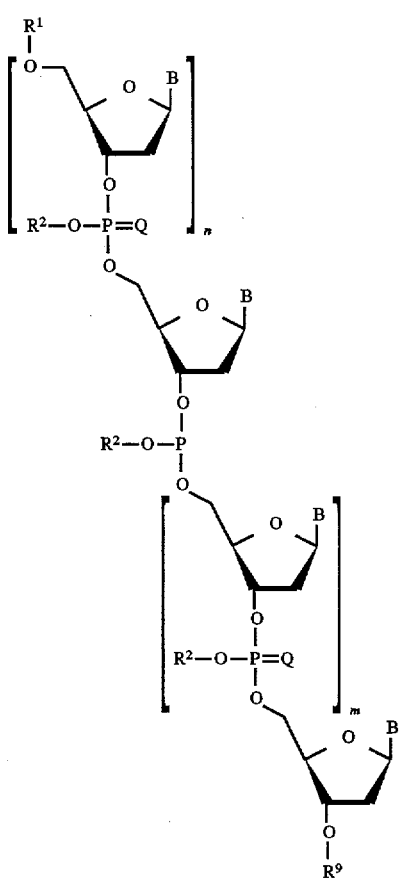
and
contacting said third synthon with a sulfurizing agent to form an oligomer of Formula IV:
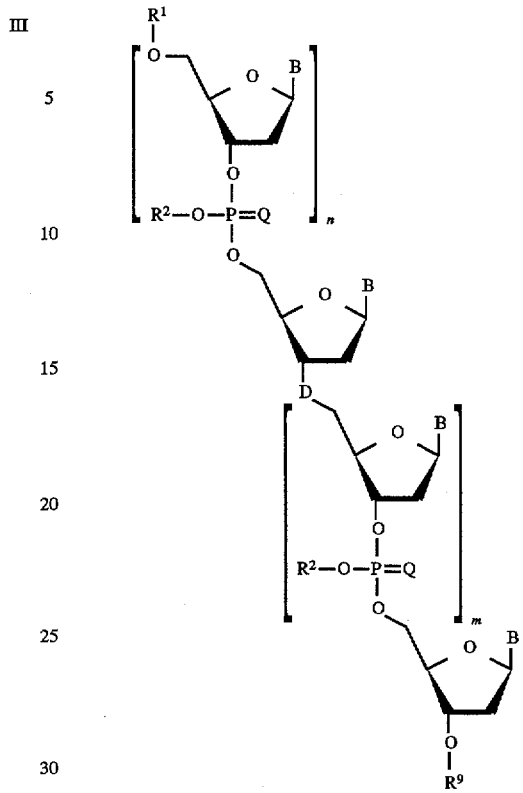
wherein D is said phosphorothioate linkage having the formula:
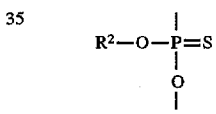
In accordance with the invention, first synthons are cyclic phosphoramidites having the general Formula VIc:
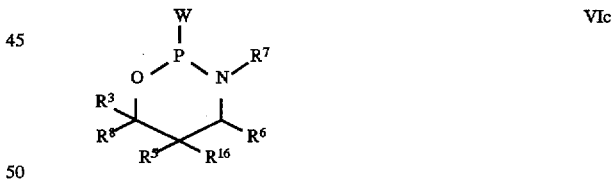

in which W, $R^3$, $R^5$–$R^8$ and $R^{16}$ are as defined above.

The reaction of first and second synthons is conducted in the presence of a catalyst. The structures of the first synthon and the catalyst are chosen such that the opening of the cyclic O—P—N phosphoramidite (azaphospholane) ring proceeds by the stereoselective breaking of the intracyclic P—N bond of the azaphospholane, to yield a third synthon, which is diastereomerically enriched at phosphorus. Accordingly, in preferred embodiments of the methods of the invention, first synthons are diastereomerically enriched, and more preferably in a single stereochemical form, substantially free of other stereochemical forms. It is also advantageous for the first synthon and the catalyst to bear substituent groups which are of relatively large size (i.e., bulky groups) to aid in the proper orientation of reactants to achieve the desired stereoselectivity. As used herein, the term stereoselective has its normal meaning as a process in which one stereoisomer is produced or destroyed more rapidly than another, resulting in a predominance of the favored stereoisomer.

In preferred embodiments catalysts have one of the Formulas VIII or IX:

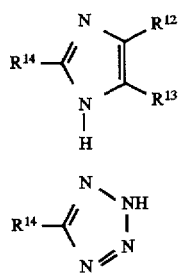

VIII

IX wherein $R^{12}$–$R^{14}$ are as defined above.

It has been found in accordance with the present invention that imidazole catalysts having electron-withdrawing substituents, in addition to substituents of relatively large size, are especially advantageous in production of stereochemically enriched products. While not wishing to be bound by a particular theory, it is believed that the catalyst first protonates the azaphospholane nitrogen, creating a good leaving group, which is displaced by the catalyst or its conjugate base. The imidazole or tetrazole attached to the phosphorus is then displaced either by the 3'-hydroxyl of the nucleosidic species, leading to a phosphite triester of high stereochemical purity, or by the catalyst, leading to epimerization.

It has been found in accordance with the present invention that catalysts which have appreciable acidity (i.e., which have pKa values of about 2 to 4) and which are relatively large can overcome the tendency toward epimerization at phosphorus, and result in stereoselective addition of the free 5'-hydroxyl of the nucleosidic species to be added. Thus, preferred substituents for groups $R^{13}$, $R^{14}$ and $R^{15}$ are those which are electron withdrawing, (and which therefore increase acidity), and of a size sufficient to maintain stereoselectivity. It will be recognized, however, that it is not necessary that all three groups $R_6$, $R_7$ and $R_8$ be of great bulk, so long as the overall size of the catalyst is sufficient to afford the desired stereoselectivity. Thus preferred $R^{12}$ and $R^{13}$ groups are independently hydrogen, halogen, cyano, nitro, alkyl having from one to 10 carbons, substituted alkyl having from one to 10 carbons, an ester group, or $R^{12}$ and $R^{13}$, together with the carbon atoms to which they are attached, form a substituted or unsubstituted phenyl ring where said substituents are electron withdrawing. Preferred $R^{14}$ groups include hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

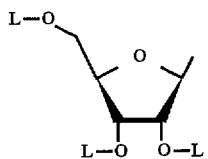

wherein L is protecting group. In preferred embodiments of the invention the catalyst is 2,4,5-tribromoimidazole, dibromocyanoimidazole, or dicyanobromoimidazole. In particularly preferred embodiments the catalyst is 4,5-dicyano-2-bromoimidazole.

It has been found in accordance with the present invention that the dicyanoimidazole, bromoimidazole, and tribromoimidazole catalysts described in accordance with the present invention are useful as substitutes for tetrazole catalysts in standard solid phase oligonucleotide synthetic regimes. Such synthetic procedures are well known in the art, and are extensively described in the literature. See for example, Caruthers U.S. Pat. Nos. 4,415,732; 4,458,066; 4,500,707; 4,668,777; 4,973,679; and 5,132,418; and Koster U.S. Pat. No. 4,725,677 and U.S. Pat. No. Re. 34,069, and *Oligonucleotides and Analogues, A Practical Approach*, Eckstein, F., IRL Press, New York (1991). The use of the catalysts of the invention in these synthetic methologies provides significant advantages over tetrazole catalysts, including, for example, significantly lower cost.

In other preferred embodiments $R^{14}$ has one of the formulas:

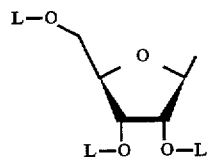

or

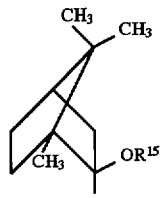

wherein $R^{15}$ is H, methyl, trimethylsilyl or acetyl.

In some preferred embodiments $R^6$ and $R^7$, together with the atoms to which they are attached, form an heterocyclic (i.e., imidazole, triazole or tetrazole) ring, which performs the function of the catalyst. Preferred first synthons which incorporate the catalyst therein have the general Formula Xa or XIIIa:

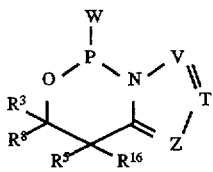
Xa

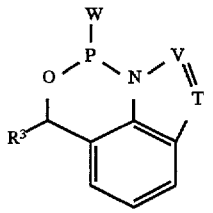
XIIIa wherein V, T and Z are each independently N or CH. In especially preferred embodiments the first synthons incorporate imidazole rings, and have the Formula Xb or Xc:

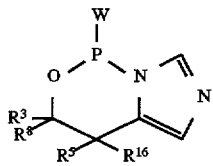
Xb

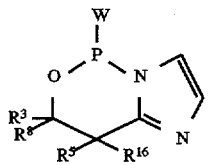
Xc

In further preferred embodiments of the invention the imidazole portions of the first synthons are further substituted, for example, by having a phenyl ring fused thereto. Thus in another preferred embodiment first synthons have the Formula XIa:

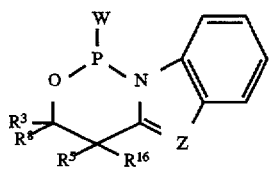
XIa

In further preferred embodiments, first synthons incorporate other relatively large substituent groups which facilitate the stereoselective opening of the azaphospholane ring. In particularly preferred embodiments first synthons have the Formula XIIa, and particularly Formula XVIIa or XVIIIa:

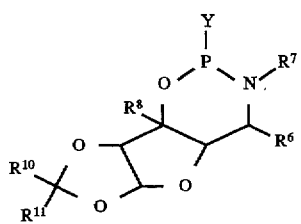
XIIa

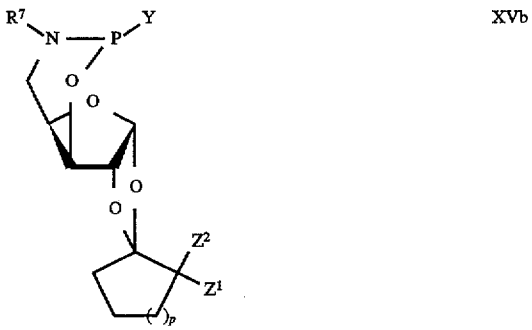

in which $R^{10}$ and $R^{11}$ are as defined above.

In especially preferred embodiments, first synthons have the Formula XVb or XVIb:

XVb

XVIb

In some preferred embodiments, the first synthon is obtained by reaction of a compound of Formula V:

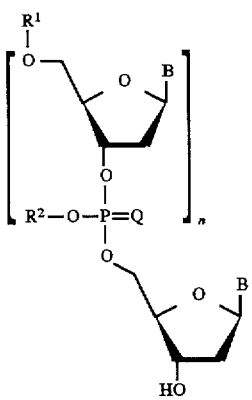

with an azaphospholane of Formula VIa:

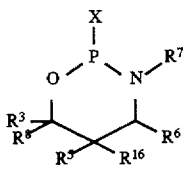

VIa wherein $R^3$–$R^8$ are as defined above; and X is halogen, preferably chlorine, dialkylamino, imidazole or substituted phenoxy wherein said substituents are electron withdrawing, and preferably are halogen or nitro.

In more preferred embodiments the first synthon is obtained by reaction of a compound of Formula VII:

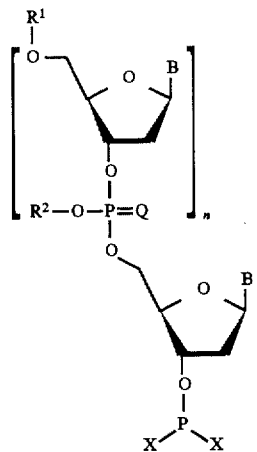

VIII and a γ-amino alcohol of formula HO—C($R^8$)$R^3$—C($R^{16}$) $R^5$—CHR$^6$—NHR$^7$; wherein X and $R^1$–$R^{16}$ are as defined above.

$R_2$ is a chiral auxiliary, which has the formula —C($R^8$) $R^3$—C($R^{16}$)$R^5$—CHR$^6$—NHR$^7$, and which is formed as a consequence of the opening of the cyclic phosphite ring. The chiral auxiliary functions as a protecting group for the phosphorus linkage during the course of the synthesis of oligomeric phosphorothioates. Accordingly, chiral auxiliaries are allowed to remain on the growing chain, and are removed at the end of the iterative synthetic regime. Removal of chiral auxiliaries can be conveniently accomplished in a single treatment after the completion of the iterative synthesis by treatment with either acidic reagents or by base catalyzed β-elimination. Suitable reagants include, for example, 70% trifluoroacetic acid, ammonia, and fluoride ion. Removal of chiral auxiliaries via β-elimination should be particularly advantageous where first synthons have the Formula XXa.

After reacting first and second synthons to form a third synthon, the third synthon is sulfurized to form a phosphorothioate linkage having the formula:

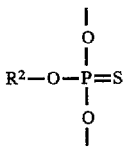

V

Sulfurization may be accomplished by any of the several sulfurizing agents known in the art to be suitable for conversion of phosphites into phosphorothioates. Useful sulfurizing agents include Beaucage reagent described in e.g., Iyer, R. P.; Egan, W.; Regan, J. B.; Beaucage, S. L., 3H-1,2-Benzodithiole-3-one 1,1-Dioxide as an Improved Sulfurizing Reagent in the Solid-Phase Synthesis of Oligodeoxyribonucleoside Phosphorothioates, *Journal of American Chemical Society*, 1990, 112, 1253–1254 and Iyer, R. P.; Phillips, L. R.; Egan, W.; Regan J. B.; Beaucage, S. L., The Automated Synthesis of Sulfur-Containing Oligodeoxyribonucleotides Using 3H-,2-Benzodithiol-3-one 1,1-Dioxide as a Sulfur-Transfer Reagent, *Journal of Organic Chemistry*, 1990, 55, 4693–4699. Tetraethyl-thiuram disulfide can also be used as described in Vu, H.; Hirschbein, B. L., Internucleotide Phosphite Sulfurization With Tetraethylthiuram Disulfide; Phosphorothioate Oligonucleotide Synthesis Via Phosphoramidite Chemistry, *Tetrahedron Letters*, 1991, 32, 3005–3007. Further useful reagents for this step are dibenzoyl Tetrasulfide, Rao, M. V.; Reese, C. B.; Zhengyun, Z., Dibenzoyl Tetrasulphide—A Rapid Sulphur Transfer Agent in the Synthesis of Phosphorthioate Analogues of Oligonucleotides, *Tetrahedron Letters*, 1992, 33, 4839–4842; di(phenylacetyl)disulfide, Kamer, R. C. R.; Roelen, H. C. P. F.; van den Eist, H.; van der Marel, G. A.; van Boom, J. H., An Efficient Approach Toward the Synthesis of Phosphorothioate Diesters Va the Schonberg Reaction *Tetrahedron Letters*, 1989, 30, 6757–6760sulfur; and sulfur in combination with ligands like triaryl, trialkyl or triaralkyl or trialkaryl phosphines.

The methods of the present invention can also be used to produce analogs of phosphorothioates, including phosphoroselenoates and phosphoroboronates. For example, phosphoroselenoates can be prepared by the methods of the invention by utilizing potassium selenocyanate in place of the sulfurizing agents described above. Phosphoroboronates can be prepared by similar adaptation of oxidizing agents known in the art. See, for example, *Antisense Research and Applications*, Crooks, S. T., and Lebleu, B., Eds. CRC Press, Boca Raton, Fla. (1993).

$R_9$ and $R_1$ can each be a hydroxyl protecting group. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. The tert-butyldimethylsilyl (TBDMS) group is representative of protecting groups useful for protecting the hydroxyl functionality. A preferred protecting group for $R^1$ is the dimethoxytrityl group. Other representative groups may be found in Greene, T. W. and Wuts, P. G. M., "*Protective Groups in Organic Synthesis*" 2d. Ed., Wiley & Sons, 1991. Typically, protecting groups are removed at the end of the iterative synthesis.

$R_9$ may alternatively be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. No. 4,725, 677 and U.S. Pat. No. Re. 34,069. Linkers are known in the art as short molecules which serve to connect a solid support to functional groups (e.g., hydroxyl groups) of initial synthon molecules in solid phase synthetic techniques. Suitable linkers are disclosed in *Oligonucleotides And Analogues A Practical Approach*, Ekstein, F. Ed., IRL Press, N.Y, 1991.

Alkyl groups according to the invention include straight chain, branched, and cyclic carbon and hydrogen containing groups such as methyl, isopropyl, and cyclohexyl groups. Preferred alkyl groups have 1 to about 6 carbon atoms.

Aralkyl groups according to the invention include both alkyl and aryl portions, although the point of attachment of such groups is through an alkyl portion thereof. Benzyl groups provide one example of an aralkyl group. Alkaryl groups include both alkyl and aryl portions, and are attached through their aryl portions. The term aryl is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms. The alkyl, alkaryl, and aryl groups may be substituted (e.g., i.e., bear halogens and hydroxy groups) or unsubstituted moieties.

Certain substituent groups of compounds of the invention bear electron withdrawing groups. As used herein, the term "electron withdrawing" has its normal meaning as a chemical functionality which electronically or inductively causes the withdrawal of electron density form the moiety to which the electron withdrawing groups is attached. Representative electron withdrawing groups include nitro groups and halogens. Other electron withdrawing groups will be apparent to those of skill in the art, once armed with the present disclosure.

Substituent B is a nucleobase. The term nucleobase as used herein is intended to include naturally occurring nucleobases (i.e., heterocyclic bases found in naturally occurring nucleic acids) and their non-naturally occurring analogs. Thus, nucleobases according to the invention include naturally occurring bases adenine (A), guanine (G), thymine (T), cytosine (C) and uracil (U), both in their unprotected state and bearing protecting or masking groups. Examples of nucleobase analogs include $N^4,N^4$-ethanocytosine, 7-deazaxanthosine, 7-deazaguanosine, 8-oxo-$N^6$-methyladenine, 4-acetylcytosine, 5-(carboxyhydroxymethyl) uracil, 5-fluorouracil, 5-bromouracil, 5-carboxymethylaminomethyl-2-thiouracil, 5-carboxymethylaminomethyl uracil, inosine, $N^6$-isopentyladenine, 1-methyladenine, 2-methylguanine, 5-methylcytosine, $N^6$-methyladenine, 7-methylguanine, 5-methylaminomethyl uracil, 5-methoxyaminomethyl-2-thiouracil, 5-methoxyuracil, pseudouracil, 5-methyl-2-thiouracil, 2-thiouracil, 4-thiouracil, 5-(1-propynyl)-4-thiouracil, 5-(1-propynyl)-2-thiouracil, 5-(1-propynyl)-2-thiocytosine, 2-thiocytosine, and 2,6-diaminopurine. Other suitable base analogs, for example the pyrimidine analogs 6-azacytosine, 6-azathymidine and 5-trifluoromethyluracil, may be found in Cook, D. P., et al., International Publication No. 92/02258, which is herein incorporated by reference.

The compounds of the invention are preferably up to 50 nucleobases in length, with 10 to 30 nucleobases being more preferred, and 15 to 25 nucleobases being especially preferred.

In preferred embodiments the phosphorothioate linkage produced by the method of the invention is diastereomerically enriched. The term "diastereomerically enriched" denotes the predominance of one stereochemical form over the other. In preferred embodiments the phosphorothioate linkage is 75% in a single stereochemical form. In further preferred embodiments the phosphorothioate linkage is 85% in a single stereochemical form, with 90% being further preferred and 95% being especially preferred. In further preferred embodiments the phosphorothioate linkage is in a single stereochemical form, substantially free of other stereochemical forms.

Preferably, following sulfurization, the phosphorothioate is next converted to a new first synthon. This is first accomplished by the removal of the 5'-hydroxyl protecting group $R_1$, under conditions which will necessarily depend upon the chemical identity of the specific $R_1$ group. After removal of the protecting group, the unprotected 5'-alcohol may be employed as a new second synthon in the iterative method. Libraries of dimeric and higher synthons may be prepared and stored to facilitate the iterative synthesis of desired nucleobase sequences.

Also provided according to the invention are azaphospholanes of Formula VIb:

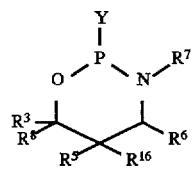

wherein Y is X or W, wherein X is halogen, dialkylamino, imidazole, or substituted phenoxy wherein said substituents are electron withdrawing, and W has the formula:

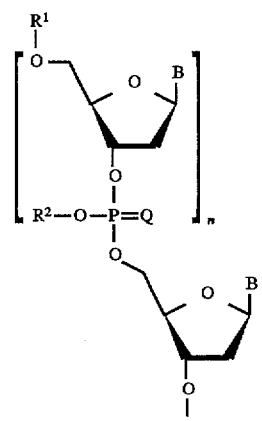

wherein constituent members are as defined above. Preferably, the azaphospholanes of Formula VIb are diastereomerically enriched in particular, it is advantageous to have defined stereochemistry around phosphorus atom, to afford diastereomerically enriched products upon stereoselective opening of the azaphospholane ring.

In preferred embodiments, compounds of the invention have one of the Formulas Xb, XIb, XIIb, XIIIb or XXb:

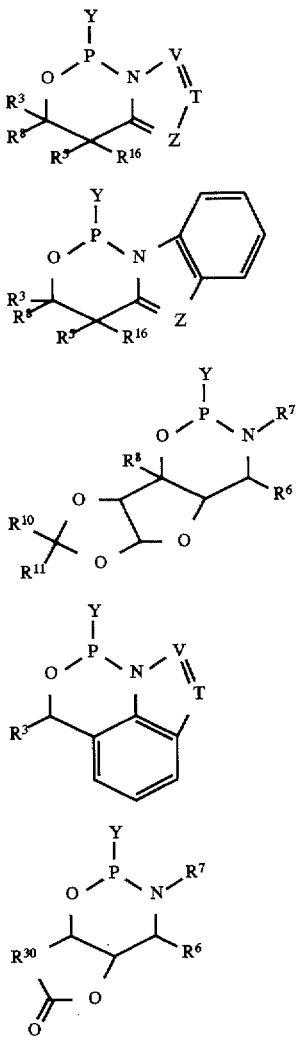

wherein $R^3-R^{16}$, Y, V, T, Z, $Z_1$, $Z_2$ and p are as defined above.

Particularly preferred embodiments of the compounds of the invention have the Formula XIVb, Xd, Xe, XVIIb, XVIIIb, XVb or XVIb:

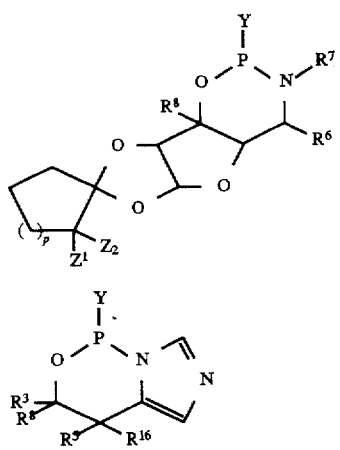

As used herein, the term "contacting" means directly or indirectly causing placement together of moieties to be contacted, such that the moieties come into physical contact with each other. Contacting thus includes physical acts such as placing the moieties together in a container. The term "reacting" as used herein means directly or indirectly causing moieties chemically combine or transform.

The method of the invention is performed in the presence of a solvent, for example chloroform or acetonitrile. Other solvents suitable for use in the present method will be readily apparent to those skilled in the art, once having been made aware of the present disclosure.

In general, it is preferred that the molar ratio of the catalyst to the first synthon starting material be from about 1 to about 50; preferably from about 2.5 to about 10.

The method of the present invention can be carried out in any suitable vessel which provides efficient contacting between the first and second synthons, and the catalyst. The reaction vessel used should be resistant to the components of the reaction mixture. Glass-lined vessels would be suitable for this purpose. Additional vessel materials will be apparent to those skilled in the art.

The reagents of the present method may be added in any order. The method is preferably carried out under an inert atmosphere, any should be carried out in a dry atmosphere. Any suitable inert gas may be employed, such as nitrogen, helium and argon.

Preferably, the method is carried out at temperatures ranging between about −20° C. and about 40° C., with temperatures ranging from about −15° C. to about 0° C. being more preferred.

Reaction time is generally from about one minute to about two hours, with reaction times of from about one minute to about 10 minutes being preferred.

Product can be recovered by any of several methods known to those of skill in the art. Preferably, products are recovered by chromatography. Additional separation of isomers can be accomplished by techniques known in the art including high performance liquid chromatography.

When $R^9$ is a solid support, purification is carried out after removal of the oligonucleotide from the solid support using methods known in the art.

The invention is further illustrated by way of the following examples. These examples are illustrative only and are not intended to limit the scope of the appended claims.

EXAMPLES

General methods

Melting points (m.p.) were determined using an Electrothermal MP apparatus and are uncorrected. Optical rotation measurements were carried out in the indicated solvents employing a Jasco DIP-140 digital polarimeter. Mass spectra (CI or EI) were obtained en an HP 5980A quadrupole mass spectrometer in the direct-inlet mode.

NMR spectra were recorded on Varian XL200, XL300, or Unity 500 spectrometers. Chemical shifts are given in the δ scale in parts per million. The assignments of proton spectra are based on COSY experiments. The residual proton signals of deuteriochloroform (δ7.24 ppm), methanol (δ3.30 ppm) and acetonitrile (δ1.93 ppm) were used as reference in these solvents. The multiplicities are recorded using the following abbreviations: s, singlet; d, doublet; t, triplet; q, quartet; m, multiplet. $^{31}$P NMR spectra were obtained on either a Varian XL200, XL300 or Unity 500 instrument, and chemical shifts are given with respect of aqueous phosphoric acid. Peak assignments of $^{13}$C-NMR spectra were, in some cases, made with the aid of APT, HMQC or HETCOR experiments.

Tetrahydrofuran (THF) was distilled from sodium benzophenone ketyl. Dichloromethane was distilled from $P_2O_5$. Triethylamine and acetonitrile were distilled from $CaH_2$. N,N-Dimethyl formamide was dried by shaking with KOH, followed by distillation. Thin-layer chromatography (TLC) was performed using Kieselgel 60 $F_{254}$ aluminium-backed plates (0.2 mm thickness) and visualized by UV and/or dipping in a solution of ammonium molybdate (2.5 g) and ceric sulfate (1 g) in 10% v/v aqueous sulphuric acid (100 ml), followed by heating. Kieselgel 60 (Merck 230–400 mesh) silica gel was employed for column chromatography.

Example 1

3R-hydroxy-N-iso-propylbutanoamide (10)

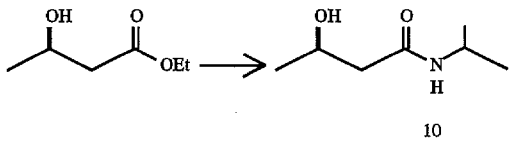

A 2M solution of trimethylaluminium in hexane (50 ml, 100 mmol) was slowly added to a solution of 8.5 ml (100 mmol) isopropylamine in 100 ml dichloromethane under nitrogen at room temperature. The mixture was stirred for 30 min and then cooled to 0° C. before 6.6 g (50 mmol) of ethyl-3R-hydroxybutanoate was added. The reaction mixture was stirred at room temperature for 2 hours for completion, carefully quenched with dilute HCl and extracted with chloroform. The organic extract was dried over $MgSO_4$ and concentrated to afforded 7 g N-isopropyl 3R-hydroxy butanoamide. After recrystallization, 5.5 g pure amide 10 was obtained (yield 76%).: m.p. 62° C.; $^1$H NMR (200 MHz, $CDCl_3$) δ6.41 (m, 1H, NH), 4.35 (b, 1H, OH), 3.78–4.15 (m, 2H, MeCH, $Me_2CH$), 2.08–2.32 (m, 2H, $CH_2$), 1.12 (d, J=6.3 Hz, 3H, Me), 1.07 (d, J=6.6 Hz, 6H, $NCHMe_2$); $^{13}$C NMR (50 MHz, $CDCl_3$) δ171.5 (C=O), 64.7 (CHOH), 43.8 (NHCH), 41.0 ($CH_2$), 22.7 (Me), 22.4 ($NCHMe_2$); MS(EI) m/e 145 ([M$^+$], 25%), 130 (27), 112 (4), 101 (6), 86 (34), 69 (8), 58 (22), 44 (100); HRMS(EI) m/e calc'd for $C_7H_{15}O_2N$ [M$^+$]: 145.1103, found 145.1109.

Example 2

2R-Hydroxy-4-(N-isopropyl)aminobutane (11)

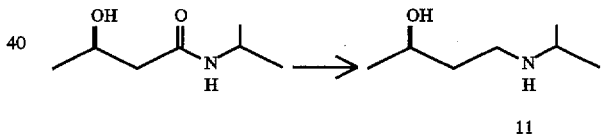

To a solution of 32 ml 1M borane (32 mmol) in THF was added 2.32 g (16 mmol) 3R-hydroxy-N-iso-propyl-butyl butanoamide 10 in 20 ml THF at 0° C. under nitrogen. The solution was then brought to reflux and maintained there for one hour. The reaction mixture was cooled to room temperature and 1N HCl was added slowly to quench the reaction. THF was removed in vacuo, and the aqueous solution was saturated with solid NaOH and then was extracted three times with a total 300 ml chloroform. The combined chloroform phase was dried, filtered and distilled to afford 1.4 g 3-(N-isopropylamino) butan-2-ol 11 as a clear, colorless liquid (yield 67%).: $^1$H NMR (200 MHz, $CDCl_3$) δ3.80–3.96 (m, 1H, CHOH), 2.86–2.98 (m, 1H, MeCH), 2.56–2.75 (m, 2H, $NCH_2$), 1.24–1.60 (m, 2H, $CH_2$), 1.08 (d, J=6.1 Hz, 3H, Me), 0.98 (d, J=6.2 Hz, 6H, $Me_2$); $^{13}$C NMR (200 MHz, $CDCl_3$) δ69.5 (OCH), 48.6 ($NHCH_2$), 46.0 (NHCH), 37.2 ($CH_2$), 23.5, 22.9, 22.5; MS(EI) m/e 131 ([M$^+$], 10%), 116 (81), 98 (35), 72 (100), 58 (30), 56 (45), 44 (37); HRMS(EI) m/e calc'd for $C_7H_{17}ON$ [M$^+$]: 131.1310, found 131.1311; $[a]_D^{20}$=32.5° (c=0.21, chloroform).

Example 3

2R-Hydroxy-4-(N-tert-butyl)aminobutane (31)

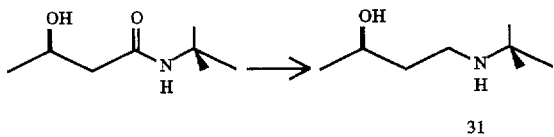

To a solution of 26.4 ml 1M (26.4 mmol) borane in THF was added 2.1 g (13.2 mmol) 3R-hydroxy-N-tert-butylbutanoamide in 20 ml THF at 0° C. under nitrogen. The solution was then brought to reflux and maintained there for one hour. The reaction mixture was cooled down to room temperature and 1N HCl was added slowly to quench the reaction. THF was removed in vacuo, and the aqueous solution was saturated with solid NaOH and then was extracted three times with a total 250 ml diethylether. The combined organic phase was dried, filtered and distilled to afford 398 mg 2R-hydroxy-4-(N-tert-butyl)aminobutane 31 as a clear, colorless liquid (yield 20.1%): $^1$H NMR (200 MHz, CDCl$_3$) δ3.80–3.92 (m, 1H, CHOH), 3.40–3.80 (b, 2H, OH, NH), 2.50–2.90 (m, 2H, NCH$_2$), 1.28–1.61 (m, 2H, CH$_2$), 1.07 (d, 3H, Me), 1.03 (s, 9H, Me$_3$)

Example 4

5'-O-(tert-butyldimethylsilyl) thymidine (1)

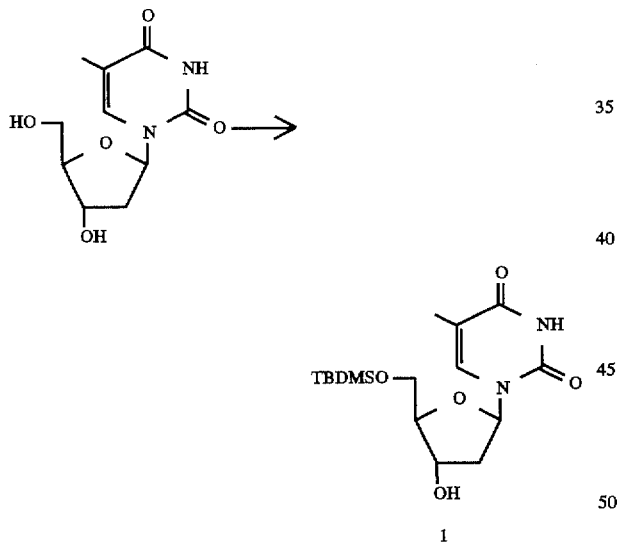

To a solution of 2.42 g (10 mmol) thymidine in 15 ml DMF was added 1.7 g (25 mmol) imidazole and 1.6 g (10.6 mmol) tert-butyldimethyl silyl chloride. The solution was stirred at room temperature for 3 hours. DMF was then removed in vacuo and the residue was dissolved in 150 ml of ethyl acetate. The solution was washed with water and the organic layer was dried over MgSO$_4$. After removing the solvent, the solid was recrystallized with ethyl acetate/pentane to obtain 2.5 g pure 5'-O-(tert-butyldimethylsilyl) thymidine 1 (70% yield).: m.p. 193°–194° C.; $^1$H NMR (500 MHz, CDCl$_3$) δ9.0 (s, 1H, NH), 7.50 (s, 1H, H-6), 6.36 (dd, J=5.8, 8.1 Hz, 1H, H-1'), 4.44 (m, 1H, H-3'), 4.03 (m, 1H, H-4'), 3.85 (m, 2H, H-5'), 2.66 (d, J=3.8 Hz, 1H, OH), 2.35 (m, 1H, H-2'), 2.07 (m, 1H, H-2'), 1.89 (s, 3H, C=CMe), 0.89 (s, 9H, CMe$_3$), 0.09 (s, 6H, SiMe$_2$); $^{13}$NMR (125 MHz, CDCl$_3$) δ163.8 (C-4), 150.4 (C-2), 135.4 (C-6), 110.9 (C-5), 87.2 (C-4'), 85.0 (C-1'), 72.6 (C-3'), 63.6 (C-5'), 41.1 (C-2'), 25.9 (SiCMe$_3$), 18.3 (SiCMe$_3$), 12.5 (C=CMe), −5.4 (SiMe$_2$), −5.5 (SiMe$_2$).

Example 5

5'-O-(4,4'-dimethoxytrityl) thymidine (16)

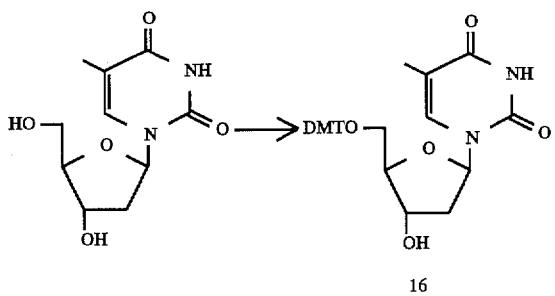

Triethylamine (10 ml) in 200 ml THF was injected into a solid mixture of 6.8 g (28.0 mmol) thymidine and 10.2 g (28.6 mmol) 4,4'-dimethoxytrityl chloride under nitrogen with stirring. The solution was stirred at room temperature for 2 hours. After completion of the reaction, 10 ml methanol was added to consume the excess DMTrCl. The mixture was stirred for 5 minutes and the solvent removed by rotary evaporation. The residue was dissolved in 250 ml of ethyl acetate and the solution was washed with saturated NaHCO$_3$ and dried over MgSO$_4$. The solid was recrystallized from ethyl acetate/hexane to obtain 13.0 g 5'-protected thymidine 16 (85.6%).: m.p. 124°–126° C.; $^1$H NMR (200 MHz, CDCl$_3$) δ8.97 (s, 1H, NH), 7.60 (m, 1H, H-6), 6.72–7.42 (m, 13H, Ph), 6.42 (m, 1H, H-1'), 4.56 (m, 1H, H-3'), 4.05 (m, 1H, H-4'), 3.78 (s, 6H, OMe$_2$), 3.41 (m, 2H, H-5'), 2.62 (m, 1H, OH), 2.46 (m, 2H, H-2'), 1.46 (s, 3H, Me); $^{13}$C NMR (50 MHz, CDCl$_3$) δ163.0 (C-4), 157.6, 149.8 (C-2), 143.5, 135.0 (C-6), 134.7, 134.6, 129.4, 127.4, 127.3, 126.5, 112.8, 110.9 (C-5), 86.7 (C-4'), 86.2, 84.7 (C-1'), 72.5 (C-3'), 63.8 (C-5'), 55.5 (OCH$_3$), 41.3 (C-2'), 12.5 (CH$_3$).

Example 6

5'-O-(4,4'-dimethoxytrityl)-3'-O-(tert-butyldimethlsilyl) thymidine (17)

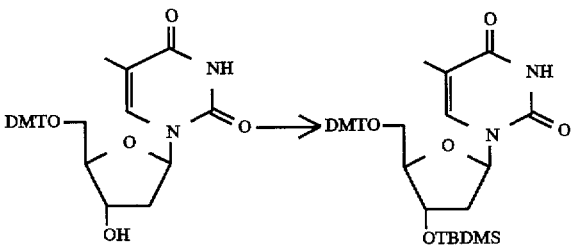

To a solution of 13.0 g (23.9 mmol) 5'-O-(4,4'-dimethoxytrityl)thymidine 16 in 50 ml DMF was added 3.0 g (44 mmol) imidazole and 3.6 g (23.9 mmol) tert-butyl-dimethylsilyl chloride. The solution was stirred at room temperature for 3 hours. DMF was then removed in vacuo and the residue was dissolved in 300 ml of ethyl acetate. The solution was washed with water and the organic layer was dried over $MgSO_4$. After concentration of the solution and recrystallization from ethyl acetate/hexane, the solid product 5'-O-(4,4'-dimethoxy)-3'-(tert-butyldimethylsilyl)thymidine 17 was used directly for the next reaction.

Example 7

3'-O-(tert-butyldimethylsilyl)thymidine (18)

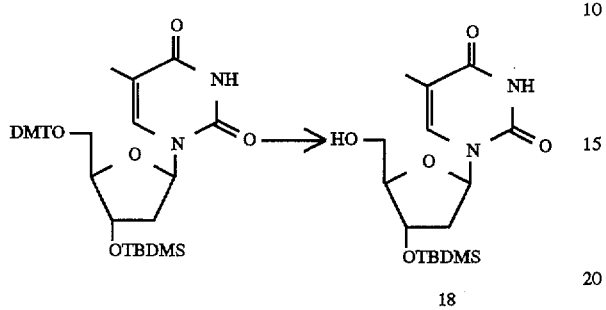

18

A solution of 5 g (7.6 mmol) 5'-O-(4,4'-dimethoxytrityl)-3'-O-(tert-butyldimethylsilyl) thymidine 17 in 100 ml 80% aq. acetic acid was stirred until the removal of dimethoxytrityl group was completed. Saturated $Na_2CO_3$ was then added to adjust the pH of the solution to 6–7. The solution was then extracted with ethyl acetate. The extract was dried and the mixture was chromatographed on a silica gel column ($CH_2Cl_2$:MeOH=20:1) to give 2.5 g of 3'-O-(tert-butyldimethylsilyl) thymidine 18 (92.6%).: m.p.93=20–95° C. (lit. 83°–84° C.); H NMR (200 MHz $CDCl_3$) δ9.18 (s, 1H, NH), 7.36 (b, 1H, H-6), 6.12 (t, J=6.8 Hz, 1H, H-1'), 4.44–4.48 (m, 1H, H-3'), 3.69–3.91 (m, 3H, H-4', H-5'), 2.87 (m, 1H, OH), 2.15–2.35 (m, 2H, H-2'), 1.87 (s, 3H, C=CMe), 0.86 (s, 9H, $CMe_3$), 0.05 (s, 6H, $SiMe_2$); $^{13}C$ NMR (125 MHz, $CDCl_3$) δ163.9 (C-4), 150.4 (C-2), 137.1 (C-6), 110.9 (C-5), 87.6 (C-4'), 86.8 (C-1'), 71.5 (C-3'), 61.9 (C-5'), 40.4 (C-2'), 25.7 ($SiCMe_3$), 17.9 (SiCMe), 12.5 (C=CMe), −4.7 ($SiMe_2$), −4.9 ($SiMe_2$).

Example 8

2-Chloro-3-iso-propyl-6R-methyl-1-oxa-3-aza-2-phosphacyclohexane (12)

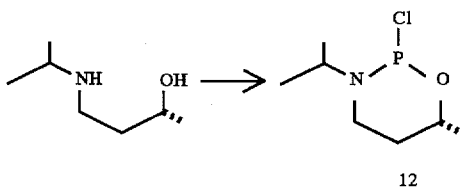

12

To a solution of 2.2 ml (3.45 g, 25 mmol) phosphorus trichloride in 30 ml dichloromethane was added a solution of 2.89 g (22 mmol) 2R-hydroxy-4-(N-iso-propyl) aminobutane 11 and 5.0 g (6.9 ml, 50 mmol) triethylamine in 20 ml dichloromethane with vigorous stirring under nitrogen at 0° C. Stirring was continued at room temperature for 0.5 hour. The solvent was removed by evaporation under reduced pressure and the residue was extracted with diethyl ether (3×50 ml). Distillation gave 2.9 g of product 12 (74.4% yield).: $^1$H NMR (200 MHz, $CDCl_3$) δ4.48–4.68 (m, 1H, OCH), 3.40–3.61 (m, 1H, NCH), 3.15–3.38 (m, 1H, $NCH_2$), 2.80–2.96 (m, 1H, $NCH_2$), 1.71–1.85 (m, 2H, $CH_2$), 1.25 (d, J=6.4 Hz, 3H, Me), 1.13 (dd, 6H, $Me_2$); $^{13}C$ NMR (50 MHz, $CDCl_3$) δ69.5 (d, J=4.3 Hz, OCMe), 49.6 (d, J=34 Hz, $NCMe_2$), 37.4 (d, J=5.5 Hz, $NCH_2$), 33.4 ($CH_2$), 22.2 (d, J=4.3 Hz, Me), 21.1 (d, J=13.3 Hz, $Me_2$), 19.2 (d, J=5.0 Hz, $Me_2$); $^{31}P$ NMR (81 MHz,$CDCl_3$) δ160.6.

Example 9

Phosphoramidite (13a)

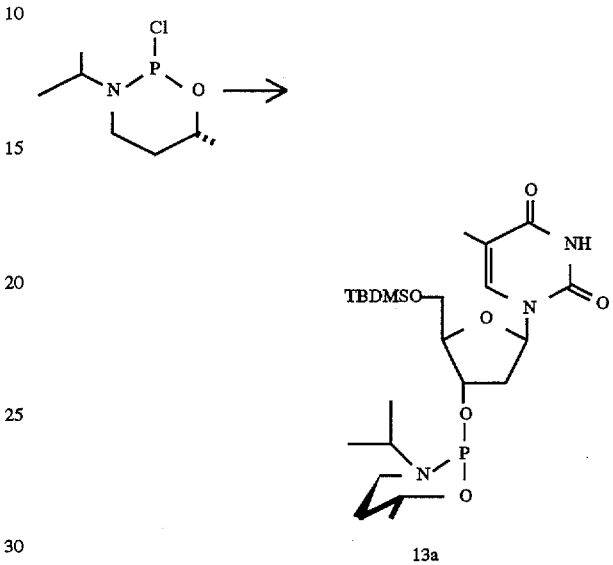

13a

To a solution of 215 mg (1.1 mmol) of 2-chloro-3-isopropyl-6R-methyl-1-oxa-3-aza-2-phosphacyclohexane 12 in 40 ml $CH_2Cl_2$ was added a solution of 356 mg (1.0 mmol) of 5-O-(tert-butyldimethylsilyl)thymidine and 0.154 ml triethylamine (111 mg, 1.1 mmol) in 20 ml $CH_2Cl_2$ with vigorous stirring under nitrogen at 0° C. The mixture was stirred at room temperature until TLC indicated that the reaction had gone to completion. The reaction mixture was transferred to 150 ml ethyl acetate, which was previously washed with a saturated $NaHCO_3$ solution. Saturated $NaHCO_3$ was then added to wash the solution. The separated organic phase was dried over $MgSO_4$. A white foam (quantitative yield) was formed after the solvent was removed by evaporation under reduced pressure. Two components were found from $^{31}P$ NMR spectra in a ratio of 1:3 (135.0 ppm: 133.6 ppm). The reaction mixture in $CDCl_3$ was then refluxed for about 4 hours to get a ratio of up to 1:12 (135.0 ppm: 133.6 ppm). After chromatography on a silica gel column (hexane:ethyl acetate:triethylamine=5:3:2), the fast eluting component (133.6 ppm) was separated as a pure diastereomer.: $^1$H NMR (500 MHz, $CDCl_3$) δ7.50 (m, 1H, H-6), 6.36 (dd, J=8.5, 5.8 Hz, 1H, H-1'), 4.56 (m, 1H, H-3'), 4.30 (m, 1H, HCMe), 4.04 (m, 1H, H-4'), 3.75–3.90 (m, 2H, H-5'), 3.39 (hept, J=6.3 Hz, 1H, NCH), 3.24 (m, 1H, $NCH_2$), 2.72 (m, 1H, $NCH_2$), 2.35 (m, 1H, H-2'), 2.06 (m, 1H, H-2'), 1.89 (d, J=0.9 Hz, 3H, $CH_3$), 1.64 (m, 2H, $CH_2$), 1.16 (d, J=6.4 Hz, 3H, OCHMe), 1.08 (dd, J=2.0 Hz, 6.3 Hz, 6H, $NCMe_2$), 0.89 (s, 9H, $SiCMe_3$), 0.09 (d, J=1.5 Hz, 6H, $SiMe_2$); $^{13}C$ NMR (125 MHz, $CDCl_3$) δ163.9 (C-4), 150.5 (C-2), 135.3 (C-6), 110.9 (C-5), 86.5 (d, J=2.8 Hz, C-4'), 84.8 (C-1'), 73.3 (d, J=19.2 Hz, C-3'), 66.0 (d, J=2.7 Hz, OCH), 63.2 (C-5'), 49.2 (d, J=34.8 Hz, NCH), 40.4 (d, J=4.6 Hz, C-2'), 36.6 (d, J=5.5 Hz, $NCH_2$), 34.6 ($CH_2$), 25.9 ($SiCMe_3$), 22.9 (d, J=4.6 Hz, OCMe), 21.8 (d, J=10 Hz, $NCMe_2$), 21.0 (d, J=4.6 Hz, $NCMe_2$), 18.3 ($SiCMe_3$), 12.5

(C=CMe), −5.5 (SiMe$_2$), −5.4 (SiMe$_2$); $^{31}$P NMR (81 MHz, CDCl$_3$) δ133.6; MS (CI, NH$_3$)) m/e 516 ([M+H$^+$],37%), 390 (21), 339 (92), 178 (100), 160 (55); HRMS (CI, NH$_3$) m/e calc'd for C$_{23}$H$_{43}$N$_3$O$_6$PSi [M+H$^+$]: 516.2659, found 516.2664

Example 10

Phosphoramidite (13b)

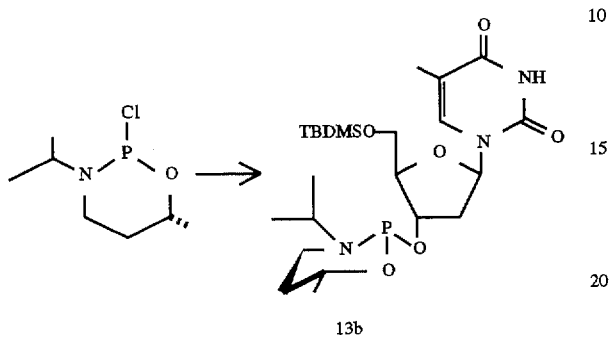

13b

To a solution of 215 mg (1.1 mmol) 2-chloro-3-isopropyl-6R-methyl-1-oxa-3-aza-2-phosphocyclohexane 12 in 40 ml CH$_2$Cl$_2$ was slowly added a solution of 356 mg (1.0 mmol) 5'-O-(tert-butyldimethylsilyl)thymidine 1 and 0.154 ml triethylamine (111 mg, 1.1 mmol) in 20 ml CH$_2$Cl$_2$ with vigorous stirring under nitrogen at −78° C. The mixture was stirred at −78° C. until TLC indicated that the reaction had gone to completion. The reaction mixture was quickly transferred to 150 ml ethyl acetate, which was previously washed with a cold saturated NaHCO$_3$ solution. Cold saturated NaHCO$_3$ was then added to wash the solution. The separated organic phase was dried over MgSO$_4$. A white foam (quantitative yield) was formed after the solvent was removed by evaporation under reduced pressure at 0° C. Two components were found from $^{31}$P NMR spectra in a ratio of 5:1 (135.1 ppm:133.6 ppm). The reaction mixture in CDCl$_3$ was immediately chromatographed on a silica gel column (hexane:ethylacetate:triethylamine=5:3:2) and the slow eluting component (135.1 ppm) was separated as an enriched diastereomer (92% pure).: $^1$H NMR (500 MHz, CDCl$_3$) δ7.48 (m, 1H, H-6), 6.32–6.35 (dd, J=5.4, 7.8 Hz, 1H, H-1'), 4.55–4.60 (m, 1H, H-3'), 4.02–4.10 (m, 1H, OCH), 4.00 (m, 1H, H-4'), 3.74–3.89 (m, 2H, H-5'), 3.36–3.45 (m, 1H, NCH), 3.09–3.14 (m, 1H, NCH$_2$), 2.85–2.93 (m, 1H, NCH$_2$), 2.40–2.44 (m, 1H, H-2'), 2.12–2.21 (m, 1H, CH$_2$), 2.00–2.06 (m, 1H, H-2'), 1.88 (s, 3H, C=CCH$_3$), 1.81–1.86 (m, 1H, CH$_2$), 1.28 (d, J=6.3 Hz, 3H, OCMe), 1.11 (dd,J=6.3, 11.7 Hz, 6H, NCMe$_2$), 0.89 (s, 9H, Me$_3$), 0.08 (d, J=2.0 Hz, 6H, SiMe$_2$); $^{13}$C NMR (125 MHz, CDCl$_3$) δ163.7 (C-4), 150.2 (C-2), 135.5 (C-6), 110.8 (C-5), 87.0 (d, J=6.4 Hz, C-4'), 84.8 (d, J=5.5 Hz, C-1'), 72.8 (d, J=19.2 Hz, OCHMe), 70.3 (d, 7.3, C-3'), 63.1 (C-5'), 49.5 (d, J=39.4 Hz, NCHMe$_2$), 40.1 (d, J=1.8 Hz, C-2'), 36.9 (d, J=5.5 Hz, NCH$_2$), 31.5 (d, J=7.3 Hz, CH$_2$), 25.9 (SiCMe$_3$), 23.3 (OCMe), 21.7 (d, J=11.0 Hz, NCHMe$_2$), 21.1 (d, J=5.5 Hz, NCHMe$_2$), 18.4 (SiCMe$_2$), 12.5 (C=CMe), −5.4 (SiMe$_2$), −5.5 (SiMe$_2$); $^{31}$P NMR (81 MHz, CDCl$_3$) δ135.1

Example 11

Phosphoramidite (14)

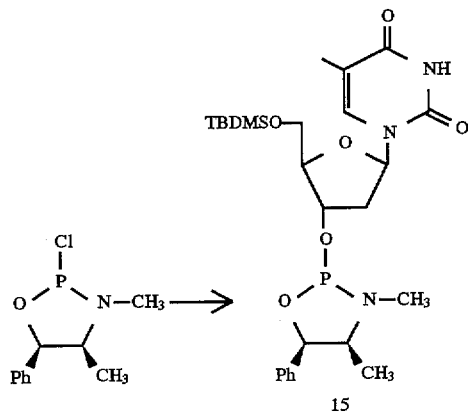

15

To a solution of 0.2 ml (315 mg, 2.3mmol) phosphorus trichloride in 10 ml dichloromethane was added a solution of 320 mg (2.2 mmol) butanol 31 and 0.7 ml triethylamine in 5 ml dichloromethane with vigorous stirring under nitrogen at 0° C. and then at room temperature for 0.5 hour. The solvent was removed by evaporation under reduced pressure and the residue was extracted with diethyl ether (2×40 ml). After removing the ether, 512 mg residual oil was obtained. Then 209 mg (1.0 mmol) of this residual oil was dissolved in 10 ml dichloromethane, a solution of 200 mg (0.56 mmol) 5'-O-(tert-butyldimethylsilyl)thymidine 1 and 0.16 ml triethylamine (11 mmol) in 10 ml CH$_2$Cl$_2$ was added with vigorous stirring under nitrogen at room temperature. The mixture was stirred at room temperature until TLC indicated that the reaction had gone to completion. The reaction mixture was transferred to 100 ml ethyl acetate, which was previously washed with saturated NaHCO$_3$ solution. Saturated NaHCO$_3$ and then water was added to wash the solution. The separated organic phase was dried over MgSO$_4$. A white foam (quantitative yield) was formed after the solvent was removed by evaporation under reduced pressure. Two components were found from $^{31}$P NMR spectra in a ratio of 1:5 (132.4 ppm:130.8 ppm). The reaction mixture in C$_6$D$_6$ was then refluxed for about 4 hours to get a ratio of up to 1:9 (d 137.8 ppm:136.1 ppm in benzene).

Example 12

Phosphoramidite (15)

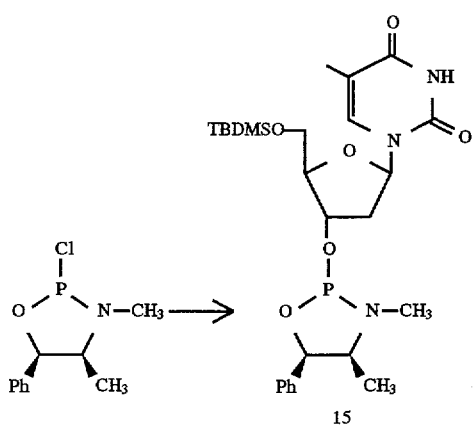

To a solution of 6.30 g (4.0 ml, 46 mmol) phosphorus trichloride in 100 ml dichloromethane was added a solution of 6.61 g (40 mmol) (1R,2S) ephedrine and 10.1 g (14 ml, 100 mmol) triethylamine in 50 ml dichloromethane with vigorous stirring under nitrogen at 0° C. and then at room temperature for 0.5 hour. The solvent was removed by evaporation under reduced pressure and the residue was extracted with diethyl ether (3×100 ml). After removing the ether, 9.3 g residual oil was obtained. Then 345 mg (1.5 mmol) of this residual oil was dissolved in 40 ml dichloromethane, a solution of 356 mg (1.0 mmol) 5'-O-(tert-butyldimethylsilyl)thymidine 1 and 0.154 ml triethylamine (111 mg, 1.1 mmol) in 20 ml $CH_2Cl_2$ was added with vigorous stirring under nitrogen at −78° C. The mixture was stirred at −78° C. until TLC indicated that the reaction had gone to completion. The reaction mixture was quickly transferred to 150 ml ethyl acetate, which was previously washed with cold saturated $NaHCO_3$ solution. Cold saturated $NaHCO_3$ was added to wash the solution. The separated organic phase was dried over $MgSO_4$. A white foam (quantitative yield) was formed after the solvent was removed by evaporation under reduced pressure at 0° C. Two components were found from the $^{31}P$ NMR spectrum in a ratio of 1:2 (147.3 ppm:141.6 ppm). The reaction mixture in $CDCl_3$ was then refluxed for about 4 hours to get a ratio of up to 1:5 (151.5 ppm:143.5 ppm). After chromatography on silica gel column (hexane:ethyl acetate:triethylamine= 5:3:2), the slow eluting component (143.5 ppm) was separated as a pure diastereomer.: $^1H$ NMR (500 MHz, $CDCl_3$) δ7.23–7.50 (m, 5H, Ph), 6.35 (m, 1H, H-1'), 5.60 (d, J=6.8 Hz, 1H, PhCH), 4.71–4.75 (m, 1H, H-5'), 4.01–4.02 (m, 1H, H-4'), 3.78–3.87 (m, 2H, H-5'), 3.52–3.58 (m, 1H, MeCH), 2.64 (d, J=2.2 Hz, 3H, NMe), 2.31–2.36 (m, 1H, H-2'), 2.05–2.11 (m, 1H, H-2'), 1.90 (s, 3H, C=CMe), 0.90 (s, 9H, $CMe_3$), 0.60 (d, J=6.4 Hz, 3H, CHMe), 0.09 (s, 6H, $SiMe_2$); $^{13}C$ NMR (125 MHz, $CDCl_3$) δ163.9 (C-4), 150.5 (C-2), 137.9 (Ph), 135.3 (C-6), 128.1 (Ph), 127.7 (Ph), 126.7 (Ph), 111.0 (C-5), 86.7 (d, J=1.8 Hz, C-4'), 84.7 (OCPh), 84.6 (d, J=9.2 Hz, C-1'), 73.1 (d, J=18.3 Hz, C-3'), 63.0 (C-5'), 57.5 (d, J=5.6 Hz, NCMe), 40.6 (d, J=5.5 Hz, C-2'), 28.8 (d, J=17.4, $NCH_3$), 25.9 ($SiCMe_3$), 18.3 ($SiCMe_3$), 14.6 (d, J=3.7 Hz, NCHMe), 12.5 (C=CMe), −5.4 ($SiMe_2$), −5.5 ($SiMe_2$); $^{31}P$ NMR (81 MHz, $CD_3CN$) δ143.5

Example 13

Phosphite triester (20a) from phosphoramidite 13a with MeOH

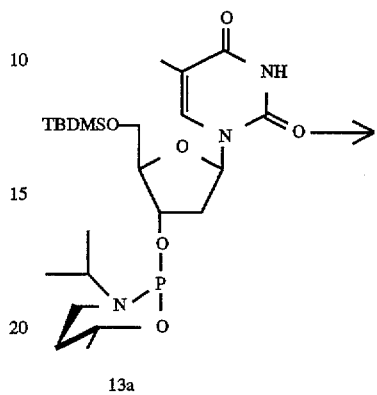

Diastereomeric pure phosphoramidite 13a (10 mg, fast eluting component) in 0.5 ml $CDCl_3$ was put in 5 mm NMR tube, and 50 µl of dry MeOH (a large excesses) was then added by syringe, followed by 1 mg of dicyanoimidazole. The reaction was monitored by $^{31}P$ NMR until the reaction went to completion. The phosphite triesters formed in a ratio of 10:1 (139.4 ppm:138.8 ppm) and were purified on a silica gel column.: $^1H$ NMR (500 MHz, $CDCl_3$) δ7.48 (s, 1H, H-6), 6.35 (dd, J=5.4, 8.8 Hz, 1H, H-1'), 4.78–4.82 (m, 1H, H-3'), 4.24–4.33 (m, 1H, OCH), 4.10 (d, J=2.4 Hz, 1H, H-4'), 3.76–3.89 (m, 2H, H-5'), 3.50 (d, J=10.7 Hz, 3H, $CH_3$), 2.78 (m, 1H, NCH), 2.65 (m, 2H, $NCH_2$), 2.40 (m, 1H, H-2'), 2.04 (m, 1H, H-2'), 1.89 (d, J=1.0 Hz, 3H, C=C—$CH_3$), 1.64–1.78 (m, 2H, $OCHCH_2$), 1.25 (d, J=6.4 Hz, 3H, $OCHCH_3$), 1.03 (d, J=6.3 Hz, 6H, $NCHMe_2$), 0.91 (s, 9H, $SiMe_3$), 0.10 (d, J=2.0 Hz, 6H, $SiMe_2$); $^{13}C$ NMR (125 MHz, $CDCl_3$) δ163.5 (C-4), 150.1 (C-2), 135.3 (C-6), 110.9 (C-5), 86.5 (d, J=2.7 Hz, C-4'), 84.8 (C-1'), 72.1 (d, J=8.2 Hz, C-3'), 69.5 (OCH), 63.0 (C-5'), 49.2 (d, J=9.2 Hz, $OCH_3$), 48.8 ($Me_2CNH$), 40.3 (d, J=3.7 Hz, C-2'), 38.7 (d, J=4.6 Hz, $CH_2$), 25.9 ($SiCMe_3$) 22.9 (d, J=3.7 Hz, $NCHMe_2$) 18.3 ($SiCMe_2$), 12.5 (C=CMe), −5.4 ($SiMe_2$); $^{31}P$ NMR (121 MHz, $CDCl_3$) δ139.4

Example 14

Phosphite triester (20b) from Phosphoramidite 13b with Methanol

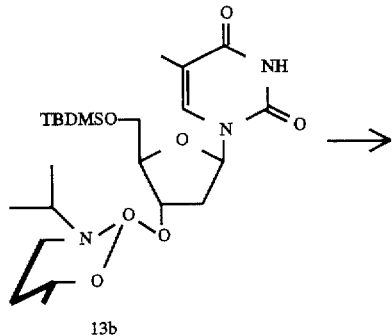

Example 15

Phosphite triester (32) from Phosphoramidite 13a with n-Butanol

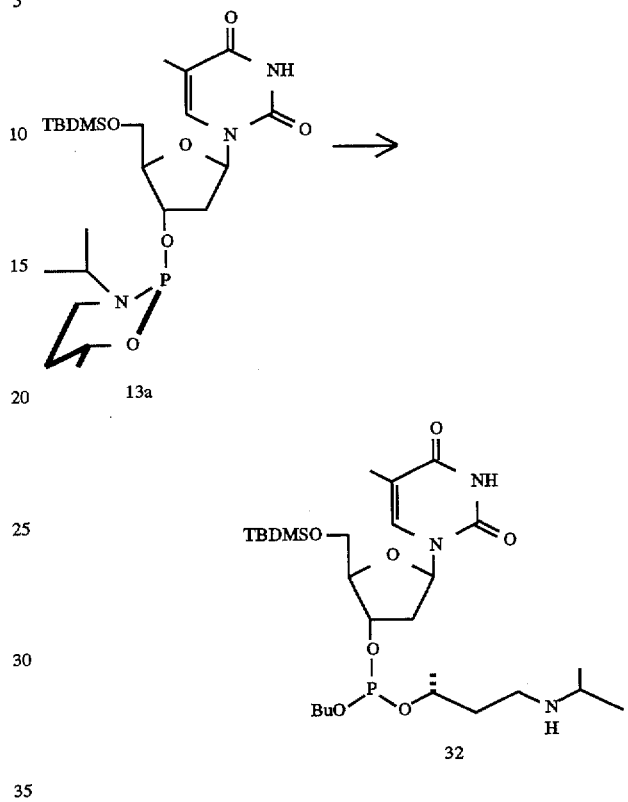

Diastereomeric enriched (75%) phosphoramidite 13b (10 mg, slow eluting component) in 0.5 ml CDCl$_3$ was put in 5 mm NMR tube, and 50 μl dry MeOH (a large excess) was then added by syringe, followed by 1 mg of dichloroimidazole. The reaction was monitored by $^{31}$P NMR until the reaction went to completion. The phosphite triesters formed in a ratio of 1:2 (139.4 ppm:138.8 ppm) were purified on a silica gel column. $^1$H NMR (500 MHz, CDCl$_3$) δ7.48 (s, 1H, H-6), 6.34 (m, 1H, H-1'), 4.78–4.82 (m, 1H, H-3'), 4.25–4.33 (m, 1H, OCH), 4.11 (d, J=2.4 Hz, 1H, H-4'), 3.77–3.89 (m, 2H, H-5'), 3.49 (d, J=10.3 Hz, 3H, CH$_3$), 2.76 (m, 1H, NCH), 2.64 (m, 2H, NCH$_2$), 2.39 (m, 1H, H-2'), 2.05 (m, 1H, H-2'), 1.90 (s, 3H, C═C—CH$_3$), 1.65–1.78 (m, 2H, OCCH$_2$), 1.26 (d, J=6.4 Hz, 3H, OCHCH$_3$), 1.04 (d, J=6.4 Hz, 6H, NCHMe$_2$), 0.91 (s, 9H, SiCMe$_3$), 0.10 (d, J=2.0 Hz, 6H, SiMe$_2$); $^{31}$P NMR (121 MHz, CDCl$_3$) δ138.8

Diastereomerically pure phosphoramidite 13a (10 mg, fast eluting component) in 0.5 ml CDCl$_3$ was placed in 5 mm NMR tube, and 50 μl dry n-butanol (a large excess) was then added by syringe, followed by 1 mg of dicyanoimidazole. The reaction was monitored by $^{31}$P NMR until the reaction went to completion. The phosphite triesters formed in a ratio of 7:1 (138.9 ppm:138.5 ppm) were purified on a silica gel column.$^1$NMR (500 MHz, CDCl$_3$) δ7.49 (d, J=1.5 Hz, 1H, H-6), 6.35 (dd, J=5.5, 8.8 Hz, 1H, H-1'), 4.83 (m, 1H, H-3'), 4.24–4.31 (m, 1H, OCH), 4.11 (d, J=2.0 Hz, 1H, H-4'), 3.71–3.89 (m, 4H, 2H-5', OCH$_2$), 2.78 (m, 1H, NCH), 2.66 (m, 2H, NCH$_2$), 2.39 (m, 1H, H-2'), 2.02 (m, 1H, H-2'), 1.89 (s, 3H, C═C—CH$_3$), 1.63–1.77 (m, 2H, OCMeCH$_2$), 1.57 (m, 2H, CH$_2$), 1.36 (m, 2H, CH$_2$), 1.24 (d, J=6.3 Hz, 3H, OCHCH$_3$), 1.04 (d, J=6.3 Hz, 6H, NCHMe$_2$), 0.91 (s, 9H, SiCMe$_3$), 0.10 (d, J=2.0 Hz, 6H, SiMe$_2$); $^{31}$P NMR (121 MHz, CDCl$_3$) δ138.9.

Example 16

Phosphite triester (33a) from phosphoramidite 7a with Methanol

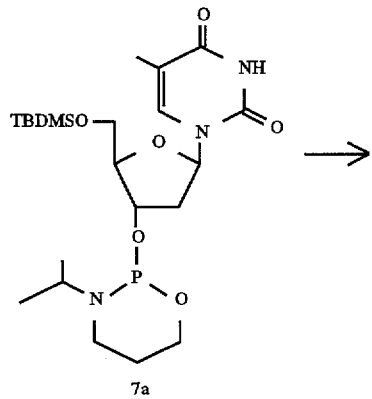

7a

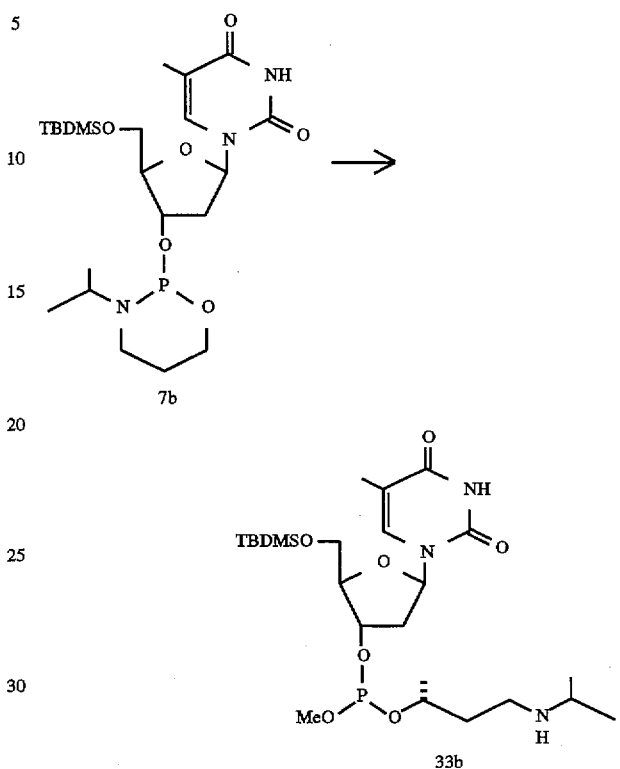

33a

Diastereomerically pure phosphoramidite 7a (10 mg, fast eluting component) in 0.5 ml CDCl₃ was put in 5 mm NMR tube, and 50 µl dry methanol (a large excess) was then added by syringe, followed by 1 mg of 4,5-dicyano-2-bromoimidazole. The reaction was monitored by $^{31}$P NMR until the reaction went to completion. The phosphite triester consisted of only one diastereomer (139.1 ppm) and was purified on a silica gel column. $^{1}$H NMR (500 MHz, CDCl₃) δ7.48 (s, 1H, H-6), 6.34 (dd, J=5.4, 8.8 Hz, 1H, H-1), 4.78 (m, 1H, H-3'), 4.09 (m, 1H, H-4'), 3.76–3.89 (m, 4H, 2H-5', OCH₂), 3.50 (d, J=10.2 Hz, 3H, OCH₃), 2.80 (m, 1H, NCHMe₂), 2.67 (t, J=6.8 Hz, 2H, NHCH₂), 2.39 (m, 1H, H-2'), 2.05 (m, 1H, H-2'), 1.90 (s, 3H, C=C—CH₃), 1.78 (m, 2H, OCHCH₂), 1.03 (d, J=6.3 Hz, 6H, NCHMe₂), 0.91 (s, 9H, SiCMe₃), 0.10 (s, 6H, SiMe₂); $^{31}$P NMR (121MHz, CDCl₃) δ139.1; MS(CI) m/e: 534 ([M+H⁺], 100%), 502 (14.4), 376 (13.6), 339 (74.6), 281 (20.4), 164 (59.8)

Example 17

Phosphite triester (33b) from phosphoramidite 7b with Methanol

Diastereomerically enriched (92%) phosphoramidite 7b (10 mg, slow eluting component) in 0.5 ml CDCl₃ was placed in 5 mm NMR tube, and 50 µl dry methanol (a large excess) was then added by syringe, followed by 1 mg of dicyanobromoimidazole. The reaction was monitored by $^{31}$P NMR until the reaction went to completion. Diastereomerically enriched phosphite triester 33b (92%) in a ratio of 1:11 (139.2 ppm:138.8 ppm) was purified on a silica gel column. $^{31}$P NMR (121 MHz, CDCl₃) δ138.8

Example 18

Thiophosphonate (44)

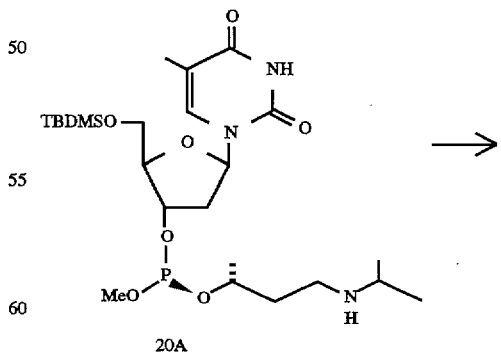

20A

43
-continued

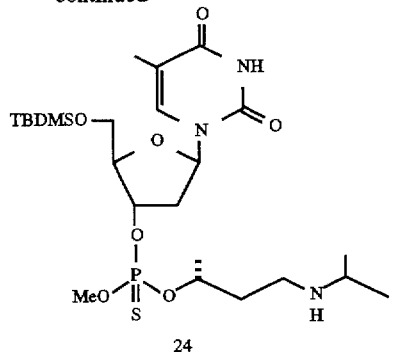

24

Diastereomerically pure 13a (100 mg, fast eluting component) was dissolved in 5 ml CDCl$_3$, and 0.5 ml MeOH was then added by syringe, followed by 5 mg of 2-bromo-4,5-dicyanoimidazole. The reaction was monitored by $^{31}$P NMR until the reaction went to completion with almost only one diastereomer of phosphite triester 20a (139.4 ppm) being found, and then 10 mg sulfur was added. Within 5 minutes, the sulfurization went to completion. After chromatography (ethyl acetate:triethylamine=1:1), sulfurized product 24 was obtained in an oily form. $^1$H NMR (500 MHz, CDCl$_3$) δ7.50 (d, J=1.4 Hz, 1H, H-6), 6.36 (dd, J=5.4, 9.3 Hz, 1H, H-1'), 5.08 (m, 1H, H-3'), 4.63–4.72 (m, 1H, OCH), 4.25 (m, 1H, H-4'), 3.88 (m, 2H, H-5'), 3.73 (d, J=13.7 Hz, 3H, OCH$_3$), 2.77 (m, 1H, NCHMe$_2$), 2.67 (t, J=6.4 Hz, 2H, NCH$_2$), 2.48 (m, 1H, H-2'), 2.09 (m, 1H, H-2'), 1.90 (d, J=1.5 Hz, 3H, C=C—CH$_3$), 1.70–1.86 (m, 2H, OCCH$_2$), 1.32 (d, J=5.9 Hz, 3H, OCHCH$_3$), 1.04 (dd, J=2.9, 5.9 Hz, 6H, NCHMe$_2$), 0.92 (s, 9H, SiCMe$_3$), 0.12 (s, 6H, SiMe$_2$); $^{31}$P NMR (121 MHz, CDCl$_3$) δ67.5

Example 19

2-Bromo-4,5-dicyanoimidazole (21)

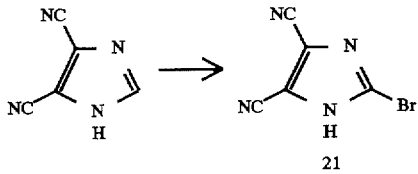

To 1.18 g (10 mmol) 4,5-dicyanoimidazole and 25 ml 0.1M NaOH was added 1.8 ml Br$_2$ (35 mmol). The mixture was stirred overnight at room temperature and then acidified with dilute HCl. The solid was filtered, rinsed with water and recrystallized from water to give 1.5 g of dicyanobromoimidazole 21 (yield 76.4%).: m.p. 147°–149° C. (lit. 141°–143° C.); Rf=0.65 (ethyl acetate:methanol=4:1); MS(EI): 198( [M+2], 96%), 196 ([M$^+$], 100%),171 (28.5), 169 (29.2), 117 (27.4), 91 (19.0), 64 (20.6), 53 (22.4), 38 (18.8).

Example 20

Synthesis of (S)-methyl-3-(5-imidazolyl)-2-hydroxypropionate (3) hydrochloride

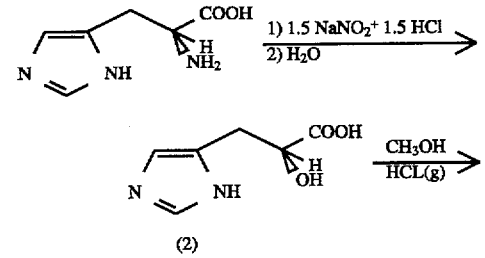

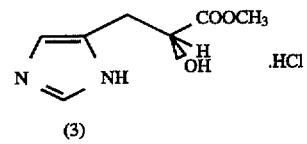

(3)

(L)-Histidine (3.103 g, 20 mmol) was first dissolved in 30 ml of 1N hydrochloric acid solution. This solution was cooled down to 0° C., then a solution of sodium nitrite (2.070 g, 30 mmol) in 10 ml distilled water was added dropwise over a period of 1 hour. The solution was stirred overnight at 0° C., then evaporated to dryness in vacuo with heating. 20 ml of distilled water was added to the solid residue, the mixture was evaporated once more with toluene in order to azeotropically remove the water residue as much as possible. After drying the compound in high vacuum overnight and without isolation of the intermediate acid, the mixture was dissolved into 50 ml of dry methanol and stirred under Ar. This solution was cooled down to 0° C. and a stream of gaseous hydrogen chloride was bubbled through the mixture. After 1.5 hours, TLC indicated disappearance of the acid and the reaction was stopped. The mixture was evaporated in vacuo with heating to yield a sticky yellow solid that could be crystallized from a mixture of ethanol and ether to yield 3.10 g of (2).HCl, m.p. 139°–142° C., [α]$_D$= 21° (c 1.9 methanol, 25° C.) (litt. -22°) $^1$HNMR (200 MHz, CD$_3$OD) δ8.90 (s, 1H, NCHN); 7.30 (s, 1H, NCHC); 4.40 (dd, ABX, $^3J_{Ha-Hx}$=5.40 Hz, $^3J_{Hb-Hx}$=5.00 Hz, CHOH); 3.72 (s, 3H, OCH$_3$); 2.85–3.10 (ABX, 2H, $^2J_{Ha-Hb}$=13.75 Hz, $^3J_{Hb-Hx}$=5.0 Hz, $^3J_{Ha-Hx}$=5.4 Hz, CH$_2$); $^{13}$C NMR (non decoupled) (125 MHz, D$_2$O) δ175.3 (s,CO); 134.2 (d, NCHN); 129.7 (s, CH$_2$CN); 117.6 (d, CCHN); 69.9 (d, CHOH); 53.6 (q, CH$_3$); 29.5 (t,CH$_2$); M.S. (M+1)$^+$.171

Example 21

Synthesis of imidazo-oxazaphospholidine (4)

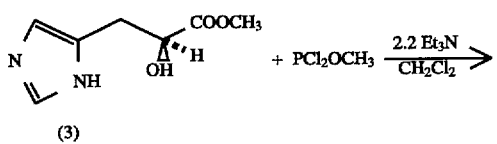

(3)

-continued

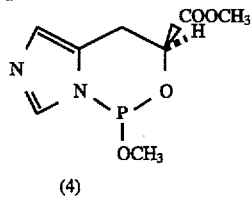

In scrupulously dry glassware, compound (3) (0.236 g, 1.39 mmol) was added and dried in vacuo overnight, then put under an atmosphere of Ar. This compound was suspended into 5 ml of dry ether, then triethylamine (0.20 ml, 3.15 mmol) was added. The suspension was cooled down to 0° C. and stirred under Ar. Then, methyl dichlorophosphite (0.15 ml, 1.58 mmol) was syringed into the mixture quickly. As soon as the phosphite was introduced, a thick white precipitate was observed, corresponding to the formation of triethylammonium chloride. After 15 min, $^{31}$P NMR showed several signals between 176 and 120 ppm, as well as after 2 to 4 hours. After overnight stirring at room temperature, $^{31}$P NMR showed a single signal at 143.5 ppm. Compound decomposed upon trying to handle it (dilution in dry ether, filtration in an Ar atmosphere, concentration by evaporation of the ether) as indicated by $^{31}$P NMR by several peaks at 5–20 ppm, corresponding most likely to H-phosphonates derivatives. Changing the reaction conditions did not bring any improvement. Therefore, compound (4) could not be further purified and analyzed.

Example 22

Synthesis of 1-tritylimidazole (5)

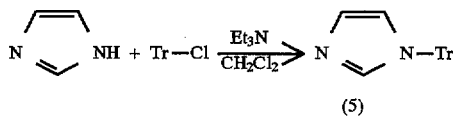

To a solution of trityl chloride (5.58 g, 20.0 mmol.) in dry methylene chloride (100 ml) cooled down to 0° C. and stirred under Ar, was added dropwise over 1.5 hours a solution of imidazole (1.36 g, 20.0 mmol.) and triethylamine (2.7 mml, 20 mmol) in 50 ml dry methylene chloride. At the end of the addition, the reaction mixture was allowed to warm up to room temperature and stirred under Ar at that temperature overnight. The reaction mixture was then washed with 20 ml of a 10% solution of ammonium chloride, then with 20 ml of distilled water. The organic phase was dried over magnesium sulfate and evaporated in vacuo to yield quantitatively a white solid. Recrystallization from methylene chloride/hexanes yielded 5.60 g of (5) (yield=90% after recrystallization). m.p. 214° C.; $^1$H NMR (200 MHz, CDCl$_3$) δ7.43 (m, 1H, NCHN), 7.3–7.4 (m, 9H, 3×C$_6$H$_5$), 7.1–7.2 (m, 6H, 3×C$_6$H$_5$), 7.0 (m, 1H, Ph$_3$CNCH=CH), 6.81 (m, 1H, Ph$_3$CNCH=CH); $^{13}$C NMR (50 MHz, CDCl$_3$) δ142.3, 139.0, 129.6, 128.2, 128.3, 121.6.

Example 23

Synthesis of (S)-1-(2-(1-triphenylmethyl)-imidazolyl)-propan-2-ol (s)-(6)

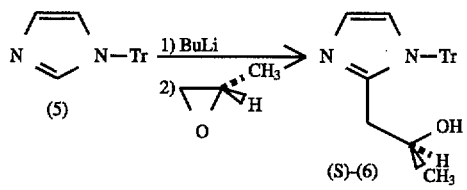

To a solution of N-tritylimidazole (1.55 g, 5 mmol) in freshly distilled THF (50 ml) cooled down to –78° C. and stirred under dry Ar, was added a 2.5M solution of n-butyllithium in pentane (2.4 ml, 6 mmol). The addition lasted for 30 min, and the deep red solution obtained was allowed to warm up to 0° C., stirred at room temperature for 1 hour, then cooled down again to –78° C. At that temperature, (S)-propylene oxide (0.35 g, 6 mmol) was added dropwise. After 30 min, the solution was allowed to warm up to 0° C. and was stirred at that temperature for 12 hours until TLC indicated that the reaction did not further proceed. The solution was poured into 50 ml of saturated NH$_4$Cl solution, and the resulting mixture was extracted with CH$_2$Cl$_2$. After flash chromatography (hexane:acetone:triethylamine 78:21:1), 1.44 g of the pure product was collected in 78% yield: m.p. 201° C.; $^1$H NMR (200 MHz, CDCl$_3$) δ7.20–7.40 (m, 9H, 3×C$_6$H$_5$), 7.10–7.18 (m, 6H, 3×C$_6$H$_5$), 6.90 (d, 1H, $^3J_{H\text{-}H}$=1.2; CHNCPh$_3$) 6.71 (d, 1H, $^3J_{H\text{-}H}$=1.2; CH=CHNCPh$_3$), 5.83 (b, 1H, OH), 3.40–3.60 (m, 1H, CHCH$_3$), 1.78–2.05 (ABX, 2H, $^3J_{Hb\text{-}Hx}$= 3.2 Hz, $^3J_{Ha\text{-}Hx}$=8.5 Hz, $^2J_{Ha\text{-}Hb}$=16.2 Hz, CH$_2$), 0.81 (d, $^3J_{H\text{-}H}$=6.0 Hz, 3H CH$_3$); $^{13}$C NMR (50 Mhz, CDCl$_3$) δ 149.2, 142.1, 129.6, 127.9, 127.7, 124.7, 121.0 (NCCN), 74.6, 65.0 (CHOH), 38.1 (CH$_2$), 22.3 (CH$_3$).

Example 24

Synthesis of (S)-1-(2-imidazolyl)-propan-2-ol (S)-(7)

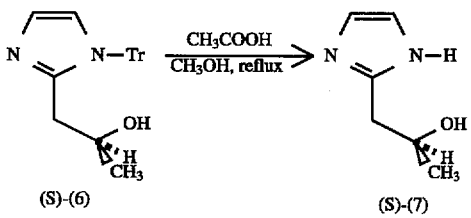

A solution of N-tritylimidazolylpropanol (S)-(6) (2.39 g, 6.51 mmol) in 80 ml methanol containing 4.3 ml glacial acetic acid (5%) was refluxed for about 12 hours. After that time, TLC indicated disappearance of the starting materials. The mixture was concentrated in vacuo and a white precipitate appeared upon addition of 50 ml of cold distilled water. The mixture was chilled, then filtered, and the white precipitate was washed with cold distilled water (10 ml). The filtrate was then evaporated twice, and the residual yellow oil redissolved in 50 ml dry methanol and passed through the weakly basic anion exchange resin (hydroxide form) IRA-68. The solution was then evaporated to yield a solid residue that could be recrystallized from a mixture of methanol and ethyl acetate. yield: 0.80 g, 98% of pure (S)-(7). m.p. 119°–121° C.; $^1$H NMR (200 Mhz, CD$_3$OD) δ6.96 (s, 2H, NCHCHN); 3.96 (m, 1H, CHCH$_3$); 2.4–2.65 (ABX, $^3J_{Hz-Hx}$=6.3 Hz, $^3J_{Hb-Hx}$=6.7 Hz, $^3J_{Ha-Hb}$=14.5Hz, CH$_2$); 0.87 (d, 3H, $^3J_{H-H}$=6.3 Hz, CH$_3$); $^{13}$C NMR (50 MHz, CD$_3$OD) δ145.8 (s, CH2CNH); 121.2 (d, NCH=CHNH); 67.1 (d, CHOH); 38.4 (t, CH2); 23.1 (q, CH$_3$); MS (CI): [M+1]$^+$.127

Example 25

Synthesis of 1-methoxy-3-methyl-imidaze-[2,1-e]-(3,4-dihydro)oxazaphosphorine (8)

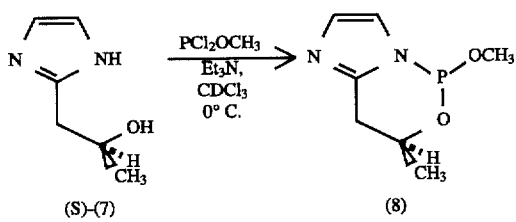

In an NMR tube previously dried in vacuo and under Ar was introduced 23.0 mg (0.20 mmol) of (S)-(2-imidazolyl)-propan-2-ol (S)-(7), then the tube was sealed with a septum and flushed with Ar. CDCl$_3$ (0.7 ml) was then introduced, followed by 127 µl (1.0 mmol) of triethylamine. The alcohol did not dissolve, and this suspension was cooled down to 0° C. while shaking the tube. At that temperature, 18.9 µl (0.20 mmol) of methyl dichlorophosphite was syringed inside the tube. Upon shaking, the alcohol dissolved instantaneously, and an exothermic reaction was noticed. After about 1 hour, $^{31}$P NMR revealed the presence of several peaks around 120–140 ppm. After about 3 hours, a single product (8) was observed by $^{31}$P NMR, as evidenced by its chemical shift at 118.8 ppm. There was no further characterization of this compound, as all efforts to isolate it have been unsuccessful and have led to the hydrolysis of this extremely water sensitive bicyclic structure, most likely to the corresponding H-phosphonate.

Example 26

Synthesis of 1-ethoxy-3-methyl-imidazo-[2,1-e]-(3,4-dihydro)oxazaphosphorine (9)

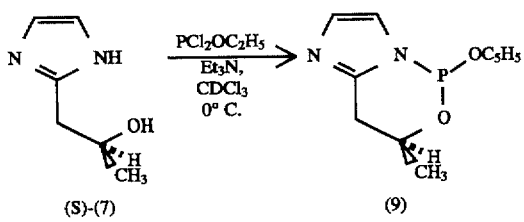

To an NMR tube previously dried in vacuo and under Ar, was introduced 18.9 mg (0.15 mmol) of (S)-(2-imidazolyl)-propan-2-ol (S)-(7). The tube was then sealed with a septum and flushed with Ar. Then, 0.7 ml CDCl$_3$ was introduced, followed by 105 µl (0.75 mmol) of triethylamine. The alcohol did not dissolve, and this suspension was cooled down to 0° C. while shaking the tube. At that temperature, 17.2 µl (0.15 mmol) of ethyl dichlorophosphite was syringed into the NMR tube. Upon shaking, the alcohol dissolved instantaneously, and an exothermic reaction was noticed. After about 2 hours, a single product was observed by $^{31}$P NMR as evidenced by its chemical shift at 118.2 ppm. After about 1 hour, the presence of other products around 120–140 ppm was noticed, one of which (121.1 ppm) is probably the other diastereomer. There was no further characterization of this compound.

Example 27

Synthesis of thiophosphate ethyl (S)-1-(2-imidazolyl)-prop-2-yl isopropyl ester (22)

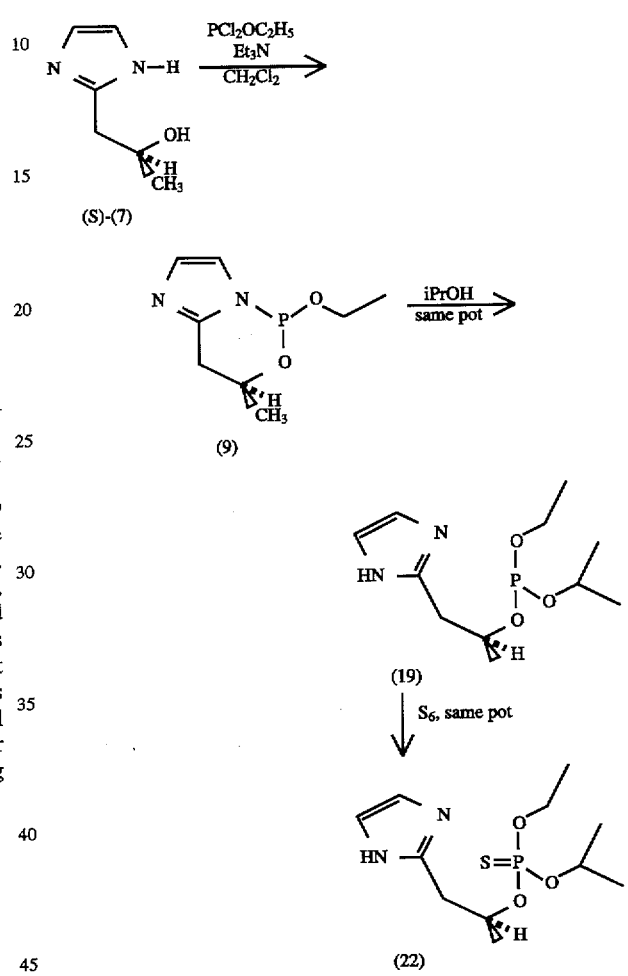

In an NMR tube, to a suspension of 18.9 mg (0.15 mmol) (S)-1-(2-imidazolyl)-propan-2-ol (S)-(7) in 0.7 ml dry deuterated chloroform and 0.21 ml triethylamine (1.5 mmol), shaken at room temperature under Ar was introduced with a syringe 17.2 µl (0.15 mmol) of ethyl dichlorophosphite. The reaction mixture was shaken at room temperature and the chiral imidazolylpropanol dissolved immediately in an exothermic process. At that point, $^{31}$P NMR indicated the formation of several products, among which was one having a signal at 118.3 ppm and one having a signal at 120.5 ppm. (suspected diastereomers). After one hour and regular shaking of the NMR tube, $^{31}$P NMR indicated only one peak at 118.3 ppm At that stage, 20 µl (0.45 mmol) of isopropanol was introduced, and the tube was shaken again. $^{31}$P NMR indicated after 20 min the presence of a single peak at 140.6 ppm, indicating that the displacement of the imidazole moiety had given rise to a single diastereomer (19). 32 mg sulfur (1 mmol) was then introduced and the $^{31}$P-NMR was again recorded. The spectrum indicated a single peak at 64.8 ppm. The product (22) was then concentrated in vacuo and purified by flash chromatography (ethyl acetate/hexanes/triethylamine 79/20/1). $^1$H NMR (200 MHz, CDCl$_3$) 6.96 (s, 2H, NCH=CH—N); 4.83–4.97 (m, 1H, P—O—CH—CH$_3$); 4.58–4.75 (dh, 1H, $^3J_{H-H}$=6.2 Hz, $^3J_{H-P}$=9.6 Hz, OCH (CH$_3$)$_2$); 3.96–4.12 (m, 2H, P—O—CH$_2$CH$_3$); 2.98–3.20 (2×ABX, 2H, $^2J_{Ha-H}$=15.5 Hz, $^3J_{Ha-Hx}$=6.23 Hz, $^3J_{Hb-Hx}$=4.6 Hz, $^4J_{H-P}$=1.5 Hz, CH$_2$CHCH$_3$); 1.21–1.34 (m, 12H, CH(CH$_3$)+CH(CH$_3$)$_2$+CH$_2$CH$_3$) $^{13}$C NMR (50 MHz, CDCl$_3$) 144.00 (s, N—C=N); 121.70 (s, N—C=C—N); 74.90 (d, $^2J_{C-P}$=6.1 Hz, P—O—CH—(CH$_3$)CH$_2$); 73.80 (d, $^2J_{C-P}$=5.7 Hz, P—O—CH$_2$—CH$_3$); 64.25 (d, $^2J_{C-P}$=5.8 Hz, P—O—CH(CH$_3$)$_2$); 35.95 (s, P—O—CH(CH$_3$)CH$_2$—); 23.40 (s, P—O—CH(CH$_3$)$_2$); 21.06 (s, P—O—CH(CH$_3$)CH$_2$—); 15.83 (s, P—O—CH$_2$—CH$_3$) $^{31}$P NMR (81 MHz, CDCl$_3$) δ64.8 ppm M.S. (CI), [M+1]$^+$.293.

Example 28

Synthesis of thiophosphate ethyl (S)-1-(2-imidazolyl)-prop-2-yl 5 terbutyldimethylsilylthymidinyl ester (19)

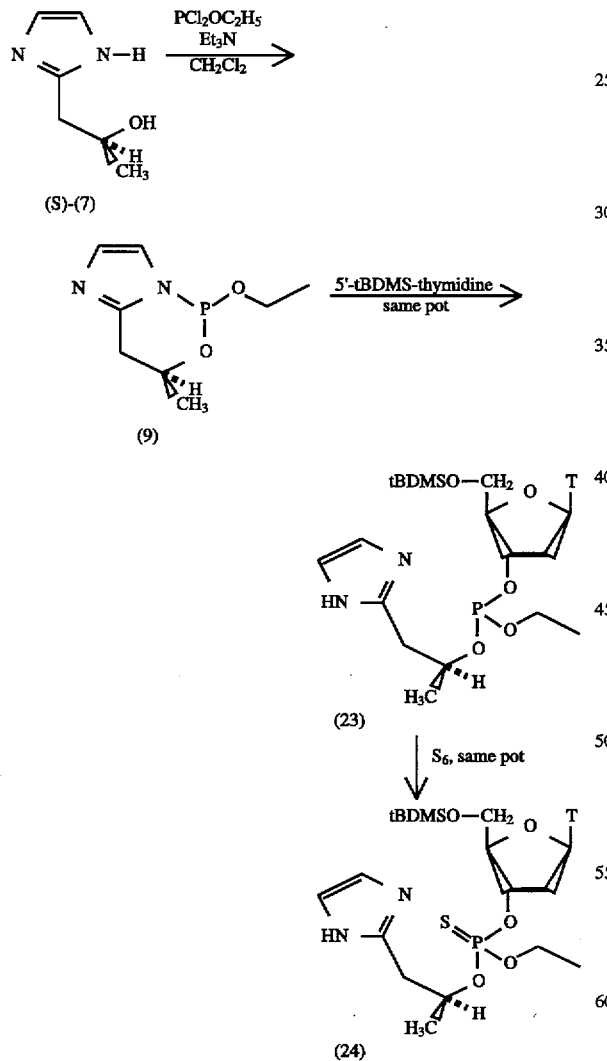

To a suspension of (S)-imidazolylpropanol (S)-(7) (0.30 mmol, 37.8 mg) in 2 ml dry dichloromethane and triethylamine (1.5 mmol, 0.21 ml) cooled down to 0° C. and stirred under Ar, was slowly added ethyl dichlorophosphite (0.30 mmol, 35 μl). The reaction mixture was then allowed to warm up to room temperature, the solid starting materials dissolved, and after about 2 hours, $^{31}$P NMR indicated the presence of a single peak at 118.3 ppm. At that time, the mixture was cooled down to 0° C. again, and at that temperature was added a mixture of 5'-tBDMS-thymidine (1) (0.30 mmol, 106 mg) in 1.5 ml of dry methylene chloride. The reaction mixture was allowed to warm up to room temperature again. $^{31}$P NMR indicated, after 30 min, a full conversion of the peak at 118.3 ppm to a single peak at 141.2 ppm, assigned to (23). Elemental sulfur S$_8$ (0.9 mmol, 29 mg) was then added after about 30 minutes. $^{31}$P NMR indicated conversion of the previously formed product to a single product (24) with a peak at 66.3 ppm. Evaporation of the reaction mixture followed by flash chromatography (ethyl acetate/triethylamine 80/20) afforded thioate (24) as a sticky solid (127 mg, 72%). $^1$H NMR (300 MHz, CD$_2$Cl$_2$) δ7.48 (d, 1H, $^4J_{H-H}$=1.3 Hz, C=CH); 6.94 (s, 2H, NCH=CHN); 6.25 (dd, 1H, $^3J_{H-H}$=5.1 Hz, $^3J_{H-H}$=9.2 Hz, NCHO); 4.84–5.05 (m, 2H, POCH(CH$_3$)CH$_2$+POCHCH$_2$O); 4.15–4.24 (m, 1H, SiOCH$_2$CHO); 3.96–4.14 (dq, 2H, $^3J_{H-P}$=9.4 Hz, $^3J_{H-H}$=7.0 Hz, POCH$_2$CH$_3$); 3.76–3.92 (ABX, 2H, $^2J_{Ha-Hb}$=11.5 Hz, $^3J_{Hb-Hx}$=2.5 Hz, $^3J_{Ha-Hx}$=2.4 Hz, SiOCH$_2$CHO); 2.98–3.08 (dd, 2H, $^3J_{H-H}$=5.8 Hz, $^4J_{H-P}$=1.1 Hz, POCH(CH$_3$)CH$_2$-Im); 1.98–2.08 (m, 2H, POCHCH$_2$CHN); 1.88 (s, 3H, CH=CCH$_3$); 1.39 (d, 3H, $^3J_{H-H}$=6.2 Hz, POCH(CH$_3$)); 1.28 (dt, 3H, $^3J_{H-H}$=7.0 Hz, $^4J_{H-P}$=0.9 Hz, POCH$_2$CH$_3$); 0.91 (s, 9H, SiC(CH$_3$)$_3$); 0.12 (s, 6H, Si(CH$_3$)$_2$).

$^{13}$C NMR (121 MHz, CD$_2$Cl$_2$, decoupled from $^1$H) δ164.1 (s, NCOC(CH$_3$)); 151.1 (s, NCON); 144.2 (s, NC=N); 135.5 (s, NC=C(CH$_3$)C=O); 132.4 (s, NC=CN); 186.1 (s, 11.5 (C(CH$_3$)CO); 86.1 (s, SiOCH$_2$CHO); 86.0 (s, NCHO); 79.9 (d, $^2J_{C-P}$=4.4 Hz, POCH(CH$_3$)); 76.2 (d, $^2J_{C-P}$=5.7 Hz, POCH$_2$CH$_3$); 65.0 (d, $^2J_{C-P}$=5.6 Hz, POCHCHO); 63.8 (s, SiOCH$_2$); 39.4 (s, POCHCH$_2$CHN); 36.6 (POCH(CH$_3$)CH$_2$); 26.1 (SiC(CH$_3$)$_3$); 21.3 (POCH(CH$_3$)); 18.6 (SiC(CH$_3$)$_3$); 16.0 (s, POCH$_2$CH$_3$); 12.7 (s, C=CCH$_3$); −5.4 (d, Si(CH$_3$)$_2$); MS (CI) (M+1)$^+$.589.

Example 29

1,2-O-3,5-O-dicyclopentylidene-D-xylofuranose (25)

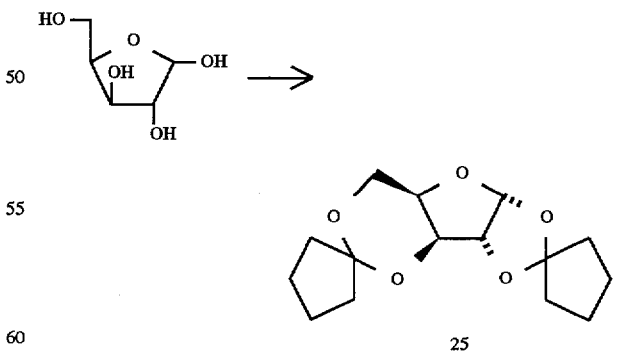

To a solution of trimethyl orthoformate (5 mmol, 547 μl) and p-toluene sulfonic acid (0.2 mmol, 38 mg) in dioxane (10 ml) under a nitrogen atmosphere at 0° C., was added dropwise cyclopentanone (40 mmol, 3.5 ml). This solution was stirred at room temperature for 2 hours and D-xylose (2 mmol, 300 mg) was added with stirring continued overnight. Then the reaction mixture was neutralized with triethylamine. Evaporation of the solvent furnished a yellow syrupy residue. A solution of the syrupy residue in chloroform (20 ml) was washed with water (20 ml). The aqueous layer was extracted with chloroform (3×15 ml). The combined chloroform layers were dried (MgSO$_4$). After removing the solvent, the mixture was chromatographed on a silica gel column (Hexane:Ethyl acetate=5:1) to give 340 mg white solid (60%). $^1$HNMR(200 MHz, CDCl3) δ5.99 (δ, J=3.80 Hz, 1H, H-1), 4.45 (d, J=3.81 Hz, 1H, H-2), 4.24 (d, J=2.15 Hz, 1H, H-3), 4.14–3.46 (m, 3H, H-4, 2×H-5), 1.98–1.55 (m, 16H, cyclopentylidene protons); $^{13}$C NMR (125 Mhz, CDCl$_3$) δ121.23 (C-1OCOC-2), 109.24 (C-3OCOC-5), 105.08 (C-1), 84.49 (C-2), 74.25 (C-4), 71.83 (C-3), 61.50 (C-5), 39.52, 36.82, 36.19, 29.74, 24.09, 23.49, 22.80, 22.37 (cyclopentylidene carbons); MS (CI) m/e: 283(M+H$^+$).

Example 30

1,2-O-cyclopentylidene-D-xylofuranose (26)

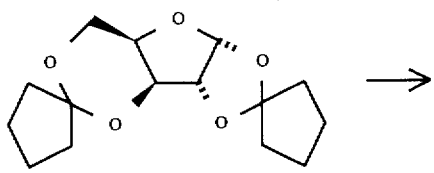

The 1,2-O-3,5-O-dicyclopentylidene-D-xylofuranose (25) (1 mmol, 282 mg) was dissolved in acetic acid-water (2:1) (14 ml) at room temperature. The reaction mixture was stirred for 3 hours, followed by TLC. Solvent was evaporated with high vacuum, and coevaporated with methanol three times and dried in vacuo overnight to give 196 mg white solid (91%). $^1$H NMR (500 MHz, CDCl$_3$) δ5.94 (d, J=3.91 Hz, 1H, H-1), 4.44 (d, J=3.91Hz, 1H, H-2), 4.32 (d, J=2.44 Hz, 1H, H-3), 4.18 (m, 1H, H-4), 4.10–4.02 (m, 2H, 2×H-5),1.96–1.61 (m, 8H, cyclopentylidene protons); $^{13}$C NMR (125 MHz, CDCl$_3$) δ121.41 (OCO), 104.53 (C-1), 85.59 (C-2), 78.76 (C-3), 76.83 (C-4), 61.07 (C-5), 36.84, 36.19 (CH$_2$CCH$_2$), 23.47, 22.80 (CH$_2$CH$_2$CCH$_2$CH$_2$); MS (CI): m/e 217(M+H$^+$).

Example 31

1,2-O-cyclopentylidene-5'-O-tosyl-D-xylofuranose (27)

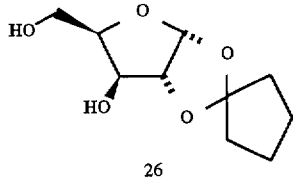

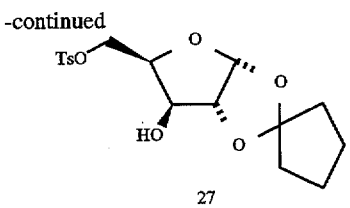

To a solution of 1,2-O-cyclopentylidene-D-xylofuranose (26) (0.81 mmol, 176 mg) in dry pyridine (6 ml) under nitrogen atmosphere at 0° C., p-toluenesulfonyl chloride (1.12 eq., 173 mg) was added. The reaction mixture was stirred at 0° C. for 3 hours. Then 5 ml water was added to quench the reaction, and the solvent was evaporated in high vacuum, and coevaporated with toluene twice. The mixture was dissolved in chloroform, washed with water three times and dried over MgSO$_4$. Removal of the solvent furnished 259 mg (27) as a white solid (86%). $^1$H NMR (200 MHz, CDCl$_3$) δ7.80–7.32 (AA'BB', 4H, Ph), 5.84 (d, J=3.63 Hz, 1H, H-1), 4.44 (d, J=3.7 Hz, 1H, H-2), 4.42–4.29 (m, 3H, H-3, 2×H-5), 4.27–4.09 (m, 1H, H-4), 2.44 (s, 3H, CH$_3$), 1.89–1.61 (m, 8H, cyclopentylidene protons); $^{13}$C NMR (270 MHz, CDCl$_3$) 145.34, 132.30, 130.06, 128.08 (aromatic), 121.86 (OCO), 104.80 (C-1), 85.15 (C-2), 77.73 (C-3), 74.41 (C-4), 66.21 (C-5), 37.02, 36.44(CH$_2$CCH$_2$), 23.54, 22.98 (CH$_2$CH$_2$CCH$_2$CH$_2$), 21.73 (CH$_3$); MS (CI): m/e 371 (M+H$^+$).

Example 32

1,2-O-dicyclopentylidene-5'-isopropylamine-D-xylofuranose (28)

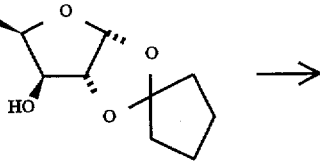

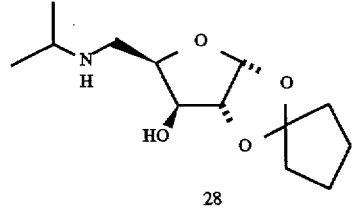

A solution of 1,2-O-cyclopentylidene-5'-tosyl-D-xylofuranose (27) (7.1 mmol, 2.64 g) in isopropylamine (15 ml) was stirred at 55° C. overnight in a pressure bottle. The solvent was removed by rotary evaporator and the remaining yellow syrup was taken up with chloroform and washed with a saturated solution of sodium bicarbonate, and then with brine. The organic phase was dried over MgSO$_4$, the solvent was evaporated and the residue was flash chromatographed on silica gel (ethyl acetate-3% triethylamine) to furnish 1.33 g (28) as a white solid (73%), m.p.44°–45° C.; [α]$_D^{20}$=31.06 (C=2,CHCl$_3$); $^1$H NMR (500 MHz, CDCl$_3$) δ8.0 (bs, NH) 5.90 (d, J=3.91 Hz, 1H, H-1), 4.38 (d, J=3.91 Hz, 1H, H-2), 4.27 (d, J=2.44 Hz, 1H, H-3), 4.20 (d, J=2.93 Hz, 1H, H-4), 3.36– 2.92 (ABX, 2H, 2×H-5), 2.74–2.70 (heptet, 1H, NCH), 1.95–1.63 (m, 8H, cyclopentylidene protons), 1.04–1.03 (dd, 6H, Me$_2$CH); $^{13}$C NMR (500 MHz, CDCl$_3$)

δ121.06 (OCO), 104.82 (C-1) 86.14 (C-2), 78.30 (C-3), 77.07(C-4), 48.64(NCH), 45.90(C-5), 36.85, 36.32 (CH$_2$CCH$_2$), 23.51, 22.84(CH$_2$CH$_2$CCH$_2$CH$_2$), 22.64 (CH$_3$CHN), 22.34(CH$_3$CHN); MS (CI): m/e 258([M+H$^+$], 100%); HRMS(EI) m/e calc'd for C$_{13}$H$_{23}$NO$_4$) [M$^+$]: 257.16270, found 257.1630.

Example 33

Chlorophosphoramidite (29)

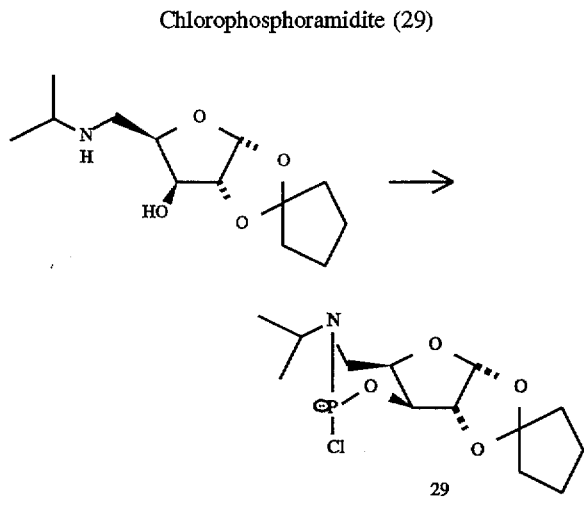

In a scrupulously dry NMR tube, 9.6 μl (0.11 mmol) phosphorus trichloride was placed via syringe, followed by 0.25 ml CDCl$_3$. The NMR tube was cooled at 0° C. and a solution of the 1,2-O-dicyclopentylidene-5'-isopropylamino-D-xylofuranose 28 (25.7 mg, 0.1 mmol) and triethylamine (27.8 ul, 0.22 mmol) in CDCl$_3$ (0.35 ml) were added under a nitrogen atmosphere with shaking of the NMR tube. An exothermic reaction was noticed. The NMR tube was then cooled to −78° C. pumped and sealed The sealed NMR tube was heated to 40° C. and the reaction was followed by $^{31}$P NMR until a single peak was found in the $^{31}$PNMR spectrum. The product was not isolated, and was used directly in the following step. $^1$H NMR (500 MHz, CDCl$_3$) δ5.75 (d, J=3.91 Hz, 1H, H-1), 4.51 (t, J=2.44 Hz, J=2.93 Hz, H-3), 4.37(d, J=3.91 Hz, 1H, H-2), 4.19–4.17(m, 1H, H-4), 3.42–3.34(heptet, 1H, NCH) 3.33–3.00 (ARX, 2H, 2×H-5), 1.81–1.51(m, 8H, cyclopentylidene protons), 1.05(d, J=6.84 Hz, 6H, Me$_2$CH); $^{13}$C NMR (125 MHz, CDCl$_3$) δ121.48 (OCO), 104.26 (C-1), 83.86, 83.83(d, J=3.66 Hz, C-2), 73.04, 72.99(d, J=6.41 Hz, C-3), 72.35(C-4), 50.42, 50.13(d, J=35.72 Hz, C- 5), 36.95, 36.91(d, J=5.50 Hz, NCH), 36.62, 35.91(CH$_2$CCH$_2$), 23.22, 22.50 (CH$_2$CH$_2$CCH$_2$CH$_2$), 20.89, 20.79(d, J=12.82 Hz, CH$_3$CHN), 19.64, 19.60(d, J=5.50 Hz, CH$_3$CHN); $^{31}$P NMR (202 MHz, CDCl$_3$) δ148.42.

Example 34

5'-O-(tert-butyldimethylsilyl)-thymidine-3'-O-Phosphoramidite (30)

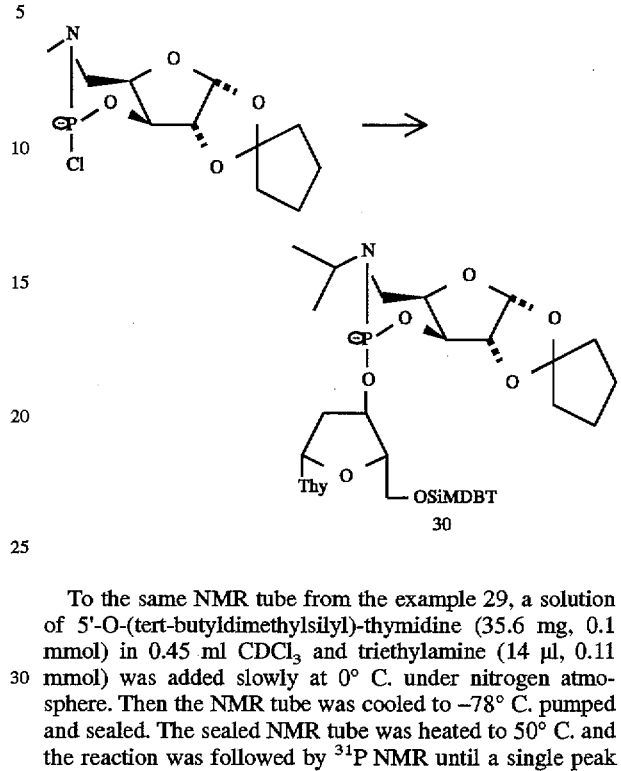

To the same NMR tube from the example 29, a solution of 5'-O-(tert-butyldimethylsilyl)-thymidine (35.6 mg, 0.1 mmol) in 0.45 ml CDCl$_3$ and triethylamine (14 μl, 0.11 mmol) was added slowly at 0° C. under nitrogen atmosphere. Then the NMR tube was cooled to −78° C. pumped and sealed. The sealed NMR tube was heated to 50° C. and the reaction was followed by $^{31}$P NMR until a single peak corresponding to a new product was found in the $^{31}$PNMR spectrum. The solution was poured into flask and taken up with ethyl acetate (prewashed with a saturated solution of sodium bicarbonate) and washed with saturated solution of sodium bicarbonate. The organic layer was dried over MgSO$_4$, the solvent was removed to furnish a white foam in a quantatitive yield. The crude product was flash chromatographed on a silica gel column (hexane-ethyl acetate-triethylamine=5:3:2); m.p.68°–70° C.; [α]$_D^{20}$=62.9° (c=0.5, CHCl$_3$) $^1$H NMR (500MHz, CDCl$_3$) δ7.98 (bs, 1H, NH), 7.46(d, J=1.00 Hz, 1H, H-6), 6.34–6.31(dd, J=5.86 Hz, J=8.30 Hz, 1H, H-1'), 5.88(d, J=3.91 Hz, 1H, H-1"), 4.56–4.53(m, 1H, H-3"), 4.41(d, J=3.91 Hz, 1H, H-2"), 4.35(m, 1H, H-3'), 4.17 (d, J=1.95 Hz, 1H, H-4"), 4.05 (d, J=1.95 Hz, 1H, H-4'), 3.89–3.76 (ABX, 2H, 2×H-5'), 3.45–3.39(m, 2H, H-5"), NCH), 3.03–2.99 (m, 1H, H-5"), 2.37–2.34 (m, 1H, H-2'), 2.09–2.05 (m, 1H, H-2'), 1.88(d, J=1.47 Hz, 3H, MeC=C), 1.95–1.61(m, 8H, cyclopentylidene protons), 111–1.00 (m, 6H, Me$_2$CH), 0.92(s, 9H, t-BuSi), 0.09(d, J=1.47 Hz, 6H, Me$_2$Si); $^{13}$C NMR (125 MHz, CDCl$_3$) δ163.77 (C-4), 150.35(C-2), 135.17(C-6), 121.42(OCO), 110.96(C-5), 104.59(C-1"), 86.38, 86.36(d, J=2.75 Hz, C-4'), 84.76(C-1'), 84.74(C-2"), 73.78, 73.63(d, J=19.23 Hz, C-3'), 73.07, 73.05(d, J=1.83, C-4"), 71.83, 71.80(d, J=3.66 Hz, C-3"), 63.17(C-5'), 50.09, 49.80(d, J=36.63 Hz, NCH), 40.27, 40.23 (d, J=4.58 Hz, C-2'), 36.89, 36.20(CH$_2$CCH$_2$), 36.11, 36.08(d, J=3.21 H$_z$, C-5"), 25.91 (SiCMe3), 23.44, 22.76(CH$_2$CH$_2$CCH$_2$CH$_2$), 22.02, 21.95 (d, J=9.16 Hz, CH$_3$CHN) , 21.69, 21.64(d, J=6.41 Hz, CH$_3$CHN), 18.31(SiCMe$_3$), 12.51(CH3C=C), −5.41, −5.48 (d, J=9.16 Hz, Me$_2$Si); $^{31}$P NMR (81 MHz, CDCl$_3$) δ130.14; MS (CI): m/e 642([M+H$^+$], 78%); EI m/e [M$^+$] 641, HRMS (EI) m/e calc'd for $C_{28}H_{45}N_3O_9PSi$ [M$^+$—CH$_3$] 626.26625, found 626.26670, and calc'd $C_{25}H_{39}N_3O_9PSi$ [M$^+$—C$_4$H$_9$]: 584.21930, found 584.2190. HRMS FAB (glycerol) m/e calcd. for $C_{29}H_{49}N_3O_9PSi$ [$^{MH30}$] 642, 2975; found 642.2973.

Example 35
Protected phosphorothioate dinucleotide (34)

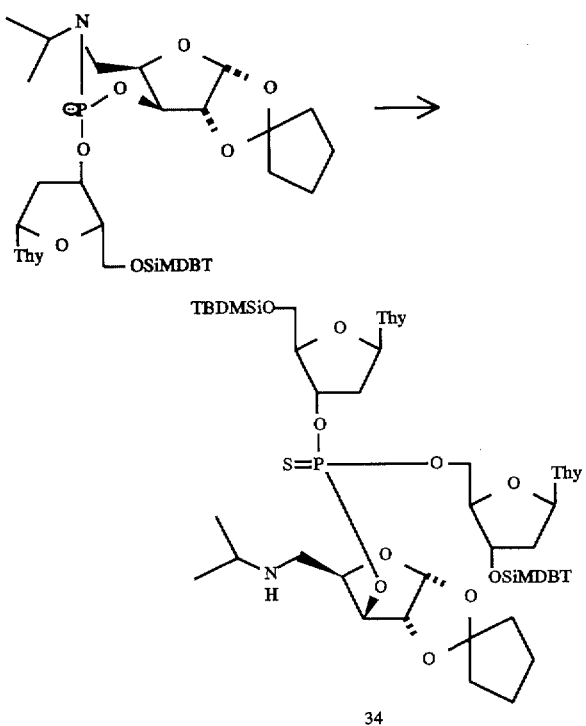

34

In a dried NMR tube, phosphoramidite 30 (15 mg, 0.0234 mmol), 3'-O-(tert-butyldimethylsilyl) thymidine (10 mg, 1.2 eq.) and 4,5-dicyano-2-bromo-imidazole 21 (9.17 mg, 2.0 eq.) were added. Then the NMR tube was dried in vacuum overnight. Dry acetonitrile (0.6 ml) was injected into the NMR tube at 0° C. under nitrogen atmosphere. The solid dissolved instantly. The reaction was moved to room temperature and was followed by $^{31}$P NMR. Within 5 minutes, the peak corresponding to the phosphoramidite disappeared and two new peaks (143.76 ppm, 142.55 ppm=6:1) were formed. The clean $^{31}$P NMR spectrum suggested use of this product directly in the following sulphurization without isolation. To this solution, Beaucage's reagent (5.6 mg, 1.2 eq.) in 140 ul acetonitrile (0.2M) was added. Instantaneously the $^{31}$P NMR showed another two peaks (68.43 ppm, 68.23 ppm=1:6), while the peaks corresponding to the starting material disappeared. The solution in NMR tube was transferred to a flask. Then the mixture was redissolved in ethyl acetate, washed with saturated sodium bicarbonate and water, and dried over MgSO$_4$. Removal of the solvent gave 22 mg of white solid 34 (91%). The product was then purified by chromatography on a silica gel column (ethyl acetate:methanol=95:5). $^1$H NMR (500 MHz, DMSO-d6) δ7.45(s, 1H, $^3$H-6), 7.42(s, 1H, $^5$H-6), 6.19–6.15(m, 2H, $^5$H-1', $^3$H-1'), 5.86, 5.85(d, J=3.91 Hz, 1H, H-1"), 5.05–5.04 (m, 1H, $^5$H-3'), 4.78–4.77(m, 1H, H-3"), 4.60, 4.59(d, J=3.42 Hz, 1H, H-2"), 4.38–4.36((m, 1H, H-4"), 4.26–4.13 (m, 4H, $^3$H-3', 2×$^3$H-5', $^5$H-4'), 3.93, 3.91(m, 1H, $^3$H-4'), 3.81–3.73(m, 2H, 2×$^5$H-5'), 2.66–2.52(m, 3H, NCH, 2×H-5"), 2.43–2.40(m, 1H, $^5$H-2'), 2.31–2.22(m, 2H, 2×$^3$H-2"), 2.09–2.07(m, 1H, $^5$H-2'), 1.78(s,3H, $^3$CH$_3$C=C), 1.76(s, 3H, $^5$CH$_3$C=C), 1.62–1.56(m, 8H, cyclopentylidene protons), 0.94–0.89(m, 6H, Me$_2$CHN), 0.86(s, 9H, $^3$t-BuSi), 0.85(s, 9H, $^5$t-BuSi), 0.069(s, 6H, Me$_2$Si), 0.065(s, 6H, Me$_2$Si); $^{13}$CNMR (125 MHz, CDCl$_3$) δ163.97, 163.66($^5$C-4, $^3$C-4), 150.39, 150.04($^5$C-2, $^3$C-2), 135.58, 134.49($^5$C-6, $^3$C-6), 121.77(OCO), 111.26, 111.04($^5$C-5, $^3$C-5), 104.00(C-1"), 85.59, 85.56(d, J=6.41 Hz, $^5$C-4'), 85.48($^3$C-1'), 84.69 84.61, 84.39 ($^5$C-1', $^3$C-4'), 83.47(C-2"), 80.85, 80.64(d, C-3"), 80.69, 80.66(d, $^5$C-3'), 79.03, 78.97(d, $^3$C-3'), 71.49 (C-4'), 67.66, 67.52(d, J=4.58 Hz, $^3$C-5'), 63.47($^5$C-5'), 48.93(NCH), 45.23(C-5"), 40.37($^3$C-2'), 39.14, 39.09(d, J=6.41 Hz, $^5$C-2'), 37.06, 36.16(CH$_2$CCH$_2$), 25.88, 25.60 ($^5$SiCMe$_3$, $^3$SiCMe$_3$), 23.52, 22.85(CH$_2$CH$_2$CCH$_2$CH$_2$), 22.65 22.39(NCHMe$_2$), 18.28, 17.81($^5$SiCMe$_3$, 3SiCMe$_3$), 12.51, 12.46 ($^5$C=CCH$_3$, $^3$C=CCH$_3$), −4.66, −4.83, −5.40, −5.46($^5$SiMe2, $^3$SiMe$_2$); $^{31}$P NMR (202 MHz, CDCl$_3$) δ68.43, 68.23 (1:6) MS (FAB): m/e 1030(M+H$^+$).

(II). 4,5-dicyano-2-bromo-imidazole 21 (7.6 mg, 2.5 eq.), phosphoramidite 30 (10 mg, 0.0156 mmol) and 3'-O-(tert-butyldimethylsilyl)thymidine (6.7 mg, 1.2 eq.) were added to a dried NMR tube. The NMR tube was dried under vacuum overnight, and dry CDCl$_3$ (0.5 ml) was injected into the NMR tube at 0° C. under an argon atmosphere. The reaction was followed by $^{31}$P NMR until the reaction went to completion. The $^{31}$P NMR spectrum showed that the peak corresponding to the phosphoramidite at 130 ppm had disappeared, and that two new peaks appeared at 142.634, 141.880 ppm in a ratio of 40:1. MS(FAB) [M+H$^+$]: calc'd for $C_{45}H_{76}N_5PO_{14}Si_2$ phosphite triester 998, found 998.4.

Beaucage's reagent (3.8 mg, 1.2 eq.) was added directly to the solution. The $^{31}$PNMR(202 MHz, CDCl$_3$, 0° C.) instantaeously showed another two peaks at 67.831 and 67.514 ppm in the same ratio, while the peaks corresponding to the phosphite triester disappeared. The solution in the NMR tube was transferred to a flask, the solvent was evaporated, and the product was then purified by chromatography on a silica gel column (ethyl acetate:hexane:triethylamine=60:35:5) to give only one isomer. $^{31}$PNMR (202 MHz, CDCl$_3$, room temperature) δ68.291.

(III) Virtually identical results were obtained when the reaction was carried out at −15° C. for 7 hours in CDCl$_3$, except that the ratio of isomers was ˜68:1. MS FAB (nitrobenzyl alcohol): m/e [MH$^+$]1030 HRMS FAB CsI m/e calcd. for $C_{45}H_{77}N_5O_{14}PSSi_2$ [MH$^+$], 1030.4464; found 1030.4460.

Example 36

Phosphorothioate dinucleotide (35)

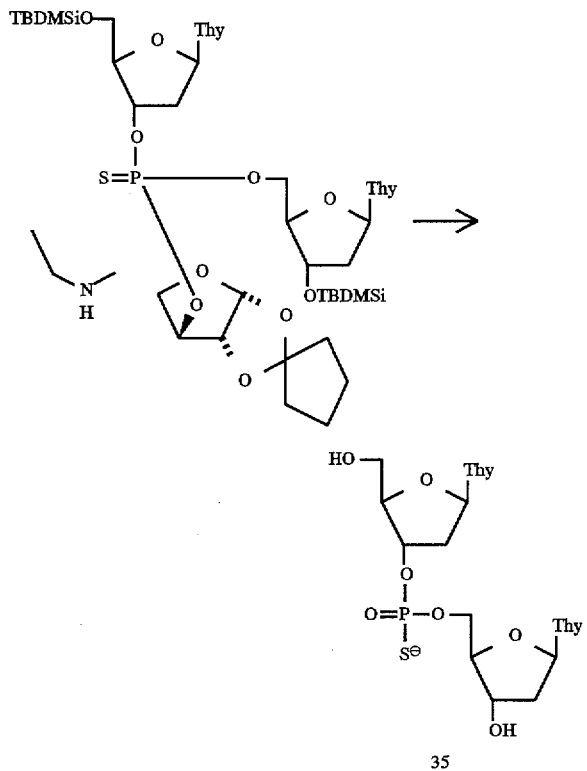

Protected phosphorothioate dinucleotide 34 (14 mg, 0.0136 mmol) from Example 35 was dissolved in 1 ml 70% TFA-H₂O at 0° C. with stirring, and then the reaction was allowed to proceed at room temperature. The reaction was followed by TLC until the spot corresponding to the starting material disappeared. Evaporation of the solvent and coevaporation with methanol three times furnished a white solid. The crude product was purified with preparative TLC plate (0.5 mm) (CH₂Cl₂:MeOH=5:1) to give 7.2 mg of a white solid (35) (94%); ¹H NMR (500 MHz, CD₃OD) δ7.87 (s, 1H, ³H-6), 7.85(s, 1H, ⁵H-6), 6.36–6.33(dd, J=6.35 Hz, J=7.81 Hz, 1H, ⁵H-1'), 6.30–6.27(dd, J=6.35 Hz, J=7.33 Hz ³H-1'), 5.06–5.03(m, 1H, ⁵H-3') 4.53–5.52(m, 1H, ³H-3'), 4.21–4.06(m, 4H, ⁵H-4', 2×³H-5', ³H-4'), 3.84–3.80(m, 2H, 2×⁵H-5'), 2.50–2.46(m, 1H, ⁵H-2'), 2.31–2.24(m, 2H, 2×³H-2'), 2.21–2.17(m, 1H, ⁵H-2'), 1.96(s, 3H, ³CH₃C=C), 1.87 (s, 3H, ⁵CH₃C=C); ³¹P NMR (202 MHz, CD₃OD) δ58.64: 58.57 (6:1) MS (FAB): m/e 563 (M+H⁺).

Example 37

1,2-O-3,5-O-dicyclopentylidene-L-xylofuranose (36)

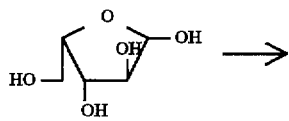

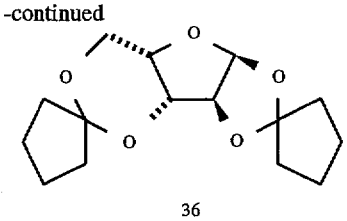

To a solution of trimethyl orthoformate (68 mmol, 7.5 ml) and p-toluene sulfonic acid (2 mmol, 380 mg) in dioxane (45 ml) under a nitrogen atmosphere at 0° C., was added dropwise cyclopentanone (500 mmol, 45 ml). This solution was stirred at room temperature for 2 hours and L-xylose (20 mmol, 3.0 g) was added with stirring continued overnight. Then the reaction mixture was neutralized with triethylamine. Evaporation of the solvent furnished a yellow syrupy residue. A solution of the syrupy residue in chloroform (50 ml) was washed with water (50 ml). The aqueous layer was extracted with chloroform (3×20 ml), and the combined chloroform layers were dried over (MgSO₄). After removing the solvent, the mixture was chromatographed on a silica gel column (hexane:ethyl acetate=5:1) to give 3.5 g white solid 36 (62%). ¹HNMR(500 MHz, CDCl₃) δ5.96 (d, J=3.91 Hz, 1H, H-1), 4.42 (d, J=3.91 Hz, 1H, H-2), 4.21 (d, J=1.95Hz, 1H, H-3), 4.09–3.98 (m, 3H, H-4, 2×H-5), 1.97–1.57 (m, 16H, cyclopentylidene protons); ¹³C NMR (125 MHz, CDCl₃) δ121.20 (C-1OCOC-2), 109.20 (C-3OCOC-5), 105.05 (C-1), 84.46 (C-2), 74.22 (C-4), 71.80 (C-3), 61.47 (C-5), 39.49, 36.80, 36.16, 29.71, 24.07, 23.47, 22.77, 22.34 (cyclopentylidene carbons); MS (CI) m/e: 283(M+H⁺).

Example 38

1,2-O-cyclopentylidene-L-xylofuranose (37)

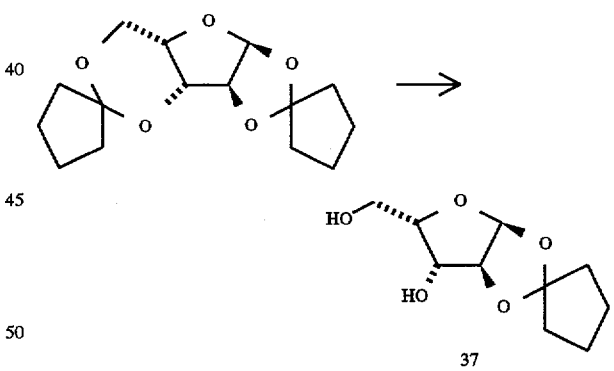

1,2-O-3,5-O-dicyclopentylidene-L-xylofuranose (36) (10 mmol, 2.82 g) was dissolved in acetic acid -water (2:1) (60 ml) at room temperature. The reaction mixture was stirred for 7 hours. The reaction was followed by TLC. The solvent was evaporated with high vacuum, coevaporated with methanol three times, and dried in vacuo overnight to give 2.16 g white solid 37 (100%). ¹H NMR (500 MHz, CDCl₃) δ5.92 (d, J=3.91 Hz, 1H, H-1), 4.42(d, J=3.91 Hz, 1H, H-2), 4.30 (d, J=2.93 Hz, 1H, H-3), 4.17–4.14 (m, 1H, H-4), 4.07–3.97 (m, 2H, 2×H-5), 1.96–1.60 (m, 8H, cyclopentylidene protons); ¹³C NMR (125 MHz, CDCl₃) δ121.42 (OCO), 104.52 (C-1), 85.56 (C-2), 78.81 (C-3), 76.77 (C-4), 61.01 (C-5), 36.84, 36.19 (CH₂CCH₂), 23.47, 22.79 (CH₂CH₂CCH₂CH₂); MS (CI): m/e 217(M+H⁺).

Example 39

1,2-O-cyclopentylidene-5'-O-tosyl-L-xylofuranose (38)

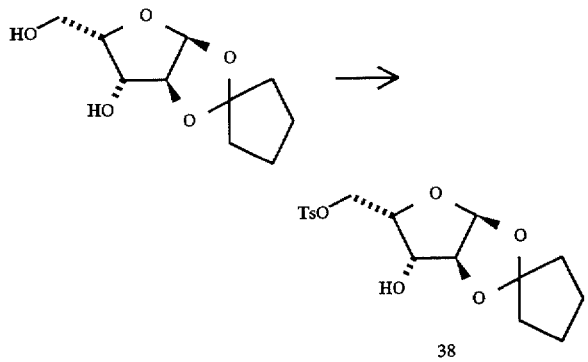

To a solution of 1,2-O-cyclopentylidene-L-xylofuranose (37) (9.4 mmol, 2.03 g) in dry pyridine (25 ml) under nitrogen atmosphere at 0° C., p-toluenesulfonyl chloride (1.2 eq., 2.15 g) was added. The reaction mixture was stirred at 0° C. for 12 hours. Then 10 ml water was added to quench the reaction, and the solvent evaporated in high vacuum, and coevaporated with toluene twice. The mixture was dissolved in chloroform, washed with water three times and dried over MgSO$_4$. Removal of the solvent furnished 2.96 g of 38 as a white solid (85%). $^1$H NMR (500 MHz, CDCl$_3$) δ7.78–7.32 (AA'BB', 4H, Ph), 5.83 (d, J=3.42 Hz, 1H, H-1), 4.42 (d, J=3.91 Hz, 1H, H-2), 4.42–4.24 (m, 3H, H-3, 2×H-5), 4.16–4.08 (m, 1H, H-4), 2.42 (s, 3H, CH$_3$), 1.90–1.63 (m, 8H, cyclopentylidene protons); $^{13}$C NMR (270 MHz, CDCl$_3$) δ145.25, 130.26, 130.09, 130.01, 129.96 (aromatic), 121.71 (OCO), 104.69 (C-1), 85.04 (C-2), 77.67 (C-4), 74.25 (C-3), 66.39 (C-5), 36.89, 36.30(CH$_2$CCH$_2$), 23.42, 22.85 (CH$_2$CH$_2$CCH$_2$CH$_2$), 21.63 (CH$_3$); MS (CI): m/e 371 (M+H$^+$).

Example 40

1,2-O-dicyclopentylidene-5'-isopropylamine-L-xylofuranose (39)

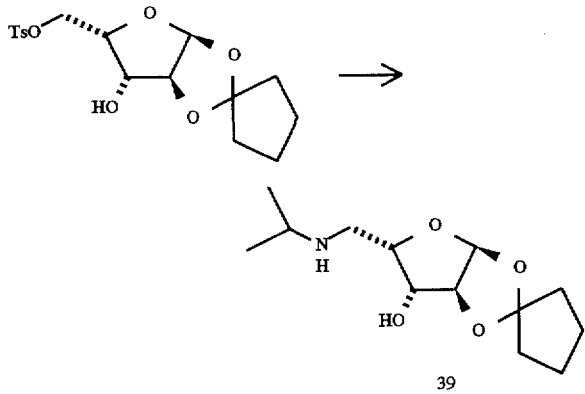

A solution of 1,2-O-cyclopentylidene-5'-tosyl-L-xylofuranose (38) (7.0 mmol, 2.6 g) in isopropylamine (15 ml) was stirred at 55° C. overnight in a pressure bottle. The solvent was removed by rotary evaporator and the remaining yellow syrup was taken up with chloroform and washed with a saturated solution of sodium bicarbonate and with brine. The organic phase was dried over MgSO$_4$, the solvent was evaporated and the residue was flash chromatographed on silica gel (ethyl acetate-3% triethylamine) to furnish 1.30 g white solid 39 (72%). m.p. 39°–41° C.; [α]$_D^{20}$=–31.37(c= 2,CHCl$_3$); $^1$H NMR (500 MHz, CDCl$_3$) δ8.0(bs, NH), 5.88 (d, J=3.91 Hz, 1H, H-1), 4.37 (d, J=3.91 Hz, 1H, H-2), 4.25 (d, J=2.93 Hz, 1H, H-3), 4.19 (m, 1H, H-4), 3.34–2.91 (ABX, 2H, 2×H-5), 2.73–2.71 (heptet, 1H, NCH), 1.92–1.61 (m, 8H, cyclopentylidene protons), 1.03–1.01(dd, J=2.44 Hz, J=6.35 Hz, 6H, Me$_2$CH); $^{13}$C NMR (500 MHz, CDCl$_3$) δ121.00 (OCO), 104.75 (C-1), 86.06 (C-2), 78.20 (C-3), 77.00(C-4), 48.62(NCH), 45.82(C-5), 36.78, 36.25 (CH$_2$CCH$_2$), 23.46, 22.78 (CH$_2$CH$_2$CCH$_2$CH$_2$), 22.57 (CH$_3$CHN), 22.27 (CH$_3$CHN); MS (CI): m/e 258([M+H$^+$]; 100%); HRMS(EI) m/e calc'd for C$_{13}$H$_{23}$NO$_4$ [M$^+$]: 257.16270, found 257.16250.

Example 41

Chlorophosphoramidite (40)

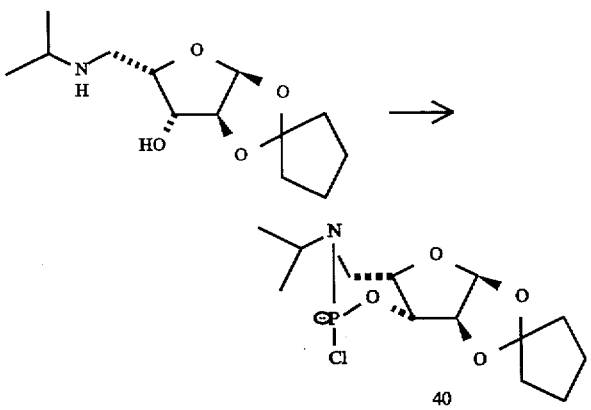

In a scrupulously dry NMR tube, 9.6 μl (0.11 mmol) phosphorus trichloride was added via syringe, then 0.25 ml CDCl$_3$ was similarly added. This NMR tube was cooled to 0° C., and a solution of the 1,2-O-dicyclopentylidene-5'-isopropylamine-L-xylofuranose (17) (25.7 mg, 0.1 mmol) and triethylamine (27.8 ul, 0.22 mmol) in CDCl$_3$ (0.35 ml) was added under a nitrogen atmosphere with shaking of the NMR tube. An exothermic reaction was noticed. The NMR tube was then cooled to –78° C., pumped and sealed. The sealed NMR tube was heated to 40° C. and the reaction was followed by $^{31}$PNMR until a single peak was found in the $^{31}$PNMR spectrum. The product was not isolated, and was directly used in the following step. $^{31}$P NMR (300 MHz, CDCl3) δ148.75

Example 42

5'-O-(tert-butyl dimethyl silyl)-thymidine-3'-O-Phosphoramidite (41)

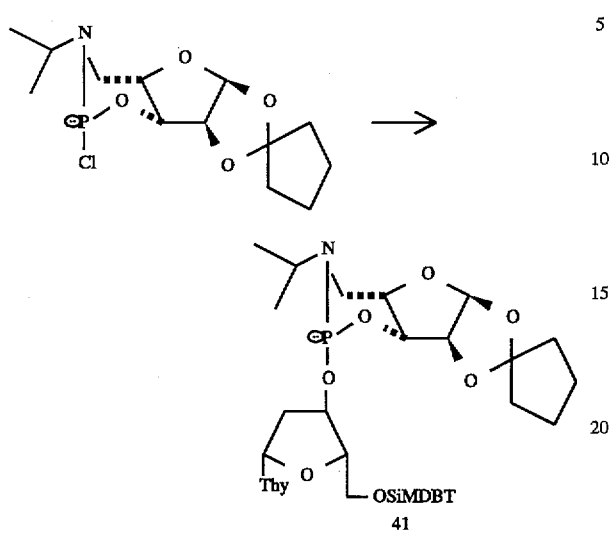

41

To the same NMR tube from previous Example 41, a solution of 5'-O-(tert-butyl dimethyl silyl)-thymidine (35.6 mg, 0.1 mmol) in 0.45 ml CDCl$_3$ and triethylamine (14 μl, 0.11 mmol) was added slowly at 0° C. under a nitrogen atmosphere. Then the NMR tube was cooled to −78° C., pumped and sealed. The sealed NMR tube was heated to 50° C. and the reaction was followed by $^{31}$PNMR until a single peak corresponding to a new product was found in the $^{31}$PNMR spectrum. The solution was poured into a flask, and taken up with ethyl acetate (prewashed with a saturated solution of sodium bicarbonate) and washed with saturated solution of sodium bicarbonate. The organic layer was dried over MgSO$_4$, and the solvent was removed to furnish a white foam in a quantatitive yield. The crude product was flash chromatographed on a silica gel column (hexane-ethyl acetate-triethylamine=5:3:2) to furnish white crystals (41); m.p. 99°–101° C.; [α]$_D^{20}$ −72.0° (c=0.5,CHCl$_3$) $^1$H NMR (500 MHz, CDCl$_3$) δ8.77 (bs, 1H, NH), 7.46(s, 1H, H-6), 6.33–6.30(dd, J=5.86 Hz, J=7.81 Hz, 1H, H-1'), 5.88(d, J=3.91 Hz, 1H, H-1"), 4.56–4.53(m, 1H, H-3'), 4.43(d, J=3.42 Hz, 1H, H-2"), 4.35(m, 1H, H-3"), 4.18 (d, J=1.95 Hz, 1H, H-4"), 4.05 (m, 1H, H-4'), 3.90–3.76 (ABX, 2H, 2×H-5'), 3.45–3.42(m, 2H, H-5", NCH), 3.03–2.99 (m, 1H, H-5"), 2.38–2.35 (m, 1H, H-2'), 2.12–2.06(m, 1H, H-2'), 1.89(s, 3H, MeC=C), 1.96–1.62(m, 8H, cyclopentylidene protons), 1.11–1.08 (m, 6H, Me$_2$CH), 0.90(s, 9H, t-BuSi), 0.09, (d, J=1.95 Hz, 6H, Me$_2$Si); $^{13}$C NMR (125 MHz, CDCl$_3$) δ163.74 (C-4), 150.31(C-2), 135.18(C-6), 121.44 (OCO), 110.93(C-5), 104.59(C-1"), 86.61, 86.57(d, J=5.49Hz, C-4'), 84.75, 84.73(d, J=2.75 Hz, C-1'), 84.70(C-2"), 73.07, 73.05(d, J=1.83 Hz, C-3'), 73.03, 72.89(d, J=17.4, C-4"), 71.82, 71.78(d, J=4.58 Hz, C-3"), 62.98(C-5'), 50.05, 49.76(d, J=36.63 Hz, NCH), 39.94, 39.92(d, J=2.75 Hz, C-2'), 36.86, 36.19(CH$_2$CCH$_2$), 36.11, 36.08(d, J=3.06 H$_z$, C-5"), 25.92(SiCMe3), 23.45, 22.76 (CH$_2$CH$_2$CCH$_2$CH$_2$), 21.99, 21.91(d, J=9.16 Hz, CH$_3$CHN), 21.69, 21.64(d, J=6.41 Hz, CH$_3$CHN), 18.35 (SiCMe3), 12.52(CH3C=C), −5.39, −5.45 (d, J=9.16 Hz, Me$_2$Si); $^{31}$P NMR (81 MHz, CDCl$_3$) δ129.34; MS (CI): m/e 642(M+H$^+$). EI: m/e 641[M+]. MS FAB (nitrobenzyl alcohol): m/e [MH$^+$] 642, HRMS FAB (glycerol) m/e calcd. for C$_{29}$H$_{49}$N$_3$O$_9$PSi [MH$^+$] 642.2975; found 642.2973.

Example 43

Protected phosphorothioate dinucleotide (42)

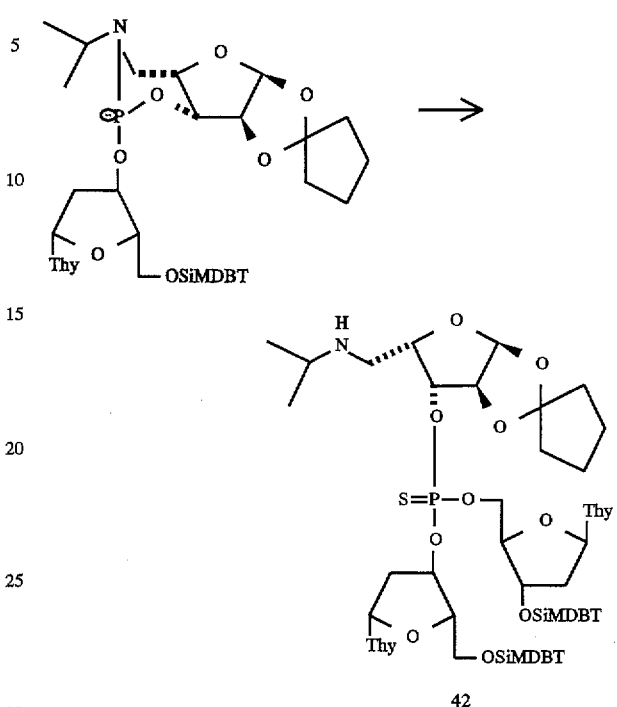

42

I: In a dried NMR tube, phosophoramidite 41 (15 mg, 0.0234 mmol), 3'-O-(tert-butyldimethylsilyl) thymidine (10 mg, 1.2 eq.) and 4,5-dicyano-2-bromo-imidazole 21 (9.17 mg, 2.0 eq.) were added. Then the NMR tube was dried in vacuum overnight. Dry acetonitrile (0.6 ml) was injected into the NMR tube at room temperature under a nitrogen atmosphere. The solid dissolved instantly. The reaction was followed by $^{31}$PNMR. Within 5 minutes, the peak corresponding to the phosphoramidite disappeared. To this solution, Beaucage's reagent (5.6 mg, 1.2 eq.) in 140 μl acetonitrile (0.2M) was added. The peaks corresponding to the starting material disappeared. The solution in NMR tube was transferred to a flask, and the solvent evaporated. Then the mixture was redisolved in ethyl acetate, washed with saturated sodium bicarbonate and water, and dried over MgSO$_4$. After removal of the solvent, the product was purified by chromatography on a silica gel column (ethyl acetate:methanol=95:5) to furnish 42 in a diastereomeric ratio of 7:1(69.12, 68.91 ppm). $^1$H NMR (500 MHz, CDCl$_3$) δ7.46(s, 1H, $^3$H-6), 7.27(s, 1H, $^5$H-6), 6.34–6.10 (m, 2H, $^5$H-1', $^3$H-1'), 5.86, 5.87(d, J=3.42Hz, 1H, H-1"), 5.17–5.14 (m, 1H, $^5$H-3'), 4.83–4.81(d, J=10.25 Hz,1H, H-3"), 4.56, 4.55(d, J=3.91 Hz, 1H, H-2"), 4.38(m, 2H, $^3$H-3', H-4"), 4.25–4.21(m, 3H, 2×$^3$H-5', $^5$H-4'), 3 98(m, 1H, $^3$H-$_4$'), 3.91–3.85(m, 2H, 2×$^5$H-5'), 2.85, 2.84(d, J=6.35 Hz, 1H, 2×H-5"), 2.81(m, 1H, NCH), 2.52–2.47(dd, 2H, $^5$H-2'), 2.25–2.23(m, 2H, 2×$^3$H-2'), 2.08–2.02 (m, 1H, $^5$H-2'), 1.91 (s,3H, $^5$CH$_3$C=C), 1.89(S, 3H, $^3$CH$_3$C=C), 1.92–1.65(m, 8H, cyclopentylidene protons), 1.05, 1.04(d, J=5.86 Hz, 6H, Me$_2$CHN), 0.90(s, 9H, $^3$t-BuSi), 0.86(s, 9H, $^5$t-BuSi), 0.11 (s, 6H, Me$_2$Si), 0.05(s, 6H, Me$_2$Si); $^{13}$CNMR (125 MHz, CDCl$_3$) δ163.80, 163.59($^5$C-4, $^3$C-4), 150.33, 150.15($^5$C-2, $^3$C-2), 136.13, 134.64($^5$C-6, $^3$C-6), 122.03(OCO), 111.43, 111.11($^5$C-5, $^3$C-5), 104.28(C-1"), 86.29($^3$C-1'), 85.95, 85.90(d, J=6.41 Hz, $^5$C-4') , 84.80 84.72, 84.69 ($^5$C-1', $^3$C-4'), 83.59(C-2"), 80.85, 80.81(d, J=4.58 Hz, C-3"), 80.69, 80.66(d, J=4.58 Hz, $^5$C-3'), 79.03, 78.97(d, J=8.24 Hz, $^3$C-3'), 71.30(C-4"), 67.38, 67.34(d, J=5.50 Hz, $^3$C-5'), 63.37($^5$C-5'), 48.91(NCH), 45.18(C-5"), 40.35($^3$C-2'), 39.12, 39.09(d, J=3.66 Hz, $^5$C-2'), 37.14, 36.23(CH$_2$CCH$_2$), 25.88, 25.65($^5$SiCMe$_3$, $^3$SiCMe$_3$), 23.55, 22.89 (CH$_2$CH$_2$CCH$_2$CH$_2$), 22.80, 22.55(NCHMe$_2$), 18.28, 17.86 ($^5$SiCMe$_3$, 3SiCMe$_3$), 12.52, 12.49($^5$C=CCH$_3$, $^3$C=CCH$_3$), −4.66, −4.83, −5.40, −5.46($^5$SiMe2, $^3$SiMe$_2$); $^{31}$P NMR (121 MHz, CDCl$_3$) δ69.12, 68.91 (7:1); MS (FAB): m/e (M+H$^+$).

Example 44

Phosphorothioate dinucleotide (43)

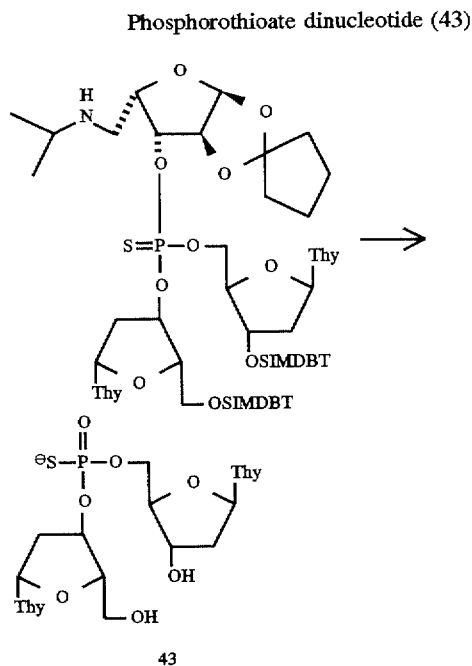

43

The protected phosphorothioate dinucleotide 42 obtained from example 43-I (15 mg, 0.014 mmol) was dissolved in 1 ml 70% TFA-H$_2$O at 0° C. with stirring and, the reaction was allowed to proceed at room temperature. The reaction was followed by TLC until the spot corresponding to the starting material disappeared. Evaporation of the solvent and coevaporation with methanol three times furnished a white solid. The crude product was purified with preparative TLC plate (0.5 mm) (CH$_2$Cl$_2$:MeOH=5:1) to give 43 as a white solid: $^1$H NMR (500 MHz, CD$_3$OD) δ7.91 (s, 1H, $^3$H-6, 7.86(s, 1H, $^5$H-6), 6.36–6.33(dd, J=6.35 Hz, J=7.81 Hz, 1H, $^5$H-1'), 6.29–6.26(dd, J=5.86 Hz, J=7.81 Hz $^3$H-1'), 5.08–5.05(m, 1H, $^5$H-3') 4.52–5.51(m, 1H, $^3$H-3'),4.21(m, 1H, $^5$H-4'), 4.14–4.11(m, 2H, 2×$^3$H-5'), 4.04 (m, 1H, $^3$H-4'), 3.86–3.79(m, 2H, 2×$^5$H-5'), 2.48–2.44(m, 1H, $^3$H-2'), 2.31–2.24(m, 2H, 2×$^5$H-2'), 2.23–2.16(m, 1H, $^3$H-2'), 1.97 (s, 3H, $^3$CH$_3$C=C), 1.87(s, 3H, $^5$CH$_3$C=C); $^{31}$P NMR (121 MHz, CDCl$_3$) δ59.14: 59.08(1:7); MS (FAB): m/e (M+H$^+$)

Example 45

Synthesis of γ-aminoalcohol 44 (Scheme 1)

The synthesis of amino-alcohol 44 is shown in Scheme 1 below:

Scheme 1

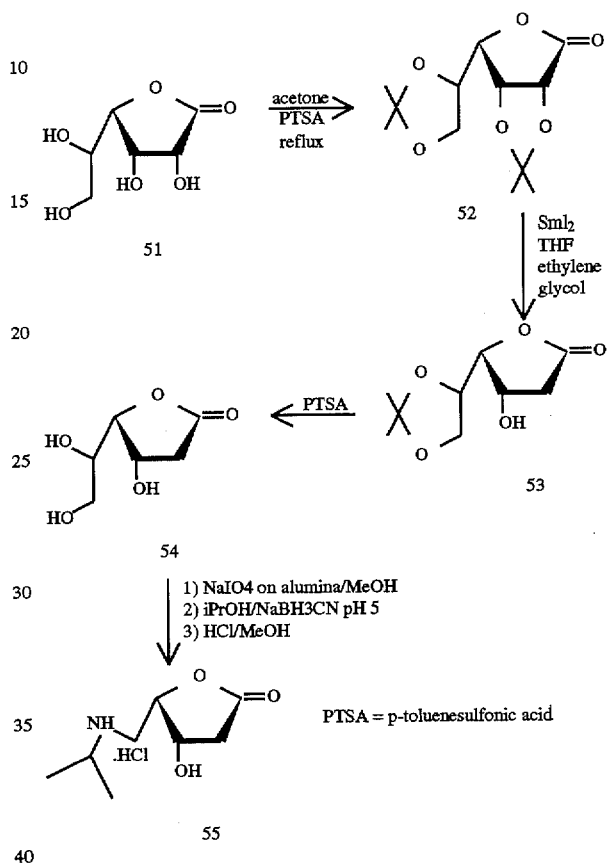

PTSA = p-toluenesulfonic acid

Starting from L-mannonic-γ-lactone 51, both diols are protected by conversion to their acetonides according to standard procedures, using acetone with paratoluenesulfonic acid as a catalyst, to yield bis-acetonide lactone 52.

The bis-acetonide is then reacted in presence of samarium iodide in a mixture of THF and ethylene glycol at room temperature according to the procedure described by Christian Girard, Ph.D. Thesis, Universite de Montreal, 1995. This reaction proceeds with high yield and high regioselectivity and affects the acetonide located on the s-position to the ester, yielding β-hydroxyester 53.

The next step is a classical acid-catalyzed deprotection of the acetonide to give triol product 54. The diol function of the triol is then cleaved by sodium periodate on alumina in methanol. The intermediate aldehyde undergoes a reductive amination in presence of isopropylamine and sodium cyanoborohydride to yield γ-aminoalcohol 55, which is isolated and stabilized as the hydrochloride salt. See Robert Hambalek, Ph.D. Thesis, McGill University, 1992.

γ-aminoalcohol 55 is then employed as a chiral precursor to the stereocontrolled synthesis of a P-chiral phosphorothioate dimer that can be deprotected by a base-catalyzed β-elimination. An example of this type of elimination is found in Takahata et al., *J. Org. Chem.* 1995, 60, 5628–5633.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

It is intended that each of the patents, publications, and other published documents mentioned or referred to in this specification be herein incorporated by reference in their entirety.

What is claimed is:

1. A method for synthesizing an oligomer having a phosphorothioate linkage comprising the steps of:

reacting a first synthon of Formula I:

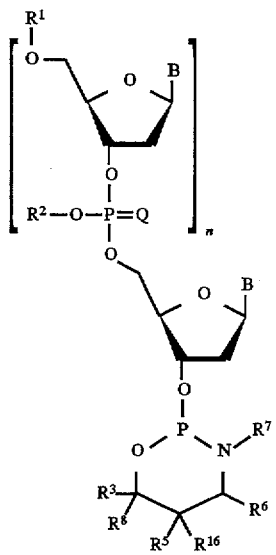

wherein:
Q is independently O or S;
R$^1$ is a hydroxyl protecting group;
R$^2$ is a chiral auxiliary of formula —C(R$^8$)R$^3$—C(R$^{16}$)R$^5$—CHR$^6$—NHR$^7$;
R$^3$ is hydrogen, alkyl, cyanomethyl, monohalomethyl, dihalomethyl, trihalomethyl, —CH$_2$Si(R$^4$)$_3$, or —CH$_2$—SO$_k$R$^4$ where k is 0, 1 or 2;
R$^4$ is independently alkyl, aryl, aralkyl or alkaryl having up to 15 carbon atoms;
R$^5$ is H, —CN, —Si(R$^4$)$_3$, SO$_k$R$^4$ or halogen;
or R$^8$ and R$^{16}$ are each H, and R$^3$ and R$^5$, together, form one of the structures

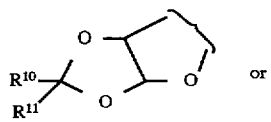

or

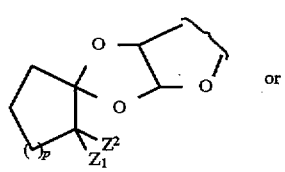

-continued

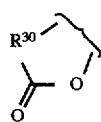

wherein:
R$^{10}$ and R$^{11}$ are H, alkyl having from 1 to about 10 carbons, —CH$_2$C(=O)OR$^{22}$, —CH$_2$CN, —CH$_2$Si(CH$_3$)$_3$, or o- or p-C$_6$H$_4$-R$^{21}$;
R$^{21}$ is hydrogen, —O—C(=O)CH$_3$, alkoxy having from 1 to about 10 carbons, —NO$_2$, or —N(R$^{22}$)$_2$;
R$^{22}$ is independently H or alkyl having from one to about 10 carbon atoms;
p is 1 or 2;
Z$^1$ and Z$^2$ are independently halogen, CN, —Si(CH$_3$)$_3$, and —C(=O)OR$^{22}$;
R$^{30}$ is hydrogen, —O—C(=O)CH$_3$, alkoxy having from 1 to about 10 carbons, or —O—Si(R$_4$)$_3$;
R$^6$ is H, alkyl or aralkyl having up to 15 carbon atoms;
or R$^5$ and R$^6$, together with the atoms to which they are attached, form a 5 or 6 membered ring;
R$^7$ is alkyl or aralkyl having up to 15 carbon atoms;
or R$^6$ and R$^7$ together form one of the structures

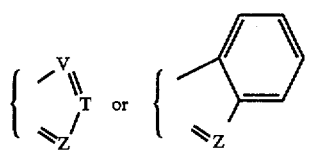

wherein V, T, and Z are independently CH or N;
R$^8$ is H or methyl;
R$^{16}$ is H, alkyl or aralkyl having up to 15 carbon atoms;
B is a nucleobase; and
n is an integer from 0 to 50; with a second synthon of Formula II:

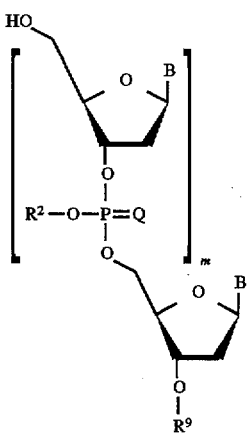

wherein:
R$^9$ is a hydroxyl protecting group or a linker connected to a solid support; and
m is an integer from 0 to 50; for a time and under reaction conditions effective to form a third synthon of Formula III:

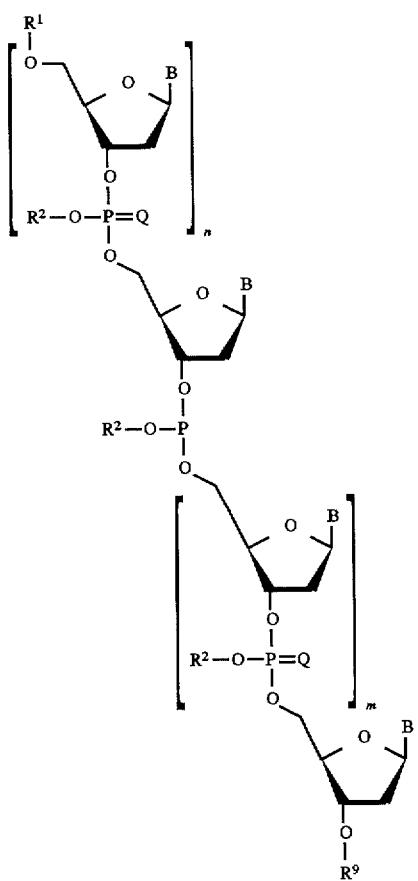
and
contacting said third synthon with a sulfurizing agent to form an oligomer of Formula IV:
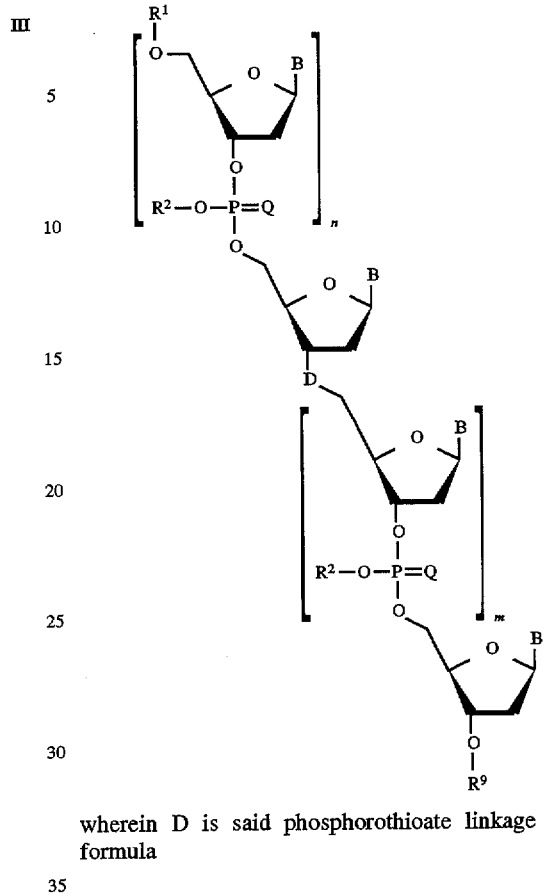
wherein D is said phosphorothioate linkage having the formula
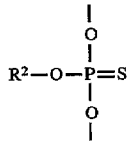

2. The method of claim 1 wherein said phosphozothioate linkage is diastereomerically enriched.

3. The method of claim 1 wherein about 75% of said phosphorothioate linkage is in a single stereoisomeric form.

4. The method of claim 1 wherein about 85% of said phosphorothioate linkage is in a single stereoisomeric form.

5. The method of claim 1 wherein about 95% of said phosphorothioate linkage is in a single stereoisomeric form.

6. The method of claim 1 wherein said phosphorothioate linkage is in a single stereoisomeric form, substantially free of other stereoisomeric forms.

7. The method of claim 1 wherein n is 0.

8. The method of claim 1 wherein said first synthon is in a single stereoisomeric form, substantially free of other stereoisomeric forms.

9. The method of claim 1 further comprising removing said $R^1$ group from said phosphorothioate.

10. The method of claim 1 further comprising removing said chiral auxiliaries.

11. The method of claim 1 wherein said compound of Formula IV contains a plurality of said phosphorothioate linkages.

12. The method of claim 1 wherein said first and second synthons are reacted at a temperature of from about −20° C. to about 40° C.

13. The method of claim 1 wherein said first and second synthons are reacted at a temperature of from about −15° C. to about 0° C.

14. The method of claim 1 wherein said first synthon is formed by reacting a compound of Formula V:

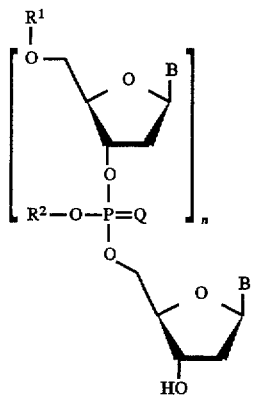

with an azaphospholane of Formula VIa:

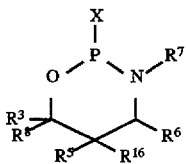

wherein $R^3$–$R^8$ are as defined above; and X is halogen, dialkylamino, imidazole, triazole or substituted phenoxy wherein said substituents are electron withdrawing.

15. The method of claim 14 wherein said electron withdrawing substituents are halogen or nitro.

16. The method of claim 14 wherein said azaphospholane is produced by reacting a reagent of formula HO—C($R^8$)$R^3$—C($R^{16}$)$R^5$—CHR$^6$—NHR$^7$ and a phosphorus trihalide, phosphorus tri(dialkylamide), phosphorus triphenoxide, or phosphorus tri(imidazolides).

17. The method of claim 1 wherein said first synthon is formed by reacting a compound of Formula VII:

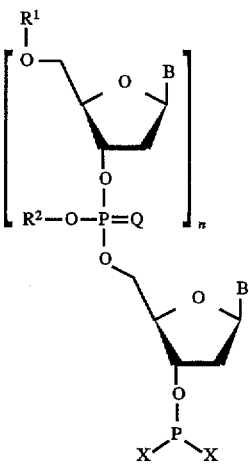

and a γ-amino alcohol of formula HO—C($R^8$)$R^3$—C($R^{16}$)$R^5$—CHR$^6$—NHR$^7$; wherein X and $R^1$-$R^8$ and $R^{16}$ are as defined above.

18. The method of claim 17 wherein X is chlorine.

19. The method of claim 17 wherein said reaction is stereoselective.

20. The method of claim 18 wherein said first synthon is in a single stereoisomeric form, substantially free of other stereoisomeric forms.

21. The method of claim 1 wherein said reaction is performed in the presence of a catalyst.

22. The method of claim 21 wherein said catalyst has one of the Formulas VIII or IX:

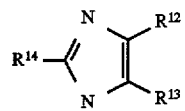

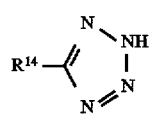

wherein:

$R^{12}$ and $R^{13}$ are independently hydrogen, halogen, cyano, nitro, alkyl having from one to 10 carbons, group, or $R^{12}$ and $R^{13}$ together with the carbon atoms to which they are attached, form a substituted or unsubstituted phenyl ring where said substituents are electron withdrawing; and $R^{14}$ is hydrogen; halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

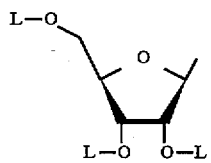

wherein L is protecting group.

23. The method of claim 21 wherein $R^{14}$ is halogen or nitro, and wherein $R^{12}$ and $R^{13}$ are each halogen or each cyano.

24. The method of claim 22 wherein $R^{14}$ is bromine, and $R^{12}$ and $R^{13}$ are each cyano.

25. The method of claim 22 wherein $R^{14}$, $R^{12}$ and $R^{13}$ are each bromo.

26. The method of claim 21 wherein $R^{14}$ has one of the formulas:

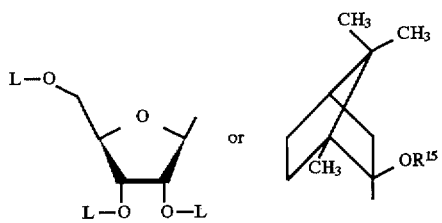

wherein $R^{15}$ is H, methyl, trialkylsilyl or acetyl.

27. The method of claim 1 wherein $R^3$ is cyanomethyl or —CH$_2$—SO$_k$R$^4$ where k is 0, 1 or 2.

28. The method of claim 27 wherein $R^7$ is lower alkyl or aralkyl.

29. The method of claim 1 wherein said first synthon has one of the Formulas Xa, XIa, XIIa, XIIIa or XXa:

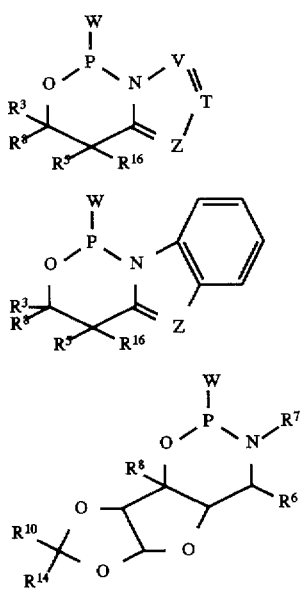

wherein W has the formula:

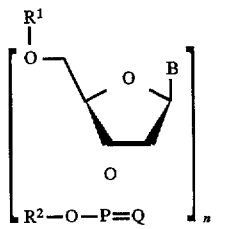

and $R^1$-$R^{16}$, V, T and Z are as defined above.

30. The method of claim 29 wherein said first synthon has the Formula Xb or Xc:

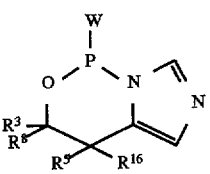

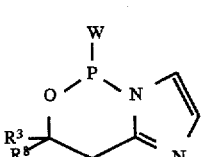

31. The method of claim 29 wherein said first synthon has the Formula XIVa:

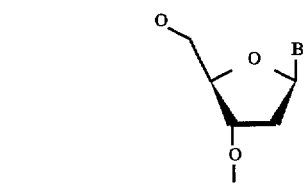

wherein p, $Z^1$ and $Z^2$ are as defined above.

32. The method of claim 31 wherein said first synthon has the Formula XVa or XVIa:

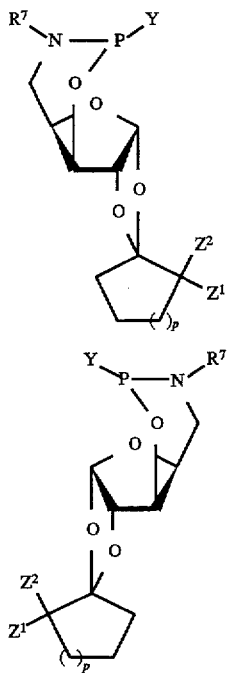
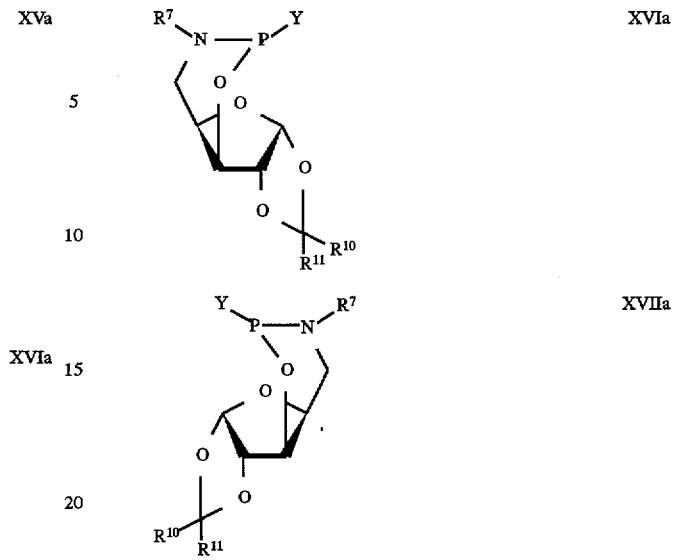
wherein Y, $R^7$, $Z^1$, $Z^2$, and p are as defined above.
33. The method of claim 29 wherein said first synthon has the Formula XVIIa or XVIIIa:
wherein W, $R^7$, $R^{10}$ and $R^{11}$ are as defined above.
34. The method of claim 1 further comprising removing said $R^9$ groups.
35. The method of claim 1 further comprising removing said $R^2$ groups.
36. The oligomer produced by the method of claim 1.
* * * * *